US011542484B2

(12) United States Patent
Zhou et al.

(10) Patent No.: US 11,542,484 B2
(45) Date of Patent: *Jan. 3, 2023

(54) GROUP OF UDP-GLYCOSYLTRANSFERASE FOR CATALYZING CARBOHYDRATE CHAIN ELONGATION AND APPLICATION THEREOF

(71) Applicant: CAS CENTER FOR EXCELLENCE IN MOLECULAR PLANT SCIENCES, Shanghai (CN)

(72) Inventors: Zhihua Zhou, Shanghai (CN); Wei Wei, Shanghai (CN); Xing Yan, Shanghai (CN); Chengshuai Yang, Shanghai (CN); Chaojing Li, Shanghai (CN); Yongjun Wei, Shanghai (CN); Pingping Wang, Shanghai (CN)

(73) Assignee: CAS Center for Excellence in Molecular Plant Sciences, Shanghai (CN)

( * ) Notice: Subject to any disclaimer, the term of this patent is extended or adjusted under 35 U.S.C. 154(b) by 91 days.

This patent is subject to a terminal disclaimer.

(21) Appl. No.: 16/614,944

(22) PCT Filed: May 21, 2018

(86) PCT No.: PCT/CN2018/087678
§ 371 (c)(1),
(2) Date: Nov. 19, 2019

(87) PCT Pub. No.: WO2018/210349
PCT Pub. Date: Nov. 22, 2018

(65) Prior Publication Data
US 2021/0163901 A1 Jun. 3, 2021

(30) Foreign Application Priority Data
May 19, 2017 (CN) .......................... 201710359069.7

(51) Int. Cl.
| | |
|---|---|
| C12N 9/10 | (2006.01) |
| C12N 15/82 | (2006.01) |
| C12P 19/18 | (2006.01) |
| C12P 19/56 | (2006.01) |

(52) U.S. Cl.
CPC ....... *C12N 9/1051* (2013.01); *C12N 15/8245* (2013.01); *C12P 19/18* (2013.01); *C12P 19/56* (2013.01); *C12N 9/10* (2013.01)

(58) Field of Classification Search
CPC .................................................. C12N 9/1048
See application file for complete search history.

(56) References Cited

U.S. PATENT DOCUMENTS 9,976,167 B2 * 5/2018 Zhou .................. C12P 33/00

FOREIGN PATENT DOCUMENTS

| CN | 104854235 A | 8/2015 |
|---|---|---|
| CN | 105177100 A | 12/2015 |
| CN | 107058446 A | 8/2017 |

OTHER PUBLICATIONS

Wang, Pingping, et al. "Production of bioactive ginsenosides Rh2 and Rg3 by metabolically engineered yeasts." Metabolic engineering 29 (2015): 97-105. (Year: 2015).*
GenBank: AKA44580.1 (Year: 2015).*
Kim, Yun-Soo, et al. "Ginseng metabolic engineering: regulation of genes related to ginsenoside biosynthesis." Journal of Medicinal Plants Research 3.13 (2009): 1270-1276 (Year: 2009).*
International Search Report & Written Opinion; PCT Application No. PCT/CN2018/087678; dated Aug. 2, 2018.
English translation of International Search Report & Written Opinion; PCT Application No. PCT/CN2018/087678; dated Aug. 2, 2018.
International Preliminary Report on Patentability; PCT Application No. PCT/CN2018/087678; dated Nov. 28, 2019.
English abstract of CN 107058446; retrieved from www.espacenet.com on Jun. 16, 2021.
English abstract of CN 105177100; retrieved from www.espacenet.com on Jun. 16, 2021.
English abstract of CN 104854235; retrieved from www.espacenet.com on Jun. 16, 2021.
Abstract of Wang, Pingping et al., "Production of bioactive ginsenosides Rh2 and Rg3 by metabolically engineered yeasts", Metabolic Engineering, vol. 29; May 31, 2015.

* cited by examiner

*Primary Examiner* — Phuong T Bui
(74) *Attorney, Agent, or Firm* — Tara A. Nealey; Rong Yang; Polsinelli PC

(57) ABSTRACT

The present invention relates to a group of glycosyltransferase, and an application thereof. Specifically, provided is using glycosyltransferase GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15, as well as derived polypeptides thereof to catalyze the first glycosyl at position C-20, the first glycosyl at position C-6, and the first glycosyl at position C-3 of a tetracyclic triterpene compound substrate to elongate a carbohydrate chain, thereby obtaining a catalytic reaction of ginsenoside products such as ginsenoside Rg3, ginsenoside Rd, ginsenoside Rb1, ginsenoside Rb3, saponin DMGG, saponin DMGX, gypenoside LXXV, gypenoside XVII, gypenoside XIII, gypenoside IX, notoginsenoside U, and notoginsenoside R1, notoginsenoside R2, notoginsenoside R3, 3-O-β-(D-xylopyranosyl)-β-(D-glucopyranosyl)-PPD, 3-O-β-(D-xylopyranosyl)-β-(D-glucopyranosyl)-CK, 20-O-Glucosylginsenoside Rf, and Ginsenoside F3. Glycosyltransferase in the present invention can further be applied to construction of artificially synthesized ginsenoside, novel ginsenoside, and derivatives thereof.

6 Claims, 8 Drawing Sheets
Specification includes a Sequence Listing.

SEQUENCE LISTING

<160> NUMBER OF SEQ ID NOS: 134

<210> SEQ ID NO 1
<211> LENGTH: 18
<212> TYPE: DNA
<213> ORGANISM: artificial sequence
<220> FEATURE:
<223> OTHER INFORMATION: primer

<400> SEQUENCE: 1
cagagttcat catggata                                                   18

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
ctagcataca aagaaagag                                                  19

<210> SEQ ID NO 3
<211> LENGTH: 1455
<212> TYPE: DNA
<213> ORGANISM: Panax ginseng
<220> FEATURE:
<221> NAME/KEY: misc_feature
<223> OTHER INFORMATION: GT29-32

<400> SEQUENCE: 3

```
ggggatcctc tagagatatc cagagttcat catggataac caagaaggta gaatcagtat      60
agcgttgcta ccattttag cccatggtca catatctccc ttctttgagc tagccaaaca      120
actcgcaaaa agaaattgca atgttttcct ctgttctacc ccaatcaatc ttagctccat     180
caagaataag gattcctctg cttctataaa actagtagag cttcatcttc cctcttcccc     240
tgatcttccc cctcactacc acaccacaaa tggcctccct tcccatctca tggtcccact    300
cagaaacgcc tttgaaacag cagcccccac cttctctgaa atccttaaaa ccttaaaccc     360
tgatttgctt atttatgatt tcaatccctc atgggcaccg gaaatcgctt cgtctcacaa    420
tattccggca gtttatttcc taacctcggc agcagccacc tcttccatgg gcctacatgc    480
tttcaaaaac tcaggtgaaa aatacccatt tccagatttt tatgataaca gtaatattac    540
ccctgaacca ccttctgcag ataaaatgaa gttattcat gattttgtcg cttgtttcaa    600
acgatcttgc gacattattt tgattaagag ttttagagaa ctggaaggga aatatattga    660
ttttctttcc actttatcta agaaaacttt ggttcctgtt ggtccactcg ttcaagatcc    720
tatgggacat gatgaagatc caaaaacagg gcatcttata aactggcttg acaagagggc    780
tgaatctaca gtggtgtttg tctgctttgg aagtgagtat tttcccctcca atgaggaatt    840 ggaagaatta gcaattgggc tagagattag catggttagt ttcatattgg ctgtgagatt    900
tcctgaagga gagaaaaaag gattttacc agagggtgt gttcaaaggg taggagacag    960
aggattggtt gtggagggt gggctccaca ggcaagaatt ttaggacatt caagcaccgg    1020
tgggtttgtg agccattgtg ggtggagttc tattatggag agtgtgaagt ttggggttcc    1080
agtaattgcc atgccaggc atcttgatca gccttttgaat gctaagctgg cggcggaggt    1140
tggtgtgggc atggaggtta tgagagatga aatggggaag tataagagag aagcgattgc    1200
agaggtaata agaaaagtcg tgatggagaa aaatggggag gttatgagga ggaaagcaag    1260
```

-continued

```
ggaattgagt gagaaaatga aagagatagg agagcaattg attgataggg cagtggagga    1320
gctagtacaa atttgtaaga agaagaaaga tgaacaatag tagtaataga ctaattttt     1380 tcccttaaa atcattttga atgcgcttag gttgggcttt gaactctttc tttgtatgct     1440
aggatatcgt cgacc                                                     1455

<210> SEQ ID NO 4
<211> LENGTH: 442
<212> TYPE: PRT
<213> ORGANISM: Panax ginseng
<220> FEATURE:
<221> NAME/KEY: misc_feature
<223> OTHER INFORMATION: GT29-32

<400> SEQUENCE: 4

Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asn Lys Asp Ser Ser Ala Ser Ile Lys Leu Val Glu Leu
        50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Arg Asn Ala Phe Glu Thr
                85                  90                  95

Ala Ala Pro Thr Phe Ser Glu Ile Leu Lys Thr Leu Asn Pro Asp Leu
                100                 105                 110

Leu Ile Tyr Asp Phe Asn Pro Ser Trp Ala Pro Glu Ile Ala Ser Ser
            115                 120                 125

His Asn Ile Pro Ala Val Tyr Phe Leu Thr Ser Ala Ala Ala Thr Ser
        130                 135                 140

Ser Met Gly Leu His Ala Phe Lys Asn Ser Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Lys Met Lys Leu Phe His Asp Phe Val Ala Cys Phe Lys Arg Ser
            180                 185                 190

Cys Asp Ile Ile Leu Ile Lys Ser Phe Arg Glu Leu Glu Gly Lys Tyr
        195                 200                 205

Ile Asp Phe Leu Ser Thr Leu Ser Lys Lys Thr Leu Val Pro Val Gly
    210                 215                 220

Pro Leu Val Gln Asp Pro Met Gly His Asp Glu Asp Pro Lys Thr Gly
225                 230                 235                 240

His Leu Ile Asn Trp Leu Asp Lys Arg Ala Glu Ser Thr Val Val Phe
                245                 250                 255

Val Cys Phe Gly Ser Glu Tyr Phe Pro Ser Asn Glu Glu Leu Glu Glu
            260                 265                 270

Leu Ala Ile Gly Leu Glu Ile Ser Met Val Ser Phe Ile Leu Ala Val
        275                 280                 285

Arg Phe Pro Glu Gly Glu Lys Lys Gly Ile Leu Pro Glu Gly Phe Val
    290                 295                 300

Gln Arg Val Gly Asp Arg Gly Leu Val Val Glu Gly Trp Ala Pro Gln
305                 310                 315                 320
```

```
Ala Arg Ile Leu Gly His Ser Ser Thr Gly Gly Phe Val Ser His Cys
            325                 330                 335

Gly Trp Ser Ser Ile Met Glu Ser Val Lys Phe Gly Val Pro Val Ile
            340                 345                 350

Ala Met Ala Arg His Leu Asp Gln Pro Leu Asn Ala Lys Leu Ala Ala
            355                 360                 365

Glu Val Gly Val Gly Met Glu Val Met Arg Asp Glu Asn Gly Lys Tyr
            370                 375                 380

Lys Arg Glu Ala Ile Ala Glu Val Ile Arg Lys Val Val Met Glu Lys
385                 390                 395                 400

Asn Gly Glu Val Met Arg Arg Lys Ala Arg Glu Leu Ser Glu Lys Met
            405                 410                 415

Lys Glu Ile Gly Glu Gln Leu Ile Asp Arg Ala Val Glu Glu Leu Val
            420                 425                 430

Gln Ile Cys Lys Lys Lys Lys Asp Glu Gln
            435                 440

<210> SEQ ID NO 5
<211> LENGTH: 1461
<212> TYPE: DNA
<213> ORGANISM: Panax ginseng
<220> FEATURE:
<221> NAME/KEY: misc_feature
<223> OTHER INFORMATION: GT29-33

<400> SEQUENCE: 5
ccggggatcc tctagagata tccagagttc atcatggata tcgaaaaagg tagaatcagt      60
atagttatgc tgccattttt agcccatggc cacatttctc cattctttga gctagccaag     120
catctctcaa aaagaaattg taatatattc ctctgttcta ccccaatcaa tcttagctcc     180
atcaagaaca gagtatctga taaggattcc tctgcttcta taaaactagt agagcttcat     240
cttccctctt cccctgatct tccccctcac taccacacca caaatggcct cccttcccat     300
ctcatggtcc cactcagaaa cgcctttgaa acagcagccc ccaccttctc tgaaatcctt     360
aaaaccttaa accctgattt gcttattat gatttcaatc cctcatgggc accggaaatc      420
gcttcgtctc acaatattcc ggcagtttat ttcctaacct cggcagcagc cacctcttcc     480
atgggcctac atgctttcaa aaactcaggt gaaaaatacc catttccaga tttttatgat     540
aacagtaata ttaccccctga ccaccttct gcagataaaa tgaagttatt tcatgatttt     600
gtcgcttgtt tcaaacgatc ttgcgacatt atttgatta agagttttag agaactggaa      660
gggaaatata ttgattttct ttccacttta tctaagaaaa ctttggttcc tgttggtcca     720
ctcgttcaag atcctatggg acatgatgaa gatccaaaaa cagggcatct tataaactgg     780
cttgacaaga gggctgaatc tacagtggtg tttgtctgct ttggaagtga gtattttccc     840
tccaatgagg aattggaaga attagcaatt gggctagaga ttagcatggt tagtttcata     900
ttggctgtga gatttcctga aggagagaaa aaagggattt taccagaggg gtttgttcaa     960
agggtaggag acagaggatt ggttgtggag ggtgggctc cacagtcaag aattttagga    1020
cattcaagca ccggtggtt tgtgagccat tgtgggtgga gttctattat ggagagtgtg    1080
aagtttgggg ttccagtaat tgccatggcc aggcatcttg atcagccttt gaatgctaag    1140
ctggcggcgg aggttggtgt gggcatggag gttatgagag atgaaaatgg gaagtataag    1200
agagaagcga ttgcagaggt aataagaaaa gtcgtgatgg agaaaatgg ggaggttatg     1260 aggaggaaag caagggaatt gagtgagaaa atgaaagtga aggagagca agagattggt     1320
```

```
agggcggtgg aggagctagt acaaatttgt aagaagaaga agcagcacgc acaatattaa    1380
tagtactttt taacccttta gtcattttta tgagctaagg tcgagttttg aactctttct    1440
ttgtatgcta ggatatcgtc g                                              1461
```

<210> SEQ ID NO 6
<211> LENGTH: 448
<212> TYPE: PRT
<213> ORGANISM: Panax ginseng
<220> FEATURE:
<221> NAME/KEY: misc_feature
<223> OTHER INFORMATION: GT29-33

<400> SEQUENCE: 6

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Tyr Phe Leu Thr Ser Ala
    130                 135                 140

Ala Ala Thr Ser Ser Met Gly Leu His Ala Phe Lys Asn Ser Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Phe Leu Ser Thr Leu Ser Lys Lys Thr Leu
    210                 215                 220

Val Pro Val Gly Pro Leu Val Gln Asp Pro Met Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Leu Ala Ile Gly Leu Glu Ile Ser Met Val Ser Phe
        275                 280                 285

Ile Leu Ala Val Arg Phe Pro Glu Gly Glu Lys Lys Gly Ile Leu Pro
    290                 295                 300

Glu Gly Phe Val Gln Arg Val Gly Asp Arg Gly Leu Val Val Glu Gly
305                 310                 315                 320

Trp Ala Pro Gln Ser Arg Ile Leu Gly His Ser Ser Thr Gly Gly Phe
                325                 330                 335
```

```
Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
            355                 360                 365

Lys Leu Ala Ala Glu Val Gly Val Gly Met Glu Val Met Arg Asp Glu
370                 375                 380

Asn Gly Lys Tyr Lys Arg Glu Ala Ile Ala Glu Val Ile Arg Lys Val
385                 390                 395                 400

Val Met Glu Lys Asn Gly Val Met Arg Arg Lys Ala Arg Glu Leu
                405                 410                 415

Ser Glu Lys Met Lys Val Lys Gly Glu Gln Glu Ile Gly Arg Ala Val
            420                 425                 430

Glu Glu Leu Val Gln Ile Cys Lys Lys Lys Gln His Ala Gln Tyr
            435                 440                 445
```

<210> SEQ ID NO 7
<211> LENGTH: 1447
<212> TYPE: DNA
<213> ORGANISM: Panax ginseng
<220> FEATURE:
<221> NAME/KEY: misc_feature
<223> OTHER INFORMATION: GT29-34

<400> SEQUENCE: 7

```
gggatcctct agagatatcc agagttcatc atggatatcg aaaaaggtag aatcattata      60
gttatgctgc catttttagc ccatggccac atttctccat tctttgagct agccaagcat     120
ctctcaaaaa gaaattgtaa tatattcctc tgttctaccc caatcaatct tagctccatc     180
aagaacagag tatctgataa ggattcctct gcttctataa aactagtaga gcttcatctt     240
ccctcttccc ctgatcttcc ccctcactac cacaccacaa atggcctccc ttcccatctc     300
atggtcccac tcagaaacgc cttgaaaca gcagccccca ccttctctga atccttaaaa      360
accttaaacc ctgatttgct tatttatgat ttcaatccct catgggcacc ggaaatcgct     420
tcgtctcaca atattccggc agtttatttc ctaacctcgg cagcagccac ctcttccatg     480
ggcctacatg ctttcaaaaa ctcaggtgaa aaatacccat tccagatttt tatgataac     540
agtaatatta ccctgaacc accttctgca gataaaatga agttattca tgattttgtc      600
gcttgtttca aacgatcttg cgacattatt ttgattaaga gttttagaga actggaaggg    660
aaatatattg attttctttc cactttatct aagaaaactt tggttcctgt tggtccactc     720
gttcaagatc ctatgggaca tgatgaagat ccaaaaacag gcatcttat aaactggctt      780
gacaagaggg ctgaatctac agtggtgttt gtctgctttg aagtgagta tttcctcc       840
aatgaggaat tggaagaatt agcaattggg ctagagatta gcatggttag tttcatattg     900
gctgtgagat ttcctgaagg agagaaaaaa gggattttac cagagggggtt tgttcaaagg    960
gtaggagaca gaggattggt tgtggagggg tgggctccac aggcaagaat tttaggacat   1020
tcaagcaccg gtgggtttgt gagccattgt gggtggagtt ctattatgga gagtgtgaag  1080
tttggggttc cagtaattgc catggccagg catcttgatc agccttgaa tgctaagctg   1140
gcggcggagg ttggtgtggg catggaggtt atgagagatg aaaatgggaa gtataagaga  1200
gaagggattg cagaggtaat aagaaaagtc gttgtggaga aagtgggga ggttatgagg    1260
aggaaagcaa gggaattgag tgagaaaatg aagagaaag gagaggaaga gattgatagg   1320
gcagtggagg agctagtaca aatttgtaag aagaagaaag atgcacaata gtaatagtag    1380
```

-continued

```
tagtactaat tttgaatgcg cttaggttgg gttttgaact ctttctttgt atgctaggat      1440
atcgtcg                                                                1447

<210> SEQ ID NO 8
<211> LENGTH: 446
<212> TYPE: PRT
<213> ORGANISM: Panax ginseng
<220> FEATURE:
<221> NAME/KEY: misc_feature
<223> OTHER INFORMATION: GT29-34

<400> SEQUENCE: 8

Met Asp Ile Glu Lys Gly Arg Ile Ile Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Tyr Phe Leu Thr Ser Ala
    130                 135                 140

Ala Ala Thr Ser Ser Met Gly Leu His Ala Phe Lys Asn Ser Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Phe Leu Ser Thr Leu Ser Lys Lys Thr Leu
    210                 215                 220

Val Pro Val Gly Pro Leu Val Gln Asp Pro Met Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Leu Ala Ile Gly Leu Glu Ile Ser Met Val Ser Phe
        275                 280                 285

Ile Leu Ala Val Arg Phe Pro Glu Gly Glu Lys Lys Gly Ile Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
```

```
                340                 345                 350
Val Pro Val Ile Ala Met Ala Arg His Leu Asp Gln Pro Leu Asn Ala
            355                 360                 365

Lys Leu Ala Ala Glu Val Gly Val Gly Met Glu Val Met Arg Asp Glu
        370                 375                 380

Asn Gly Lys Tyr Lys Arg Glu Gly Ile Ala Glu Val Ile Arg Lys Val
385                 390                 395                 400

Val Val Glu Lys Ser Gly Glu Val Met Arg Arg Lys Ala Arg Glu Leu
                405                 410                 415

Ser Glu Lys Met Lys Glu Lys Gly Glu Glu Glu Ile Asp Arg Ala Val
            420                 425                 430

Glu Glu Leu Val Gln Ile Cys Lys Lys Lys Asp Ala Gln
        435                 440                 445

<210> SEQ ID NO 9
<211> LENGTH: 23
<212> TYPE: DNA
<213> ORGANISM: artificial sequence
<220> FEATURE:
<223> OTHER INFORMATION: primer

<400> SEQUENCE: 9
gttcaaagcc caacctaagc gca                                           23

<210> SEQ ID NO 10
<211> LENGTH: 26
<212> TYPE: DNA
<213> ORGANISM: artificial sequence
<220> FEATURE:
<223> OTHER INFORMATION: primer

<400> SEQUENCE: 10
acagcaagag agagacacag agttca                                        26

<210> SEQ ID NO 11
<211> LENGTH: 1418
<212> TYPE: DNA
<213> ORGANISM: Panax ginseng
<220> FEATURE:
<221> NAME/KEY: misc_feature
<223> OTHER INFORMATION: GT29-4

<400> SEQUENCE: 11
acagcaagag agagacacag agttcattca tggataacca agaaggtaga atcagtatag    60
cgttgctacc attttagcc catggccaca tttctccatt ctttgagcta gccaagcatc    120
tctcaaaaag aaattgtaat atattcctct gttctacccc aatcaatctt agctccatca    180
agaacagaat atctgataag gattcctctg cttctataaa actagtagag cttcatcttc    240
catcttcccc tgatcttcct cctcactacc acaccacaaa tggcctccct tcccatctca    300
tggtcccact cagaaacgcc tttgaaacag cagcccccac cttctctgaa atccttaaaa    360
ccttaaaccc tgatttgctt atttatgatt tcaatccctc atgggcaccg gagatcgctt    420
cgtctcacaa tattccggca gtttgtttca taattggggg agcagcctcc ttttccatga    480
gcctacatag tttcaaaaac ccaggtgaaa atacccatt tctagatttt gatgataaca    540
gtaatattac ccctgaacca ccttcagcag ataacatgaa gttattactt gatttatga    600 cttgtttcga acgatcttgc gacattattt tgattaagag ttttagagaa ctagaaggga    660
aatattttga tttttattct actttatctg ataaaacttt ggttcctgtt ggtccactcg    720
```

-continued

```
ttcaagatcc tatgggccat aatgaagatc caaaaacaga gcagtttata aactggcttg    780
acaaaagggc tgaatctaca gtggtgtttg tctgctttgg aagtgagtat tttctctcca    840
atgaggaatt ggaagaagta gcaattgggc tagagattag catggttaat ttcatatggg    900
ctgtgagatt aattgaagga gagaaaaaag gggttttacc agaggggttt gttcaaaggg    960
taggagacag aggattggtt gtggagdggt gggctccaca ggcaagaatt ttaggacatt   1020
caagcaccgg tgggtttgtg agccattgtg ggtggagttc tattacggag agtatgaagt   1080
ttggggttcc agtaattgcc atggccaggc atcttgatca gcctttgaat ggtaagctgg   1140
cggcggaggt tggtgtgggc atggaggttg tgagagatga aaatgggaag tataagagag   1200
aagggattgc agaggtaata agaaaagtcg ttgtggagaa aagtggggag gttatgagga   1260
ggaaagcaag ggaattgagt gagaaaatga aagagaaagg agaggaagag attgataggg   1320
cagtggagga gctagtacaa atttgtaaga agaagaaaga tgcacaatag taatagtagt   1380
agtactaatt ttgaatgcgc ttaggttggg ctttgaac                            1418
```

<210> SEQ ID NO 12
<211> LENGTH: 446
<212> TYPE: PRT
<213> ORGANISM: Panax ginseng
<220> FEATURE:
<221> NAME/KEY: misc_feature
<223> OTHER INFORMATION: GT29-4

<400> SEQUENCE: 12

```
Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys His Leu Ser
                20                  25                  30

Lys Arg Asn Cys Asn Ile Phe Leu Cys Ser Thr Pro Ile Asn Leu Ser
            35                  40                  45

Ser Ile Lys Asn Arg Ile Ser Asp Lys Asp Ser Ala Ser Ile Lys
        50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Phe Asp Phe Tyr Ser Thr Leu Ser Asp Lys Thr Leu
    210                 215                 220

Val Pro Val Gly Pro Leu Val Gln Asp Pro Met Gly His Asn Glu Asp
225                 230                 235                 240
```

```
Pro Lys Thr Glu Gln Phe Ile Asn Trp Leu Asp Lys Arg Ala Glu Ser
                245                 250                 255

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285

Ile Trp Ala Val Arg Leu Ile Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Thr Glu Ser Met Lys Phe Gly
            340                 345                 350

Val Pro Val Ile Ala Met Ala Arg His Leu Asp Gln Pro Leu Asn Gly
        355                 360                 365

Lys Leu Ala Ala Glu Val Gly Val Gly Met Glu Val Val Arg Asp Glu
    370                 375                 380

Asn Gly Lys Tyr Lys Arg Glu Gly Ile Ala Glu Val Ile Arg Lys Val
385                 390                 395                 400

Val Val Glu Lys Ser Gly Glu Val Met Arg Arg Lys Ala Arg Glu Leu
                405                 410                 415

Ser Glu Lys Met Lys Glu Lys Gly Glu Glu Ile Asp Arg Ala Val
            420                 425                 430

Glu Glu Leu Val Gln Ile Cys Lys Lys Lys Asp Ala Gln
        435                 440                 445

<210> SEQ ID NO 13
<211> LENGTH: 1434
<212> TYPE: DNA
<213> ORGANISM: Panax ginseng
<220> FEATURE:
<221> NAME/KEY: misc_feature
<223> OTHER INFORMATION: GT29-5

<400> SEQUENCE: 13
acagcaagag agagacacag agttcattca tggataacca aaagggtaga atcagtatag      60
ttatgctgcc attttagcc catggccaca tttctccatt ctttgagcta gccaagcatc     120
tctcaaaaag aaattgtaat atattcctct gttctacccc aatcaatctt agctccatca     180
agaacagaat atctgataag gattcctctg cttctataaa actagtagag cttcatcttc     240
catcttcccc tgatcttcct cctcactacc acaccacaaa tggcctccct tcccatctca     300
tggtcccact cagaaacgcc tttgaaacag cagcccccac cttctctgaa atccttaaaa     360
ccttaaaccc tgatttgctt atttatgatt tcaatccctc atgggcaccg gagatcgctt     420
cgtctcacaa tattccggca gtttgtttca taattggggg agcagcctcc ttttccatga     480
gcctacatag tttcaaaaac ccaggtgaaa ataccccatt tctagatttt gatgataaca     540
gtaatattac ccctgaacca ccttcagcag ataacatgaa gttattactt gatttttatga    600 cttgtttcga acgatcttgc gacattattt tgattaagag ttttagagaa ctagaaggga     660
aatatatcga tttgctttcc actttatctg ataaaacttt ggttcctgtt ggtccactcg     720
ttcaagatcc tatgggccat aatgaagatc aaaaacaga gcagattata aactggcttg     780
acaaaagggc tgaatctaca gtggtgtttg tctgctttgg aagtgagtat tttctctcca     840
```

```
atgaggaatt ggaagaagta gcaattgggc tagagattag catggttaat ttcatatggg    900
ctgtgagatt aattgaagga gagaaaaaag gggttttacc agagggattt gttcaaaggg    960
taggagacag aggattggtt gtggaggggt gggctccaca ggcaagaatt ttaggacatt   1020
caagcaccgg tgggtttgtg agccattgtg ggtggagttc tattgcggag agtatgaagt   1080
ttggggttcc agtaattgcc atggccaggc atcttgatca gcctttgaat ggtaagctgg   1140
cggcggaggt tggtgtgggc atggaggttg tgagagatga aaatgggaag tataagagag   1200
aagggattgc agaggtaata agaaaagtcg ttgtggagaa aagtggggag gttatcagga   1260
ggaaagcaag ggaattgagt gagaaaatga aagagatagg agagcaattg attgataggg   1320
cagtggagga gctagtacaa atttgtaaga agaagaaaga tgaacaatag tagtaataga   1380 ctaattttt tcccttttaaa atcattttga atgcgcttag gttgggcttt gaac          1434
```

<210> SEQ ID NO 14
<211> LENGTH: 446
<212> TYPE: PRT
<213> ORGANISM: Panax ginseng
<220> FEATURE:
<221> NAME/KEY: misc_feature
<223> OTHER INFORMATION: GT29-5

<400> SEQUENCE: 14

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Asp Lys Thr Leu
    210                 215                 220

Val Pro Val Gly Pro Leu Val Gln Asp Pro Met Gly His Asn Glu Asp
225                 230                 235                 240

Pro Lys Thr Glu Gln Ile Ile Asn Trp Leu Asp Lys Arg Ala Glu Ser
                245                 250                 255
```

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285

Ile Trp Ala Val Arg Leu Ile Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Ala Glu Ser Met Lys Phe Gly
            340                 345                 350

Val Pro Val Ile Ala Met Ala Arg His Leu Asp Gln Pro Leu Asn Gly
        355                 360                 365

Lys Leu Ala Ala Glu Val Gly Val Gly Met Glu Val Val Arg Asp Glu
    370                 375                 380

Asn Gly Lys Tyr Lys Arg Glu Gly Ile Ala Glu Val Ile Arg Lys Val
385                 390                 395                 400

Val Val Glu Lys Ser Gly Glu Val Ile Arg Arg Lys Ala Arg Glu Leu
                405                 410                 415

Ser Glu Lys Met Lys Glu Ile Gly Glu Gln Leu Ile Asp Arg Ala Val
            420                 425                 430

Glu Glu Leu Val Gln Ile Cys Lys Lys Lys Asp Glu Gln
        435                 440                 445

<210> SEQ ID NO 15
<211> LENGTH: 1484
<212> TYPE: DNA
<213> ORGANISM: Panax ginseng
<220> FEATURE:
<221> NAME/KEY: misc_feature
<223> OTHER INFORMATION: GT29-7

<400> SEQUENCE: 15
aatgaaatta tacagagagg gagagaaaca gagttcattc atggataacc aaaaaggtag      60
aatcagtata gcgttgctac cattttttagc ccatggtcac atatctccct tctttgagct    120
agccaaacaa ctcgcaaaaa gaaattgcaa tgttttcctc tgttctaccc caatcaatct    180
tagctccatc aagaacagag tatctgataa ggattcctct gcttctataa aactagtaga    240
gcttcatctt ccatcttccc ctgatcttcc tcctcactac cacaccacaa atggcctccc    300
ttcccatctc atgatcccac tcagaaacgc ctttgataca gcaggcccca ccttctctga    360
aatccttaaa accttaaacc ctgatttgct tatttatgat ttcaatccct catgggcacc    420
ggagatcgct tcgtctcaca atattccggc agtttgtttc ataattggtg agcagcctc    480 ctcttccatg agcctacata gtttcaaaaa cccaggtgaa aaatacccat tctagatttt    540
tgatgataac agtaatatta cccctgaacc accttcagca gataacatga agctattaat    600 taatttatg acttgtttcg aacgatcttg cgacattatt ttgattaaga gttttagaga    660
actagaaggg aaatattttg atttttttc cactttatct gataaaactt tggttcctgt    720
tggtccactc gttcaagatc ctatgggcca taatgaagat ccaaaaacag agcagtttat    780
aaactggctt gacaaagggg ctgaatctac agtggtgttt gtctgctttg aagtgagtg    840 ttttctctcc aatgaggaat tggaagaagt agcgattggg ctagagatta gcatggttaa    900
tttcatatgg gctgtgagat taattgaagg agagaaaaaa ggggtttttac cagagggggtt    960

```
tgttcaaagg gtaggagaca gaggattggt tgtggaggag tgggctccac aggcaagaat    1020
tttaggacat tcaagcaccg gtgggtttgt gagccattgt gggtggaatt ctattacgga    1080
gagtatgaag tttggggttc cagtaattgc catggccagg cattttgatc agcctttgaa    1140
tggtaagctg gcggcggagg ttggtgtggg catggaggtt gtgagagatg aaaatgggaa    1200
gtataagaga gaagggattg cagaggtaat aagaaaagtc gttgtggaga aagtgggga    1260 ggttatcagg aggaaagcaa gggaattgag tgagaaaatg aaagagaaag gagagcaaga    1320
gattgatagg gtagtggagg agctagtaca aatttgtaag aagaagaaag atgaacaata    1380
gtaataggac tactttttt acctttagaa tcattttgaa tgcgcttaag gttgagtttt    1440
taactttttc tttgtacttg tactttgtgt tgtgaagaaa acca                     1484
```

<210> SEQ ID NO 16
<211> LENGTH: 446
<212> TYPE: PRT
<213> ORGANISM: Panax ginseng
<220> FEATURE:
<221> NAME/KEY: misc_feature
<223> OTHER INFORMATION: GT29-7

<400> SEQUENCE: 16

```
Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Ile Pro Leu Arg Asn
                85                  90                  95

Ala Phe Asp Thr Ala Gly Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Ser Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Ile Asn Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Phe Asp Phe Phe Ser Thr Leu Ser Asp Lys Thr Leu
    210                 215                 220

Val Pro Val Gly Pro Leu Val Gln Asp Pro Met Gly His Asn Glu Asp
225                 230                 235                 240

Pro Lys Thr Glu Gln Phe Ile Asn Trp Leu Asp Lys Arg Ala Glu Ser
                245                 250                 255

Thr Val Val Phe Val Cys Phe Gly Ser Glu Cys Phe Leu Ser Asn Glu
            260                 265                 270
```

Glu Leu Glu Glu Val Ala Ile Gly Leu Glu Ile Ser Met Val Asn Phe
            275                 280                 285

Ile Trp Ala Val Arg Leu Ile Glu Gly Glu Lys Lys Gly Val Leu Pro
        290                 295                 300

Glu Gly Phe Val Gln Arg Val Gly Asp Arg Gly Leu Val Val Glu Glu
305                 310                 315                 320

Trp Ala Pro Gln Ala Arg Ile Leu Gly His Ser Ser Thr Gly Phe
                325                 330                 335

Val Ser His Cys Gly Trp Asn Ser Ile Thr Glu Ser Met Lys Phe Gly
            340                 345                 350

Val Pro Val Ile Ala Met Ala Arg His Phe Asp Gln Pro Leu Asn Gly
        355                 360                 365

Lys Leu Ala Ala Glu Val Gly Val Gly Met Glu Val Val Arg Asp Glu
370                 375                 380

Asn Gly Lys Tyr Lys Arg Glu Gly Ile Ala Glu Val Ile Arg Lys Val
385                 390                 395                 400

Val Val Glu Lys Ser Gly Glu Val Ile Arg Arg Lys Ala Arg Glu Leu
            405                 410                 415

Ser Glu Lys Met Lys Lys Gly Glu Gln Glu Ile Asp Arg Val Val
        420                 425                 430

Glu Glu Leu Val Gln Ile Cys Lys Lys Lys Asp Glu Gln
        435                 440                 445

<210> SEQ ID NO 17
<211> LENGTH: 1432
<212> TYPE: DNA
<213> ORGANISM: Panax ginseng
<220> FEATURE:
<221> NAME/KEY: misc_feature
<223> OTHER INFORMATION: GT29-9

<400> SEQUENCE: 17
acagcaagag agagacacag agttcattca tggataacca aaagggtaga atcagtatag      60
ttatgctgcc attttagcc catggccaca tttctccatt ctttgagcta gccaagcatc     120
tctcaaaaag aaattgtaat atattcctct gttctacccc aatcaatctt agctccatca     180
agaacagaat atctgataag gattcctctg cttctataaa actagtagag cttcatcttc     240
catcttcccc tgatcttcct cctcactacc acaccacaaa tggcctccct tcccatctca     300
tggtcccact cagaaacgcc tttgaaacag cagcccccac cttctctgaa atccttaaaa     360
ccttaaaccc tgatttgctt atttatgatt caatcccctc atgggcaccg agatcgctt     420 cgtctcacaa tattccggca gtttgtttca taattggggg agcagcctcc ttttccatga     480
gcctacatag tttcaaaaac ccaggtgaaa atacccatt tctagatttt gatgataaca     540
gtaatattac ccctgaacca ccttcagcag ataacatgaa gttattactt gatttttatga     600 cttgtttcga acgatcttgc gacattattt tgattaagag ttttagagaa ctagaaggga     660
aatattttga ttttttattct actttatctg ataaaacttt ggttcctgtt ggtccactcg     720
ttcaagatcc tatgggccat aatgaagatc aaaaacaga gcagtttata aactggcttg     780 acaaagggc tgaatctaca gtggtgtttg tctgctttgg aagtgagtat tttctctcca     840
atgaggaatt ggaagaagta gcaattgggc tagagattag catggttaat ttcatatggg     900
ctgtgagatt aattgaagga gagaaaaaag gggttttacc agaggattt gttcaaaggg     960 taggagacag aggattggtt gtggaggggt gggctccaca ggcaagaatt ttaggacatt    1020

```
caagcaccgg tgggtttgtg agccattgtg ggtggagttc tattgcggag agtatgaagt      1080
ttggggttcc agtaattgcc atggccaggc atcttgatca gcctttgaat ggtaagctgg      1140
cggcggaggt tggtgtgggc atggaggttg tgagagatga aaatgggaag tataagagag      1200
aagatattgc aggggtaata agaaaagtcg tggtggagaa aagtggggag gttatcagga      1260
ggaaagcaag ggaattgagt gagaaaatga aagagatagg agagcaattg attgataggg      1320
cagtggagga gctagtacaa atttgtaaga agaagaaaga tgaacaatag tagtaataga      1380 ctaattttt tcccttaaa atcatttga atgcgcttag gttgggcttt ga               1432
```

<210> SEQ ID NO 18
<211> LENGTH: 446
<212> TYPE: PRT
<213> ORGANISM: Panax ginseng
<220> FEATURE:
<221> NAME/KEY: misc_feature
<223> OTHER INFORMATION: GT29-9

<400> SEQUENCE: 18

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Phe Asp Phe Tyr Ser Thr Leu Ser Asp Lys Thr Leu
    210                 215                 220

Val Pro Val Gly Pro Leu Val Gln Asp Pro Met Gly His Asn Glu Asp
225                 230                 235                 240

Pro Lys Thr Glu Gln Phe Ile Asn Trp Leu Asp Lys Arg Ala Glu Ser
                245                 250                 255

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285
```

```
Ile Trp Ala Val Arg Leu Ile Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Ala Glu Ser Met Lys Phe Gly
                340                 345                 350

Val Pro Val Ile Ala Met Ala Arg His Leu Asp Gln Pro Leu Asn Gly
                355                 360                 365

Lys Leu Ala Ala Glu Val Gly Val Gly Met Glu Val Val Arg Asp Glu
370                 375                 380

Asn Gly Lys Tyr Lys Arg Glu Asp Ile Ala Gly Val Ile Arg Lys Val
385                 390                 395                 400

Val Val Glu Lys Ser Gly Glu Val Ile Arg Arg Lys Ala Arg Glu Leu
                405                 410                 415

Ser Glu Lys Met Lys Glu Ile Gly Glu Gln Leu Ile Asp Arg Ala Val
                420                 425                 430

Glu Glu Leu Val Gln Ile Cys Lys Lys Lys Asp Glu Gln
435                 440                 445
```

<210> SEQ ID NO 19
<211> LENGTH: 1434
<212> TYPE: DNA
<213> ORGANISM: Panax ginseng
<220> FEATURE:
<221> NAME/KEY: misc_feature
<223> OTHER INFORMATION: GT29-11

<400> SEQUENCE: 19

```
acagcaagag agagacacag agttcattca tggataacca aaagggtaga atcagtatag      60
ttatgctgcc attttttagcc catggccaca tttctccatt ctttgagcta gccaagcatc     120
tctcaaaaag aaattgtaat atattcctct gttctacccc aatcaatctt agctccatca     180
agaacagaat atctgataag gattcctctg cttctataaa actagtagag cttcatcttc     240
catcttcccc tgatcttcct cctcactacc acaccacaaa tggcctccct tcccatctca     300
tggtcccact cagaaacgcc tttgaaacag cagcccccac cttctctgaa atccttaaaa     360
ccttaaaccc tgatttgctt atttatgatt tcaatccctc atgggcaccg agatcgctt      420
cgtctcacaa tattccggca gtttgtttca taattggggg agcagcctcc ttttccatga     480
gcctacatag tttcaaaaac ccaggtgaaa atacccattt tctagatttt gatgataaca     540
gtaatattac ccctgaacca ccttcagcag ataacatgaa gttattactt gattttatga     600
cttgtttcga acgatcttgc gacattattt tgattaagag ttttagagaa ctagaaggga     660
aatattttga tttttattct actttatctg ataaaacttt ggttcctgtt ggtccactcg     720
ttcaagatcc tatgggccat aatgaagatc aaaaacaga gcagtttata aactggcttg      780
acaaaagggc tgaatctaca gtggtgtttg tctgctttgg aagtgagtat tttctctcca     840
atgaggaatt ggaagaagta gcaattgggc tagagattag catggttaat ttcatatggg     900
ctgtgagatt aattgaagga gagaaaaaag gggttttacc agaggggttt gttcaaaggg     960
taggagacag aggattggtt gtggaggggt gggctccaca ggcaagaatt ttaggacatt    1020
caagcaccgg tgggtttgtg agccattgtg ggtggagttc tattacggag agtatgaagt    1080
ttgggggttcc agtaattgcc atggccaggc atttttgatca gcctttgaat gctaagctgg    1140
```

```
cggcggaggt tggtgtgggc atggaggttg tgagagatga aaatgggaag tataagagag    1200
aagatattgc aggggtaata agaaaagtcg tggtggagaa aagtggggag gttatcagga    1260
ggaaagcaag ggaattgagt gagaaaatga aagagatagg agagcaattg attgataggg    1320
cagtggagga gctagtacaa atttgtaaga agaagaaaga tgaacaatag tagtaataga    1380 ctaattttt tcccttaaa atcattttga atgcgcttag gttgggcttt gaat           1434
```

<210> SEQ ID NO 20
<211> LENGTH: 446
<212> TYPE: PRT
<213> ORGANISM: Panax ginseng
<220> FEATURE:
<221> NAME/KEY: misc_feature
<223> OTHER INFORMATION: GT29-11

<400> SEQUENCE: 20

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
                20                  25                  30

Lys Arg Asn Cys Asn Ile Phe Leu Cys Ser Thr Pro Ile Asn Leu Ser
            35                  40                  45

Ser Ile Lys Asn Arg Ile Ser Asp Lys Asp Ser Ser Ala Ser Ile Lys
        50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Ile Asn
                85                  90                  95

Ala Phe Glu Thr Ala Gly Pro Thr Phe Ser Glu Ile Leu Lys Thr Leu
                100                 105                 110

Asn Pro Asp Leu Leu Ile Tyr Asp Phe Asn Pro Ser Trp Ala Pro Glu
            115                 120                 125

Ile Ala Ser Ser His Asn Ile Pro Ala Val Tyr Phe Leu Thr Thr Ala
        130                 135                 140

Ala Ala Ser Ser Ser Ile Gly Leu His Ala Phe Lys Asn Pro Gly Glu
145                 150                 155                 160

Lys Tyr Pro Phe Pro Asp Phe Tyr Asp Asn Ser Asn Asn Thr Pro Glu
                165                 170                 175

Pro Pro Ser Ala Asp Asn Met Lys Leu Leu His Asp Phe Ile Ala Cys
                180                 185                 190

Phe Glu Arg Ser Cys Asp Ile Ile Leu Ile Lys Ser Phe Ile Glu Leu
            195                 200                 205

Glu Gly Lys Tyr Ile Asp Leu Leu Ser Thr Leu Ser Asp Lys Thr Leu
        210                 215                 220

Val Pro Val Gly Pro Leu Val Gln Asp Pro Met Gly His Asn Glu Asp
225                 230                 235                 240

Pro Lys Thr Glu Gln Ile Ile Asn Trp Leu Asp Lys Arg Ala Glu Ser
                245                 250                 255

Thr Val Val Phe Val Cys Phe Gly Ser Glu Tyr Phe Leu Ser Asn Glu
                260                 265                 270

Glu Leu Glu Glu Val Ala Ile Gly Leu Glu Ile Ser Met Val Asn Phe
            275                 280                 285

Ile Trp Ala Val Arg Leu Ile Glu Gly Glu Lys Lys Gly Val Leu Pro
        290                 295                 300

Glu Gly Phe Val Gln Arg Val Gly Asp Arg Gly Leu Val Val Glu Gly
```

```
                    305                 310                 315
Trp Ala Pro Gln Ala Arg Ile Leu Gly His Ser Ser Thr Gly Gly Phe
                325                 330                 335

Val Ser His Cys Gly Trp Ser Ser Ile Ala Glu Ser Met Lys Phe Gly
            340                 345                 350

Val Pro Val Ile Ala Met Ala Arg His Leu Asp Gln Pro Leu Asn Gly
        355                 360                 365

Lys Leu Ala Ala Glu Val Gly Val Gly Met Glu Val Val Arg Asp Glu
    370                 375                 380

Asn Gly Lys Tyr Lys Arg Glu Gly Ile Ala Glu Val Ile Arg Lys Val
385                 390                 395                 400

Val Val Glu Lys Ser Gly Glu Val Met Arg Arg Lys Ala Arg Glu Leu
                405                 410                 415

Ser Glu Lys Met Lys Glu Lys Gly Glu Glu Ile Asp Arg Ala Val
                420                 425                 430

Glu Glu Leu Val Gln Ile Cys Lys Lys Lys Asp Ala Gln
            435                 440                 445
```

<210> SEQ ID NO 21
<211> LENGTH: 1434
<212> TYPE: DNA
<213> ORGANISM: Panax ginseng
<220> FEATURE:
<221> NAME/KEY: misc_feature
<223> OTHER INFORMATION: GT29-13

<400> SEQUENCE: 21

```
acagcaagag agagacacag agttcattca tggataacca aaagggtaga atcagtatag      60
ttatgctgcc attttagcc catggccaca tttctccatt ctttgagcta gccaagcatc     120
tctcaaaaag aaattgtaat atattcctct gttctacccc aatcaatctt agctccatca     180
agaacagaat atctgataag gattcctctg cttctataaa actagtagag cttcatcttc     240
catcttcccc tgatcttcct cctcactacc acaccacaaa tggcctccct tcccatctca     300
tggtcccact cagaaacgcc tttgaaacag cagcccccac cttctctgaa atccttaaaa     360
ccttaaaccc tgatttgctt attatatgatt tcaatccctc atgggcaccg agatcgctt      420 cgtctcacaa tattccggca gtttgtttca taattggggg agcagcctcc ttttccatga     480
gcctacatag tttcaaaaac ccaggtgaaa atacccatt tctagatttt gatgataaca      540
gtaatattac ccctgaacca ccttcagcag ataacatgaa gttattactt gattttatga     600
cttgtttcga acgatcttgc gacattattt tgattaagag ttttagagaa ctagaaggga     660
aatattttga tttttattct actttatctg ataaaacttt ggttcctgtt ggtccactcg     720
ttcaagatcc tatgggccat aatgaagatc aaaaacaga gcagtttata aactggcttg      780 acaaagggc tgaatctaca gtggtgtttg tctgctttgg aagtgagtat tttctctcca     840
atgaggaatt ggaagaagta gcaattgggc tagagattag catggttaat ttcatatggg     900
ctgtgagatt aattgaagga gagaaaaaag gggttttacc agaggggttt gttcaaaggg     960
taggagacag aggattggtt gtggagggt gggctccaca ggcaagaatt ttaggacatt    1020
caagcaccgg tgggtttgtg agccattgtg ggtggagttc tattacggag agtatgaagt    1080
ttggggttcc agtaattgcc atggccaggc attttgatca gcctttgaat gctaagctgg    1140
cggcggaggt tggtgtggtc atggaggttg tgagagatga aaatgggaag tataagagag    1200
aagatattgc agggtaata agaaaagtcg tggtggagaa aagtggggag gttatcagga    1260
```

```
ggaaagcaag ggaattgagt gagaaaatga aagagatagg agagcaattg attgataggg    1320
cagtggagga gctagtacaa atttgtaaga agaagaaaga tgaacaatag tagtaataga    1380 ctaattttt tcccttaaa atcatttga atgcgcttag gttgggcttt gaac             1434
```

<210> SEQ ID NO 22
<211> LENGTH: 446
<212> TYPE: PRT
<213> ORGANISM: Panax ginseng
<220> FEATURE:
<221> NAME/KEY: misc_feature
<223> OTHER INFORMATION: GT29-13

<400> SEQUENCE: 22

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Phe Asp Phe Tyr Ser Thr Leu Ser Asp Lys Thr Leu
    210                 215                 220

Val Pro Val Gly Pro Leu Val Gln Asp Pro Met Gly His Asn Glu Asp
225                 230                 235                 240

Pro Lys Thr Glu Gln Phe Ile Asn Trp Leu Asp Lys Arg Ala Glu Ser
                245                 250                 255

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285

Ile Trp Ala Val Arg Leu Ile Glu Gly Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335
```

```
Val Ser His Cys Gly Trp Ser Ser Ile Thr Glu Ser Met Lys Phe Gly
            340                 345                 350

Val Pro Val Ile Ala Met Ala Arg His Phe Asp Gln Pro Leu Asn Ala
            355                 360                 365

Lys Leu Ala Ala Glu Val Gly Val Met Val Val Arg Asp Glu
370                 375                 380

Asn Gly Lys Tyr Lys Arg Glu Asp Ile Ala Gly Val Ile Arg Lys Val
385                 390                 395                 400

Val Val Glu Lys Ser Gly Val Ile Arg Arg Lys Ala Arg Glu Leu
            405                 410                 415

Ser Glu Lys Met Lys Glu Ile Gly Glu Gln Leu Ile Asp Arg Ala Val
            420                 425                 430

Glu Glu Leu Val Gln Ile Cys Lys Lys Lys Asp Glu Gln
            435                 440                 445
```

<210> SEQ ID NO 23
<211> LENGTH: 1422
<212> TYPE: DNA
<213> ORGANISM: Panax ginseng
<220> FEATURE:
<221> NAME/KEY: misc_feature
<223> OTHER INFORMATION: GT29-17

<400> SEQUENCE: 23

```
acagcaagag agagacacag agttcattca tggataacca agaaggtaga atcagtatag      60
cgttgctacc attttagcc catggtcaca tatctccctt ctttgagcta gccaaacaac     120
tcgcaaaaag aaattgcaat gttttcctct gttctacccc aatcaatctt agctccatca     180
agaataagga ttcctctgct tctataaaac tagttgagct tcatcttcca tcttcccctg     240
atcttcctcc tcactatcac accacaaatg cctcccttc ccatctcatg gtcccactca     300
taaacgcctt tgaaacagca ggccccacct tctctgaaat ccttaaaacc ttaaaccctg     360
atttgcttat ttatgatttc aatccctcat gggcaccgga gatcgcttcg tctcacaata     420
ttccggcagt ttgtttcata attggggag cagcctcctt ttccatgagc ctacatagtt     480
tcaaaaaccc aggtgaaaaa tacccatttc tagattttga tgataacagt aatattaccc     540
ctgaaccacc ttcagcagat aacatgaagt tattacttga ttttatgact tgtttcgaac     600
gatcttgcga cattattttg attaagagtt ttagagaact agaagggaaa tattttgatt     660
tttattctac tttatctgat aaaactttgg ttcctgttgg tccactcgtt caagatccta     720
tgggccataa tgaagatcca aaaacagagc agtttataaa ctggcttgac aaaagggctg     780
aatctacagt ggtgtttgtc tgctttggaa gtgagtattt tctctccaat gaggaattgg     840
aagaagtagc aattgggcta gagattagca tggttaattt catatgggct gtgagattaa     900
ttgaaggaga gaaaaaaggg gttttaccag aggggtttgt tcaaagggta ggagacagag    960
gattggttgt ggaggggtgg gctccacagg caagaatttt aggacattca agcaccggtg   1020
ggtttgtgag ccattgtggg tggagttcta ttacggagag tatgaagttt ggggttccag   1080
taattgccat ggccaggcat tttgatcagc ctttgaatgc aagctggcg gcggaggttg   1140
gtgtgggcat ggaggttgtg agagatgaaa atggaagta agagagaa gatattgcag   1200
gggtaataag aaaagtcgtg gtggagaaaa gtggggaggt tatcaggagg aaagcaaggg   1260
aattgagtga gaaaatgaaa gagataggag agcaattgat tgatagggca gtggaggagc   1320
tagtacaaat ttgtaagaag aagaaagatg aacaatagta gtaatagact aattttttc    1380
```

```
cctttaaaat cattttgaat gcgcttaggt tgggctttga ac                              1422
```

<210> SEQ ID NO 24
<211> LENGTH: 442
<212> TYPE: PRT
<213> ORGANISM: Panax ginseng
<220> FEATURE:
<221> NAME/KEY: misc_feature
<223> OTHER INFORMATION: GT29-17

<400> SEQUENCE: 24

| Met | Asp | Asn | Gln | Glu | Gly | Arg | Ile | Ser | Ile | Ala | Leu | Leu | Pro | Phe | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asn Lys Asp Ser Ser Ala Ser Ile Lys Leu Val Glu Leu
    50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Ile Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Cys Phe Ile Ile Gly Gly Ala Ala Ser Phe
    130                 135                 140

Ser Met Ser Leu His Ser Phe Lys Asn Pro Gly Glu Lys Tyr Pro Phe
145                 150                 155                 160

Leu Asp Phe Asp Asp Asn Ser Asn Ile Thr Pro Glu Pro Pro Ser Ala
                165                 170                 175

Asp Asn Met Lys Leu Leu Leu Asp Phe Met Thr Cys Phe Glu Arg Ser
            180                 185                 190

Cys Asp Ile Ile Leu Ile Lys Ser Phe Arg Glu Leu Glu Gly Lys Tyr
        195                 200                 205

Phe Asp Phe Tyr Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Phe Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
        275                 280                 285

Arg Leu Ile Glu Gly Glu Lys Lys Gly Val Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Thr Glu Ser Met Lys Phe Gly Val Pro Val Ile
            340                 345                 350

```
Ala Met Ala Arg His Phe Asp Gln Pro Leu Asn Ala Lys Leu Ala Ala
            355                 360                 365

Glu Val Gly Val Gly Met Glu Val Val Arg Asp Glu Asn Gly Lys Tyr
370                 375                 380

Lys Arg Glu Asp Ile Ala Gly Val Ile Arg Lys Val Val Glu Lys
385                 390                 395                 400

Ser Gly Glu Val Ile Arg Arg Lys Ala Arg Glu Leu Ser Glu Lys Met
                405                 410                 415

Lys Glu Ile Gly Glu Gln Leu Ile Asp Arg Ala Val Glu Glu Leu Val
                420                 425                 430

Gln Ile Cys Lys Lys Lys Lys Asp Glu Gln
                435                 440
```

<210> SEQ ID NO 25
<211> LENGTH: 1417
<212> TYPE: DNA
<213> ORGANISM: Panax ginseng
<220> FEATURE:
<221> NAME/KEY: misc_feature
<223> OTHER INFORMATION: GT29-18

<400> SEQUENCE: 25

| | | | | | |
|---|---|---|---|---|---|
| acagcaagag | agagacacag | agttcattca | tggataacca | aaagggtaga | atcagtatag | 60 |
| ttatgctgcc | attttagcc | catggccaca | tttctccatt | ctttgagcta | gccaagcatc | 120 |
| tctcaaaaag | aaattgtaat | atattcctct | gttctacccc | aatcaatctt | agctccatca | 180 |
| agaacagaat | atctgataag | gattcctctg | cttctataaa | actagtagag | cttcatcttc | 240 |
| catcttcccc | tgatcttcct | cctcactacc | acaccacaaa | tggcctccct | tcccatctca | 300 |
| tggtcccact | cagaaacgcc | tttgaaacag | cagcccccac | cttctctgaa | atccttaaaa | 360 |
| ccttaaaccc | tgatttgctt | atttatgatt | tcaatccctc | atgggcaccg | gagatcgctt | 420 |
| cgtctcacaa | tattccggca | gtttgtttca | taattggggg | agcagcctcc | ttttccatga | 480 |
| gcctacatag | tttcaaaaac | ccaggtgaaa | aatacccatt | tctagatttt | gatgataaca | 540 |
| gtaatattac | ccctgaacca | ccttcagcag | ataacatgaa | gttattactt | gattttatga | 600 |
| cttgtttcga | acgatcttgc | gacattattt | tgattaagag | ttttagagaa | ctagaaggga | 660 |
| aatatttga | tttttattct | actttatctg | ataaaacttt | ggttcctgtt | ggtccactcg | 720 |
| ttcaagatcc | tatgggccat | aatgaagatc | caaaaacaga | gcagtttata | aactggcttg | 780 |
| acaaaagggc | tgaatctaca | gtggtgtttg | tctgctttgg | aagtgagtat | tttctctcca | 840 |
| atgaggaatt | ggaagaagta | gcaattgggc | tagagattag | catggttaat | ttcatatggg | 900 |
| ctgtgagatt | aattgaagga | gagaaaaaag | gggtttacc | agaggggttt | gttcaaaggg | 960 |
| taggagacag | aggattggtt | gtggaggggt | gggctccaca | ggcaagaatt | ttaggacatt | 1020 |
| caagcaccgg | tgggtttgtg | agccattgtg | ggtggagttc | tattacggag | agtatgaagt | 1080 |
| ttggggttcc | agtaattgcc | atggccaggc | attttgatca | gcctttgaat | gctaagctgg | 1140 |
| cggcggaggt | tggtgtgggc | atgagaggttg | tgagagatga | aaatgggaag | tataagagag | 1200 |
| aagatattgc | agggtaata | agaaaagtcg | tggtggagaa | aagtggggag | gttatgagga | 1260 |
| ggaaagcaag | ggaattgagt | gagaaaatga | aagagaaagg | agaggaagag | attgataggg | 1320 |
| cagtggagga | gctagtacaa | atttgtaaga | agaagaaaga | tgcacaatag | taatagtagt | 1380 |
| agtactaatt | ttgaatgcgc | ttaggttggg | cttaatc | | | 1417 |

<210> SEQ ID NO 26

<211> LENGTH: 446
<212> TYPE: PRT
<213> ORGANISM: Panax ginseng
<220> FEATURE:
<221> NAME/KEY: misc_feature
<223> OTHER INFORMATION: GT29-18

<400> SEQUENCE: 26

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Cys Phe Ile Ile Gly Gly
    130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Phe Asp Phe Tyr Ser Thr Leu Ser Asp Lys Thr Leu
    210                 215                 220

Val Pro Val Gly Pro Leu Val Gln Asp Pro Met Gly His Asn Glu Asp
225                 230                 235                 240

Pro Lys Thr Glu Gln Phe Ile Asn Trp Leu Asp Lys Arg Ala Glu Ser
                245                 250                 255

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285

Ile Trp Ala Val Arg Leu Ile Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Thr Glu Ser Met Lys Phe Gly
            340                 345                 350

Val Pro Val Ile Ala Met Ala Arg His Phe Asp Gln Pro Leu Asn Ala
        355                 360                 365

Lys Leu Ala Ala Glu Val Gly Val Gly Met Glu Val Val Arg Asp Glu
```

```
                370             375             380
Asn Gly Lys Tyr Lys Arg Glu Asp Ile Ala Gly Val Ile Arg Lys Val
385                 390                 395                 400

Val Val Glu Lys Ser Gly Glu Val Met Arg Arg Lys Ala Arg Glu Leu
                405                 410                 415

Ser Glu Lys Met Lys Glu Lys Gly Glu Glu Ile Asp Arg Ala Val
            420                 425                 430

Glu Glu Leu Val Gln Ile Cys Lys Lys Lys Asp Ala Gln
        435                 440                 445

<210> SEQ ID NO 27
<211> LENGTH: 1418
<212> TYPE: DNA
<213> ORGANISM: Panax ginseng
<220> FEATURE:
<221> NAME/KEY: misc_feature
<223> OTHER INFORMATION: GT29-24

<400> SEQUENCE: 27
acagcaagag agagacacag agttcattca tggataacca aaagggtaga atcagtatag      60
ttatgctgcc attttagcc catggccaca tttctccatt ctttgagcta gccaagcatc     120
tctcaaaaag aaattgtaat atattcctct gttctacccc aatcaatctt agctccatca    180
agaacagaat atctgataag gattcctctg cttctataaa actagtagag cttcatcttc    240
catcttcccc tgatcttcct cctcactacc acaccacaaa tggcctccct tcccatctca    300
tggtcccact cagaaacgcc tttgaaacag cagcccccac cttctctgaa atccttaaaa    360
ccttaaaccc tgatttgctt atttatgatt tcaatccctc atgggcaccg gagatcgctt    420
cgtctcacaa tattccggca gtttgtttca taattggggg agcagcctcc ttttccatga    480
gcctacatag tttcaaaaac ccaggtgaaa ataccccatt tctagatttt gatgataaca    540
gtaatattac ccctgaacca ccttcagcag ataacatgaa gttattactt gatttttatga   600 cttgtttcga acgatcttgc gacattattt tgattaagag ttttagagaa ctagaaggga    660
aatattttga ttttttattct actttatctg ataaaacttt ggttcctgtt ggtccactcg   720
ttcaagatcc tatgggccat aatgaagatc aaaaacaga gcagtttata aactggcttg     780
acaaaagggc tgaatctaca gtggtgtttg tctgctttgg aagtgagtat tttctctcca    840
atgaggaatt ggaagaagta gcaattgggc tagagattag catggttaat tcatatgggg    900
ctgtgagatt aattgaagga gagaaaaaag gggttttacc agaggggttt gttcaaaggg    960
taggagacag aggattggtt gtggaggggt gggctccaca ggcaagaatt ttaggacatt   1020
caagcaccgg tgggtttgtg agccattgtg ggtggagttc tattacggag agtatgaagt   1080
ttggggttcc agtaattgcc atggccaggc attttgatca gcctttgaat gctaagctgg   1140
cggcggaggt tggtgtgggc atggaggttg tgagagatga aaatgggaag tataagagag   1200
aagggattgc agaggtaata agaaaagtcg ttgtggagaa aagtggggag gttatgagga   1260
ggaaagcaag ggaattgagt gagaaaatga aagagaaagg agaggaagag attgataggg   1320
cagtggagga gctagtacaa atttgtaaga agaagaaaga tgcacaatag taatagtagt   1380
agtactaatt ttgaatgcgc ttaggttggg ctttgaac                           1418

<210> SEQ ID NO 28
<211> LENGTH: 446
<212> TYPE: PRT
<213> ORGANISM: Panax ginseng
<220> FEATURE:
```

<221> NAME/KEY: misc_feature
<223> OTHER INFORMATION: GT29-24

<400> SEQUENCE: 28

| | | | | | | | | | | | | | | |
|---|---|---|---|---|---|---|---|---|---|---|---|---|---|---|
| Met | Asp | Asn | Gln | Lys | Gly | Arg | Ile | Ser | Ile | Val | Met | Leu | Pro | Phe | Leu |
| 1 | | | | 5 | | | | | 10 | | | | | 15 | |
| Ala | His | Gly | His | Ile | Ser | Pro | Phe | Phe | Glu | Leu | Ala | Lys | His | Leu | Ser |
| | | | 20 | | | | | 25 | | | | | 30 | | |
| Lys | Arg | Asn | Cys | Asn | Ile | Phe | Leu | Cys | Ser | Thr | Pro | Ile | Asn | Leu | Ser |
| | | 35 | | | | | 40 | | | | | 45 | | | |
| Ser | Ile | Lys | Asn | Arg | Ile | Ser | Asp | Lys | Asp | Ser | Ser | Ala | Ser | Ile | Lys |
| | 50 | | | | | 55 | | | | | 60 | | | | |
| Leu | Val | Glu | Leu | His | Leu | Pro | Ser | Ser | Pro | Asp | Leu | Pro | Pro | His | Tyr |
| 65 | | | | | 70 | | | | | 75 | | | | | 80 |
| His | Thr | Thr | Asn | Gly | Leu | Pro | Ser | His | Leu | Met | Val | Pro | Leu | Arg | Asn |
| | | | | 85 | | | | | 90 | | | | | 95 | |
| Ala | Phe | Glu | Thr | Ala | Ala | Pro | Thr | Phe | Ser | Glu | Ile | Leu | Lys | Thr | Leu |
| | | | 100 | | | | | 105 | | | | | 110 | | |
| Asn | Pro | Asp | Leu | Leu | Ile | Tyr | Asp | Phe | Asn | Pro | Ser | Trp | Ala | Pro | Glu |
| | | 115 | | | | | 120 | | | | | 125 | | | |
| Ile | Ala | Ser | Ser | His | Asn | Ile | Pro | Ala | Val | Cys | Phe | Ile | Ile | Gly | Gly |
| | 130 | | | | | 135 | | | | | 140 | | | | |
| Ala | Ala | Ser | Phe | Ser | Met | Ser | Leu | His | Ser | Phe | Lys | Asn | Pro | Gly | Glu |
| 145 | | | | | 150 | | | | | 155 | | | | | 160 |
| Lys | Tyr | Pro | Phe | Leu | Asp | Phe | Asp | Asn | Ser | Asn | Ile | Thr | Pro | Glu |
| | | | | 165 | | | | | 170 | | | | | 175 | |
| Pro | Pro | Ser | Ala | Asp | Asn | Met | Lys | Leu | Leu | Leu | Asp | Phe | Met | Thr | Cys |
| | | | 180 | | | | | 185 | | | | | 190 | | |
| Phe | Glu | Arg | Ser | Cys | Asp | Ile | Ile | Leu | Ile | Lys | Ser | Phe | Arg | Glu | Leu |
| | | 195 | | | | | 200 | | | | | 205 | | | |
| Glu | Gly | Lys | Tyr | Phe | Asp | Phe | Tyr | Ser | Thr | Leu | Ser | Asp | Lys | Thr | Leu |
| | 210 | | | | | 215 | | | | | 220 | | | | |
| Val | Pro | Val | Gly | Pro | Leu | Val | Gln | Asp | Pro | Met | Gly | His | Asn | Glu | Asp |
| 225 | | | | | 230 | | | | | 235 | | | | | 240 |
| Pro | Lys | Thr | Glu | Gln | Phe | Ile | Asn | Trp | Leu | Asp | Lys | Arg | Ala | Glu | Ser |
| | | | | 245 | | | | | 250 | | | | | 255 | |
| Thr | Val | Val | Phe | Val | Cys | Phe | Gly | Ser | Glu | Tyr | Phe | Leu | Ser | Asn | Glu |
| | | | 260 | | | | | 265 | | | | | 270 | | |
| Glu | Leu | Glu | Glu | Val | Ala | Ile | Gly | Leu | Glu | Ile | Ser | Met | Val | Asn | Phe |
| | | 275 | | | | | 280 | | | | | 285 | | | |
| Ile | Trp | Ala | Val | Arg | Leu | Ile | Glu | Gly | Glu | Lys | Lys | Gly | Val | Leu | Pro |
| | 290 | | | | | 295 | | | | | 300 | | | | |
| Glu | Gly | Phe | Val | Gln | Arg | Val | Gly | Asp | Arg | Gly | Leu | Val | Val | Glu | Gly |
| 305 | | | | | 310 | | | | | 315 | | | | | 320 |
| Trp | Ala | Pro | Gln | Ala | Arg | Ile | Leu | Gly | His | Ser | Ser | Thr | Gly | Gly | Phe |
| | | | | 325 | | | | | 330 | | | | | 335 | |
| Val | Ser | His | Cys | Gly | Trp | Ser | Ser | Ile | Thr | Glu | Ser | Met | Lys | Phe | Gly |
| | | | 340 | | | | | 345 | | | | | 350 | | |
| Val | Pro | Val | Ile | Ala | Met | Ala | Arg | His | Phe | Asp | Gln | Pro | Leu | Asn | Ala |
| | | 355 | | | | | 360 | | | | | 365 | | | |
| Lys | Leu | Ala | Ala | Glu | Val | Gly | Val | Gly | Met | Glu | Val | Val | Arg | Asp | Glu |
| | 370 | | | | | 375 | | | | | 380 | | | | |
| Asn | Gly | Lys | Tyr | Lys | Arg | Glu | Gly | Ile | Ala | Glu | Val | Ile | Arg | Lys | Val |
| 385 | | | | | 390 | | | | | 395 | | | | | 400 |

Val Val Glu Lys Ser Gly Glu Val Met Arg Arg Lys Ala Arg Glu Leu
            405                 410                 415

Ser Glu Lys Met Lys Glu Lys Gly Glu Glu Ile Asp Arg Ala Val
        420                 425                 430

Glu Glu Leu Val Gln Ile Cys Lys Lys Lys Asp Ala Gln
        435                 440                 445

<210> SEQ ID NO 29
<211> LENGTH: 1434
<212> TYPE: DNA
<213> ORGANISM: Panax ginseng
<220> FEATURE:
<221> NAME/KEY: misc_feature
<223> OTHER INFORMATION: GT29-25

<400> SEQUENCE: 29

| | | | | | |
|---|---|---|---|---|---|
| acagcaagag | agagacacag | agttcattca | tggataacca | aaagggtaga | atcagtatag | 60 |
| ttatgctgcc | attttagcc | catggccaca | tttctccatt | ctttgagcta | gccaagcatc | 120 |
| tctcaaaaag | aaattgtaat | atattcctct | gttctacccc | aatcaatctt | agctccatca | 180 |
| agaacagaat | atctgataag | gattcctctg | cttctataaa | actagtagag | cttcatcttc | 240 |
| catcttcccc | tgatcttcct | cctcactacc | acaccacaaa | tggcctccct | tcccatctca | 300 |
| tggtcccact | cagaaacgcc | tttgaaacag | cagcccccac | cttctctgaa | tccttaaaa | 360 |
| ccttaaaccc | tgatttgctt | atttatgatt | tcaatccctc | atgggcaccg | gagatcgctt | 420 |
| cgtctcacaa | tattccggca | gtttgtttca | taattggggg | agcagcctcc | ttttccatga | 480 |
| gcctacatag | tttcaaaaac | ccaggtgaaa | aatacccatt | tctagatttt | gatgataaca | 540 |
| gtaatattac | ccctgaacca | ccttcagcag | ataacatgaa | gttattactt | gattttatga | 600 |
| cttgtttcga | acgatcttgc | gacattattt | tgattaagag | ttttagagaa | ctagaaggga | 660 |
| aatattttga | tttttattct | actttatctg | ataaaactt | ggttcctgtt | ggtccactcg | 720 |
| ttcaagatcc | tatgggccat | aatgaagatc | caaaaacaga | gcagtttata | aactggcttg | 780 |
| acaaaagggc | tgaatctaca | gtggtgtttg | tctgctttgg | aagtgagtat | tttctctcca | 840 |
| atgaggaatt | ggaagaagta | gcaattgggc | tagagattag | catggttaat | ttcatatggg | 900 |
| ctgtgagatt | aattgaagga | gagaaaaaag | gggttttacc | agagggtttt | gttcaaaggg | 960 |
| taggagacag | aggattggtt | gtggagggt | gggctccaca | ggcaagaatt | ttaggacatt | 1020 |
| caagcaccgg | tgggtttgtg | agccattgtg | ggtggagttc | tattacggag | agtatgaagt | 1080 |
| ttggggttcc | agtaattgcc | atggccaggc | attttgatca | gcctttgaat | gctaagctgg | 1140 |
| cggcggaggt | tggtgtgggc | acggaggttg | tgagagatga | aaatgggaag | tataagagag | 1200 |
| aagatattgc | aggggtaata | agaaaagtcg | tggtggagaa | aagtggggag | gttatcagga | 1260 |
| ggaaagcaag | ggaattgagt | gagaaaatga | agagataggg | agagcaattg | attgatagg | 1320 |
| cagtggagga | gctagtacaa | atttgtaaga | agaagaaaga | tgaacaatag | tagtaataga | 1380 |
| ctaattttt | tcccttaaa | atcatttga | atgcgcttag | gttgggcttt | gaac | 1434 |

<210> SEQ ID NO 30
<211> LENGTH: 446
<212> TYPE: PRT
<213> ORGANISM: Panax ginseng
<220> FEATURE:
<221> NAME/KEY: misc_feature
<223> OTHER INFORMATION: GT29-25

<400> SEQUENCE: 30

-continued

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
                20                  25                  30

Lys Arg Asn Cys Asn Ile Phe Leu Cys Ser Thr Pro Ile Asn Leu Ser
            35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
                100                 105                 110

Asn Pro Asp Leu Leu Ile Tyr Asp Phe Asn Pro Ser Trp Ala Pro Glu
            115                 120                 125

Ile Ala Ser Ser His Asn Ile Pro Ala Val Cys Phe Ile Ile Gly Gly
        130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Leu Asp Phe Met Thr Cys
            180                 185                 190

Phe Glu Arg Ser Cys Asp Ile Ile Leu Ile Lys Ser Phe Arg Glu Leu
            195                 200                 205

Glu Gly Lys Tyr Phe Asp Phe Tyr Ser Thr Leu Ser Asp Lys Thr Leu
        210                 215                 220

Val Pro Val Gly Pro Leu Val Gln Asp Pro Met Gly His Asn Glu Asp
225                 230                 235                 240

Pro Lys Thr Glu Gln Phe Ile Asn Trp Leu Asp Lys Arg Ala Glu Ser
                245                 250                 255

Thr Val Val Phe Val Cys Phe Gly Ser Glu Tyr Phe Leu Ser Asn Glu
                260                 265                 270

Glu Leu Glu Glu Val Ala Ile Gly Leu Glu Ile Ser Met Val Asn Phe
            275                 280                 285

Ile Trp Ala Val Arg Leu Ile Glu Gly Glu Lys Gly Val Leu Pro
        290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Thr Glu Ser Met Lys Phe Gly
            340                 345                 350

Val Pro Val Ile Ala Met Ala Arg His Phe Asp Gln Pro Leu Asn Ala
            355                 360                 365

Lys Leu Ala Ala Glu Val Gly Val Gly Thr Glu Val Val Arg Asp Glu
        370                 375                 380

Asn Gly Lys Tyr Lys Arg Glu Asp Ile Ala Gly Val Ile Arg Lys Val
385                 390                 395                 400

Val Val Glu Lys Ser Gly Glu Val Ile Arg Arg Lys Ala Arg Glu Leu
                405                 410                 415
```

Ser Glu Lys Met Lys Glu Ile Gly Glu Gln Leu Ile Asp Arg Ala Val
            420                 425                 430

Glu Glu Leu Val Gln Ile Cys Lys Lys Lys Asp Glu Gln
        435                 440                 445

<210> SEQ ID NO 31
<211> LENGTH: 43
<212> TYPE: DNA
<213> ORGANISM: artificial sequence
<220> FEATURE:
<223> OTHER INFORMATION: primer

<400> SEQUENCE: 31
taagaaggag ataccatg gataaccaag aaggtagaat cag                      43

<210> SEQ ID NO 32
<211> LENGTH: 44
<212> TYPE: DNA
<213> ORGANISM: artificial sequence
<220> FEATURE:
<223> OTHER INFORMATION: primer

<400> SEQUENCE: 32
tgcggccgca agcttgtcga cttgttcatc tttcttcttc ttac                   44

<210> SEQ ID NO 33
<211> LENGTH: 42
<212> TYPE: DNA
<213> ORGANISM: artificial sequence
<220> FEATURE:
<223> OTHER INFORMATION: primer

<400> SEQUENCE: 33
taagaaggag ataccatg gataaccaaa agggtagaat ca                       42

<210> SEQ ID NO 34
<211> LENGTH: 42
<212> TYPE: DNA
<213> ORGANISM: artificial sequence
<220> FEATURE:
<223> OTHER INFORMATION: primer

<400> SEQUENCE: 34
tgcggccgca agcttgtcga cttgtgcatc tttcttcttc tt                     42

<210> SEQ ID NO 35
<211> LENGTH: 43
<212> TYPE: DNA
<213> ORGANISM: artificial sequence
<220> FEATURE:
<223> OTHER INFORMATION: primer

<400> SEQUENCE: 35
taagaaggag ataccatg gataaccaaa aaggtagaat cag                      43

<210> SEQ ID NO 36
<211> LENGTH: 43
<212> TYPE: DNA
<213> ORGANISM: artificial sequence
<220> FEATURE:
<223> OTHER INFORMATION: primer

<400> SEQUENCE: 36
taagaaggag ataccatg gatatcgaaa aaggtagaat cag                      43

<210> SEQ ID NO 37
<211> LENGTH: 39
<212> TYPE: DNA
<213> ORGANISM: artificial sequence
<220> FEATURE:
<223> OTHER INFORMATION: primer

<400> SEQUENCE: 37
tgcggccgca agcttgtcga catattgtgc gtgctgctt                                39

<210> SEQ ID NO 38
<211> LENGTH: 1344
<212> TYPE: DNA
<213> ORGANISM: ????(Panax notoginseng)

<400> SEQUENCE: 38
atggatatcg aaaaggtag aatcagtata gttatgctgc cattttagc ccatggtcac           60 atatctccat tctttgagct agccaagcat ctctcaaaaa gaaattgcaa tatattcctc        120
tgttctaccc caatcaatct tagctccatc aagagcagag tatctgataa ggattcctct        180
gcttctataa aactagtaga gcttcatctt ccatcttccc ctgatcttcc tcctcagtac        240
cacaccacaa atggcctccc ttcccatctc atggtcccac tcaaaaacgc ctttgaaaca        300
gtaggcccca ccttctctga atccttaaaa accttagacc ctgatttgct tatttatgat        360
ttcaatccct catgggcacc ggagatcgct ttgtctcaca atattccggc agtttatttc        420
ctaacctcgg cagcagccac ctcttccgtg gccctacgtg ctttgaaaaa cccaggtgaa        480
aaatacccat ttccagattt ttatgataac agtaatatta ccctgaacc accttctgca         540 gataaaatga agctatttca tgattttgtt gcttgtttca acgatcttg cgacattatt         600 ttgattaaga gttttagaga actagaaggg aaatatattg atttgctttc cactttatct        660
aagaaaactt tggttcctgt tggtccactc gttcaagatc ctttgggaca tgatgaagat        720
ccaaaaacag gcatcttat aaactggctt gacaaaggg ctgaatctac agtggtgttt          780
gtctgctttg gaagtgagta ttttccctcc aatgaggaat tggaagaagt agcaattggg        840
ctagagatta gcatggttaa tttcatattg gctgttagat tcttgaagg agagaaaaaa         900 ggggttttac cagaagggtt tgttcaaagg gtaggagaca gaggattggt tgtggagggg        960
tgggctccac aggcaagaat tttaggacat tcaagcaccg tgggtttgt gagccattgt        1020 gggtggagtt ctattatgga gagtgtgaag tttgggttc cagtaattgc catggccagg        1080
catcttgatc agcctttgaa tgctaagctg gcggcggagg ttggtgtggg catggaggtt        1140
gtgagagatg aaaatgggaa gtatacgaga aagcgattg cagaggtaat aagaaaagtt        1200
gtgatggaga aaaatgggga ggttatcagg aggaaagcaa gggaattgag tgataaaatg        1260
aaagagaaag gagagcaaga gattggtagg gcagtggagg agctagtaca aatttgtaag        1320
atgaagaaag acgcacaata ttaa                                              1344

<210> SEQ ID NO 39
<211> LENGTH: 447
<212> TYPE: PRT
<213> ORGANISM: ????(Panax notoginseng)

<400> SEQUENCE: 39

Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

```
Lys Arg Asn Cys Asn Ile Phe Leu Cys Ser Thr Pro Ile Asn Leu Ser
         35                  40                  45
Ser Ile Lys Ser Arg Val Ser Asp Lys Asp Ser Ala Ser Ile Lys
 50                  55                  60
Leu Val Glu Leu His Leu Pro Ser Ser Pro Asp Leu Pro Pro Gln Tyr
 65                  70                  75                  80
His Thr Thr Asn Gly Leu Pro Ser His Leu Met Val Pro Leu Lys Asn
                 85                  90                  95
Ala Phe Glu Thr Val Gly Pro Thr Phe Ser Glu Ile Leu Lys Thr Leu
                100                 105                 110
Asp Pro Asp Leu Leu Ile Tyr Asp Phe Asn Pro Ser Trp Ala Pro Glu
             115                 120                 125
Ile Ala Leu Ser His Asn Ile Pro Ala Val Tyr Phe Leu Thr Ser Ala
         130                 135                 140
Ala Ala Thr Ser Ser Val Ala Leu Arg Ala Leu Lys Asn Pro Gly Glu
145                 150                 155                 160
Lys Tyr Pro Phe Pro Asp Phe Tyr Asp Asn Ser Asn Ile Thr Pro Glu
                165                 170                 175
Pro Pro Ser Ala Asp Lys Met Lys Leu Phe His Asp Phe Val Ala Cys
             180                 185                 190
Phe Lys Arg Ser Cys Asp Ile Ile Leu Ile Lys Ser Phe Arg Glu Leu
         195                 200                 205
Glu Gly Lys Tyr Ile Asp Leu Leu Ser Thr Leu Ser Lys Lys Thr Leu
         210                 215                 220
Val Pro Val Gly Pro Leu Val Gln Asp Pro Leu Gly His Asp Glu Asp
225                 230                 235                 240
Pro Lys Thr Gly His Leu Ile Asn Trp Leu Asp Lys Arg Ala Glu Ser
                245                 250                 255
Thr Val Val Phe Val Cys Phe Gly Ser Glu Tyr Phe Pro Ser Asn Glu
             260                 265                 270
Glu Leu Glu Glu Val Ala Ile Gly Leu Glu Ile Ser Met Val Asn Phe
         275                 280                 285
Ile Leu Ala Val Arg Phe Leu Glu Gly Glu Lys Lys Gly Val Leu Pro
     290                 295                 300
Glu Gly Phe Val Gln Arg Val Gly Asp Arg Gly Leu Val Val Glu Gly
305                 310                 315                 320
Trp Ala Pro Gln Ala Arg Ile Leu Gly His Ser Ser Thr Gly Gly Phe
                325                 330                 335
Val Ser His Cys Gly Trp Ser Ser Ile Met Glu Ser Val Lys Phe Gly
             340                 345                 350
Val Pro Val Ile Ala Met Ala Arg His Leu Asp Gln Pro Leu Asn Ala
         355                 360                 365
Lys Leu Ala Ala Glu Val Gly Val Gly Met Glu Val Val Arg Asp Glu
     370                 375                 380
Asn Gly Lys Tyr Thr Arg Glu Ala Ile Ala Glu Val Ile Arg Lys Val
385                 390                 395                 400
Val Met Glu Lys Asn Gly Glu Val Ile Arg Arg Lys Ala Arg Glu Leu
                405                 410                 415
Ser Asp Lys Met Lys Glu Lys Gly Glu Gln Glu Ile Gly Arg Ala Val
             420                 425                 430
Glu Glu Leu Val Gln Ile Cys Lys Met Lys Lys Asp Ala Gln Tyr
         435                 440                 445
```

```
<210> SEQ ID NO 40
<211> LENGTH: 1329
<212> TYPE: DNA
<213> ORGANISM: ????(Panax notoginseng)

<400> SEQUENCE: 40
atggataacc aaaaaggtag aatcagtata gcgttgctac cattttttagc ccatggtcac      60 atatctccct tctttgagct agccaaacaa ctggcaaaaa gaaattgcaa tgttttcctc     120
tgttctaccc caatcaatct tagctccatc aagaataagg attcctctgc ttctgtaaaa     180
ctagttgagc ttcatcttcc atcttcccct gatcttcctc ctcactatca caccacaaat     240
ggcctccctt cccatctcat ggtcccactc agaaacgcct ttgaaacagt aggccccacc     300
ttctctgaaa tccttaaaac cttaaaccct gatttgctta tttatgattt caatccctca     360
tgggcaccgg agatcgcttc gtctcacaat attccggcag tttatttcct aaccacggca     420
gcagccagct cttccattgg cctacatgct ttcaaaaacc caggtgaaaa atacccattt     480
ccagattttt atgataacag taatattacc cctgaaccac ttctgcaga taacatgaag     540 ctacttcatg attttatcgc ttgtttcgaa cgatcttgcg atattatttt gattaagagt     600
tttagagaac tagaagggaa atatattgat ttgctttcca ctttatctga taaaactttg     660
gttcctgttg gtccactcgt tcaagatcct atgggccata tgaagatcc aaaaacagag     720 cagattataa actggcttga caaaagggct gaatctacag tggtgtttgt ctgctttgga     780
agtgagtatt ttctctccaa tgaggaattg aagaagtag caattgggct agagattagc     840
atggttaatt tcatatgggc tgtgagatta attgaaggag agaaaaaagg ggttttacca     900
gagggggttg ttcaaagggt aggagacaga ggattggttg tggagggtg ggctccacag     960 gcaagaattt taggacattc aagcaccggt gggtttgtga ccattgtgg gtggagttct    1020 attgcggaga gtatgaggtt tggggttcca gtaattgcca tggctaggca tcttgatcag    1080
cctttgaatg ctaagctggc ggcggaggtt ggtgtgggca tggaggttgt aagagatgat    1140
aatgggaaat ataagaggga aggattgca gaggtaataa gaaaagtcgt tgtggagaaa    1200
agtggggagg ttatcaggag gaaagcaagg gagttgagtg agaaaatgaa agagaaagga    1260
gagcaagaga ttgatagggc agtggaggag ctagtacaaa tttgtaagaa gaagaaagat    1320
gcacaatag                                                            1329

<210> SEQ ID NO 41
<211> LENGTH: 442
<212> TYPE: PRT
<213> ORGANISM: ????(Panax notoginseng)

<400> SEQUENCE: 41

Met Asp Asn Gln Lys Gly Arg Ile Ser Ile Ala Leu Leu Pro Phe Leu
 1               5                  10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asn Lys Asp Ser Ser Ala Ser Val Lys Leu Val Glu Leu
    50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Arg Asn Ala Phe Glu Thr
                85                  90                  95
```

```
Val Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
        275                 280                 285

Arg Leu Ile Glu Gly Lys Lys Gly Val Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Arg Phe Gly Val Pro Val Ile
            340                 345                 350

Ala Met Ala Arg His Leu Asp Gln Pro Leu Asn Ala Lys Leu Ala Ala
        355                 360                 365

Glu Val Gly Val Gly Met Glu Val Val Arg Asp Asp Asn Gly Lys Tyr
    370                 375                 380

Lys Arg Glu Gly Ile Ala Gly Val Ile Arg Lys Val Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Val Glu Glu Leu Val
            420                 425                 430

Gln Ile Cys Lys Lys Lys Lys Asp Ala Gln
        435                 440
```

<210> SEQ ID NO 42
<211> LENGTH: 1344
<212> TYPE: DNA
<213> ORGANISM: ????(Panax notoginseng)

<400> SEQUENCE: 42
atggatatcg agaaaggtag aatcagtata gttatgctac cattttttagc ccatggtcac    60 atatctccat tctttgagct agccaagcat ctctcaaaaa gaaattgcaa tatattcctc   120
tgttctaccc caatcaatct tagctccatc aagaacagag tatctgataa ggattcctct   180

```
gcttcaataa aactagtaga gcttcatctt ccatcttccc ctgatcttcc tcctcagtac    240
cacaccacaa atggcctccc ttcccatctc atggtcccac tcaaaaacgc ctttgaaaca    300
gtaggcccca ccttctctga aatccttaaa accttagacc ctgatttgct tatttatgat    360
ttcaatccct catgggcacc ggagatcgct tgtctcaca atattccggc agtttatttc    420
ctaacctcgg cagcagccac ctcttccgtg gccctacgtg ctttgaaaaa cccaggtgaa    480
aaatacccat ttccagattt ttatgataac agtaatatta ccctgaacc accttctgca    540 gataaaatga agctatttca tgattttgtt gcttgtttca aacgatcttg cgacattatt    600
ttgattaaga gttttagaga actagaaggg aaatatattg atttgctttc cactttatct    660
aagaaaactt tggttcctgt tggtccactc gttcaagatc ctttgggaca tgatgaagat    720
ccaaaaacag ggcatcttat aaactggctt gacaaaaggg ctgaatctac agtggtgttt    780
gtctgctttg aagtgagta ttttccctcc aatgaggaat tggaagaagt agcaattggg    840
ctagagatta gcatggttaa tttcatattg gctgtgagat tcttgaagg agagaaaaaa    900 ggggttttac cagagggggtt tgttcaaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttggggttc cagtaattgc catggccagg   1080
catcttgatc agccttttgaa tgctaagctg gcggcggagg tcggtgtggg catggaggtt   1140
gtgagagatg aaaatgggaa gtataagaga gaagcgattg cagaggtaat aagaaaagtc   1200
gtgatggaga aaaatgggga ggttatcagg aggaaagcaa gggaattgag tgagaaaatg   1260
aaagagacag gagagcaaga gattggtagg gcagtggagg agctagtaca aatttgtaag   1320
atgaagaaag acgcacaata ttaa                                           1344
```

<210> SEQ ID NO 43
<211> LENGTH: 447
<212> TYPE: PRT
<213> ORGANISM: ????(Panax notoginseng)

<400> SEQUENCE: 43

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160
```

```
Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
    210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Val Arg Asp Glu
    370                 375                 380

Asn Gly Lys Tyr Lys Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415

Ser Glu Lys Met Lys Glu Thr Gly Glu Gln Glu Ile Gly Arg Ala Val
            420                 425                 430

Glu Glu Leu Val Gln Ile Cys Lys Met Lys Lys Asp Ala Gln Tyr
        435                 440                 445

<210> SEQ ID NO 44
<211> LENGTH: 1344
<212> TYPE: DNA
<213> ORGANISM: ????(Panax notoginseng)

<400> SEQUENCE: 44
atggatatcg aaaaaggtag aatcagtata gttatgctgc cattttttagc ccatggtcac      60 atatctccat tctttgagct agccaagcat ctctcaaaaa gaaattgcaa tatattcctc     120
tgttctaccc caatcaatct tagctccatc aagaacagag tatctgataa ggattcctct     180
gcttctataa aactagtaga gcttcatctt ccatcttccc ctgatcttcc tcctcagtac     240
cacaccacaa atggcctccc ttcccatctc atggtcccac tcaaaaacgc ctttgaaaca     300
gtaggcccca ccttctctga aatccttaaa accttagacc ctgatttgct tatttatgat     360
ttcaatccct catgggcacc ggagatcgct ttgtctcaca atattccggc agtttatttc     420
ctaacctcgg cagcagccac ctcttccgtg gccctacgtg ctttgaaaaa cccaggtgaa     480 aaataccccat ttccagattt ttatgataac agtaatatta cccctgaacc accttctgca     540
```

-continued

```
gataaaatga agctatttca tgattttgtt gcttgtttca aacgatcttg cgacattatt       600
ttgattaaga gttttagaga actagaaggg aaatatattg atttgctttc cactttatct       660
aagaaaactt tggttcctgt tggtccactc gttcaagatc ctttgggaca tgatgaagat       720
ccaaaaacag gcatcttat aaactggctt gacaaaaggg ctgaatctac agtggtgttt       780
gtctgctttg gaagtgagta ttttcccctcc aatgaggaat tggaagaagt agcaattggg     840
ctagagatta gcatggttaa tttcatattg gctgttagat ttcttgaagg agagaaaaaa       900
ggggttttac cagaagggtt tgttcaaagg gtaggagaca gaggattggt tgtggagggg      960
tgggctccac aggcaagaat tttaggacat tcaagcaccg gtgggtttgt gagccattgt      1020
gggtggagtt ctattatgga gagtgtgaag tttggggttc cagtaattgc catggccagg    1080
catcttgatc agccttttgaa tgctaagctg gcggcggagg ttggtgtggg catggaggtt    1140
gtgagagatg aaaatgggaa gtatacgaga gaagcgattg cagaggtaat aagaaaagtt    1200
gtgatggaga aaaatgggga ggttatcagg aggaaagcaa gggaattgag tgataaaatg    1260
aaagagaaag gagagcaaga gattggtagg gcagtggagg agctagtaca aatttgtaag    1320
atgaagaaag acgcacaata ttaa                                            1344
```

<210> SEQ ID NO 45
<211> LENGTH: 447
<212> TYPE: PRT
<213> ORGANISM: ????(Panax notoginseng)

<400> SEQUENCE: 45

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Thr Leu
    210                 215                 220
```

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
            245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
            275                 280                 285

Ile Leu Ala Val Arg Phe Leu Glu Gly Glu Lys Lys Gly Val Leu Pro
            290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
            325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
            355                 360                 365

Lys Leu Ala Ala Glu Val Gly Val Gly Met Glu Val Val Arg Asp Glu
370                 375                 380

Asn Gly Lys Tyr Thr Arg Glu Ala Ile Ala Glu Val Ile Arg Lys Val
385                 390                 395                 400

Val Met Glu Lys Asn Gly Glu Val Ile Arg Arg Lys Ala Arg Glu Leu
            405                 410                 415

Ser Asp Lys Met Lys Glu Lys Gly Glu Gln Ile Gly Arg Ala Val
            420                 425                 430

Glu Glu Leu Val Gln Ile Cys Lys Met Lys Lys Asp Ala Gln Tyr
            435                 440                 445

<210> SEQ ID NO 46
<211> LENGTH: 1344
<212> TYPE: DNA
<213> ORGANISM: ????(Panax notoginseng)

<400> SEQUENCE: 46
atggatatcg aaaaggtag aatcagtata gttatgctgc cattttttagc ccatggtcac    60 atatctccat tctttgagct agccaagcat ctctcaaaaa gaaattgcaa tatattcctc   120
tgttctaccc caatcaatct tagctccatc aagaacagag tatctgataa ggattcctct   180
gcttctataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca cctctctga atccttaaa accttagacc ctgatttgct tatttatgat   360
ttcaatccct catgggcacc ggagatcgct tgtctcaca atattccggc agtttatttc   420
ctaacctcgg cagcagccac ctcttccgtg gccctacgtg ctttgaaaaa cccaggtgaa   480
aaatacccat ttccagattt tatgataac agtaatatta cccctgaacc accttctgca   540
gataaaatga agctatttca tgattttgtt gcttgtttca acgatcttg cgacattatt   600 ttgattaaga gttttagaga actagaaggg aaatatattg atttgctttc cactttatct   660
aagaaaactt tggttcctgt tggtccactc gttcaagatc ctttgggaca tgatgaagat   720
ccaaaaacag gcatcttat aaactggctt gacaaaaggg ctgaatctac agtggtgttt   780
gtctgctttg gaagtgagta tttccctcc aatgaggaat tggaagaagt agcaattggg   840
ctagagatta gcatggttaa tttcatattg gctgttagat tcttgaagg agagaaaaaa   900

-continued

```
ggggttttac cagaagggtt tgttcaaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttggggttc cagtaattgc catggccagg   1080
catcttgatc agccttttgaa tgctaagctg gcggcggagg ttggtgtggg catggaggtt   1140
gtgagagatg aaaatgggaa gtatacgaga gaagcgattg cagaggtaat aagaaaagtt   1200
gtgatggaga aaaatgggga ggttatcagg aggaaagcaa gggaattgag tgataaaatg   1260
aaagagaaag gagagcaaga gattggtagg gcagtggagg agctagtaca aatttgtaag   1320
atgatgaaag acgcacaata ttaa                                          1344
```

<210> SEQ ID NO 47
<211> LENGTH: 447
<212> TYPE: PRT
<213> ORGANISM: ????(Panax notoginseng)

<400> SEQUENCE: 47

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
    210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285
```

```
Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Val Arg Asp Glu
370                 375                 380

Asn Gly Lys Tyr Thr Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415

Ser Asp Lys Met Lys Glu Lys Gly Glu Gln Glu Ile Gly Arg Ala Val
                420                 425                 430

Glu Glu Leu Val Gln Ile Cys Lys Met Met Lys Asp Ala Gln Tyr
            435                 440                 445

<210> SEQ ID NO 48
<211> LENGTH: 1344
<212> TYPE: DNA
<213> ORGANISM: ????(Panax notoginseng)

<400> SEQUENCE: 48
atggatatcg aaaaaggtag aatcagtata gttatgctgc cattttttagc ccatggtcac      60 atatctccat tctttgagct agccaagcat ctctcaaaaa gaaattgcaa tatattcctc     120
tgttctaccc caatcaatct tagctccatc aagaacagag tatctggtaa ggattcctct     180
gcttctataa aactagtaga gcttcatctt ccatcttccc ctgatcttcc tcctcagtac     240
cacaccacaa atggcctccc ttcccatctc atggtcccac tcaaaaacgc ctttgaaaca     300
gtaggcccca ccttctctga aatccttaaa accttagacc ctgatttgct tatttatgat     360
ttcaatccct catgggcacc ggagatcgct ttgtctcaca atattccggc agtttatttc     420
ctaacctcgg cagcagccac ctcttccgtg gccctacgtg ctttgaaaaa cccaggtgaa     480
aaatacccat ttcagatttt ttatgataac agtaatatta ccccctgaacc accttctgca     540 gataaaatga gctatttca tgattttgtt gcttgtttca aacgatcttg cgacattatt     600
ttgattaaga gttttagaga actagaaggg aaatatattg atttgctttc cactttatct     660
aagaaaactt tggttcctgt tggtccactc gttcaagatc ctttgggaca tgatgaagat     720
ccaaaaacag gcatcttat aaactggctt gacaaaggg ctgaatctac agtggtgttt     780
gtctgctttg aagtgagta ttttccctcc aatgaggaat ggaagaagt agcaattggg     840 ctagagatta gcatggttaa tttcatattg gctgttagat ttcttgaagg agagaaaaaa     900
ggggttttac cagaagggtt tgttcaaagg gtaggagaca gaggattggt tgtggagggg     960
tgggctccac aggcaagaat tttaggacat tcaagcaccg tgggttttgt gagccattgt    1020
gggtggagtt ctattatgga gagtgtgaag tttggggttc cagtaattgc catggccagg    1080
catcttgatc agccctttgaa tgctaagctg gcggcggagg ttggtgtggg catggaggtt    1140
gtgagagatg aaaatgggaa gtatacgaga gaagcgattg cagaggtaat aagaaaagtt    1200
gtgatggaga aaaatgggga ggttatcagg aggaaagcaa gggaattgag tgataaaatg    1260
```
aaagagaaag gagagcaaga gattggtagg gcagtggagg agctagtaca aatttgtaag    1320
atgaagaaag acgcacaata ttaa    1344

<210> SEQ ID NO 49
<211> LENGTH: 447
<212> TYPE: PRT
<213> ORGANISM: ????(Panax notoginseng)

<400> SEQUENCE: 49

Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Gly Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
    210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

| Val | Pro | Val | Ile | Ala | Met | Ala | Arg | His | Leu | Asp | Gln | Pro | Leu | Asn | Ala |
|  |  | 355 |  |  |  | 360 |  |  |  |  | 365 |  |  |  |  |

| Lys | Leu | Ala | Ala | Glu | Val | Gly | Val | Gly | Met | Glu | Val | Val | Arg | Asp | Glu |
| 370 |  |  |  |  | 375 |  |  |  |  | 380 |  |  |  |  |  |

| Asn | Gly | Lys | Tyr | Thr | Arg | Glu | Ala | Ile | Ala | Glu | Val | Ile | Arg | Lys | Val |
| 385 |  |  |  |  | 390 |  |  |  |  | 395 |  |  |  |  | 400 |

| Val | Met | Glu | Lys | Asn | Gly | Glu | Val | Ile | Arg | Arg | Lys | Ala | Arg | Glu | Leu |
|  |  |  |  | 405 |  |  |  |  | 410 |  |  |  |  | 415 |  |

| Ser | Asp | Lys | Met | Lys | Glu | Lys | Gly | Glu | Gln | Glu | Ile | Gly | Arg | Ala | Val |
|  |  |  | 420 |  |  |  | 425 |  |  |  |  | 430 |  |  |  |

| Glu | Glu | Leu | Val | Gln | Ile | Cys | Lys | Met | Lys | Lys | Asp | Ala | Gln | Tyr |
|  |  | 435 |  |  |  |  | 440 |  |  |  |  | 445 |  |  |

<210> SEQ ID NO 50
<211> LENGTH: 1344
<212> TYPE: DNA
<213> ORGANISM: ????(Panax notoginseng)

<400> SEQUENCE: 50

| atggatatcg | aaaaaggtag | aatcagtata | gttatgctgc | cattttttagc | ccatggtcac | 60 |
| atatctccat | tctttgagct | agccaagcat | ctctcaaaaa | gaaattgcaa | tatattcctc | 120 |
| tgttctaccc | caatcaatct | tagctccatc | aagaacagag | tatctgataa | ggattcctct | 180 |
| gcttctataa | aactagtaga | gcttcatctt | ccatcttccc | ctgatcttcc | tcctcagtac | 240 |
| cacaccacaa | atggcctccc | ttcccatctc | atggtcccac | tcaaaaacgc | ctttgaaaca | 300 |
| gtaggcccca | ccttctctga | aatccttaaa | accttagacc | ctgatttgtt | tatttatgat | 360 |
| ttcaatccct | catgggcacc | ggagatcgct | tgtctcaca | atattccggc | agtttatttc | 420 |
| ctaacctcgg | cagcagccac | ctcttccgtg | gccctacgtg | ctttgaaaaa | cccaggtgaa | 480 |
| aaatacccat | ttccagattt | ttatgataac | agtaatatta | ccctgaacc | accttctgca | 540 |
| gataaaatga | gctatttca | tgattttgtt | gcttgtttca | aacgatcttg | cgacattatt | 600 |
| ttgattaaga | gttttagaga | actagaaggg | aaatatattg | atttgctttc | cactttatct | 660 |
| aagaaaactt | tggttcctgt | tggtccactc | gttcaagatc | ctttgggaca | tgatgaagat | 720 |
| ccaaaaacag | ggcatcttat | aaactggctt | gacaaaaggg | ctgaatctac | agtggtgttt | 780 |
| gtctgctttg | aagtgagta | ttttcccctcc | aatgaggaat | tggaagaagt | agcaattggg | 840 |
| ctagagatta | gcatggttaa | tttcatattg | gctgttagat | tcttgaagg | agagaaaaaa | 900 |
| ggggttttac | agaagggtt | tgttcaaagg | gtaggagaca | gaggattggt | tgtgagggg | 960 |
| tgggctccac | aggcaagaat | tttaggacat | tcaagcaccg | gtgggtttgt | gagccattgt | 1020 |
| gggtggagtt | ctattatgga | gagtgtgaag | tttggggttc | cagtaattgc | catggccagg | 1080 |
| catcttgatc | agcctttgaa | tgctaagctg | gcggcggagg | ttggtgtggg | catggaggtt | 1140 |
| gtgagagatg | aaaatgggaa | gtatacgaga | gaagcgattg | cagaggtaat | aagaaaagtt | 1200 |
| gtgatggaga | aaaatgggga | ggttatcagg | aggaaagcaa | gggaattgag | tgataaaatg | 1260 |
| aaagagaaag | gagagcaaga | gattggtagg | gcagtggagg | agctagtaca | aatttgtaag | 1320 |
| atgaagaaag | acgcacaata | ttaa |  |  |  | 1344 |

<210> SEQ ID NO 51
<211> LENGTH: 447
<212> TYPE: PRT
<213> ORGANISM: ????(Panax notoginseng)

<400> SEQUENCE: 51

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Phe Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
    210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Val Arg Asp Glu
    370                 375                 380

Asn Gly Lys Tyr Thr Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415
```

Ser Asp Lys Met Lys Glu Lys Gly Glu Gln Ile Gly Arg Ala Val
            420                 425                 430

Glu Glu Leu Val Gln Ile Cys Lys Met Lys Lys Asp Ala Gln Tyr
        435                 440                 445

<210> SEQ ID NO 52
<211> LENGTH: 1338
<212> TYPE: DNA
<213> ORGANISM: ????(Panax notoginseng)

<400> SEQUENCE: 52

| | | | | | |
|---|---|---|---|---|---|
| atcgagaaag | gtagaatcag | tatagttatg | ctaccatttt | tagcccatgg | tcacatatct | 60 |
| ccattctttg | agctagccaa | gcatctctca | aaaagaaatt | gcaatatatt | cctctgttct | 120 |
| accccaatca | atcttagctc | catcaagaac | agagtatctg | ataaggattc | ctctgcttca | 180 |
| ataaaactag | tagagcttca | tcttccatct | tcccctgatc | ttcctcctca | gtaccacacc | 240 |
| acaaatggcc | tcccttccca | tctcatggtc | ccactcaaaa | acgcctttga | aacagtaggc | 300 |
| cccaccttct | ctgaaatcct | taaaacctta | gaccctgatt | gcttattta | tgatttcaat | 360 |
| ccctcatggg | caccggagat | cgctttgtct | cacaatattc | cggcagttta | tttcctaacc | 420 |
| tcggcagcag | ccacctcttc | cgtggcccta | cgtgctttga | aaaacccagg | tgaaaaatac | 480 |
| ccatttccag | attttatga | taacagtaat | attaccctg | aaccaccttc | tgcagataaa | 540 |
| atgaagctat | tcatgatttt | tgttgcttgt | ttcaaacgat | cttgcgacat | tattttgatt | 600 |
| aagagttttta | gagaactaga | agggaaatat | attgatttgc | tttccacttt | atctaagaaa | 660 |
| actttggttc | ctgttggtcc | actcgttcaa | gatcctttgg | gacatgatga | agatccaaaa | 720 |
| acagggcatc | ttataaactg | gcttgacaaa | agggctgaat | ctacagtggt | gtttgtctgc | 780 |
| tttggaagtg | agtatttttcc | ctccaatgag | gaattggaag | aagtagcaat | tgggctagag | 840 |
| attagcatgg | ttaatttcat | attggctgtg | agatttcttg | aaggagagaa | aaaagggggtt | 900 |
| ttaccagagg | ggtttgttca | aagggtagga | gacagaggat | tggttgtgga | ggggtgggct | 960 |
| ccacaggcaa | gaattttagg | acattcaagc | accggtgggt | ttgtgagcca | ttgtgggtgg | 1020 |
| agttctatta | tggagagtgt | gaagtttggg | gttccagtaa | ttgccatggc | caggcatctt | 1080 |
| gatcagcctt | tgaatgctaa | gctggcggcg | ggggtcggtg | tgggcatgga | ggttgtgaga | 1140 |
| gatgaaaatg | ggaagtataa | gagagaagcg | attgcagagg | taataagaaa | agtcgtgatg | 1200 |
| gagaaaaatg | gggaggttat | caggaggaaa | gcagggaat | tgagtgagaa | aatgaaagag | 1260 |
| acaggagagc | aagagattgg | tagggcagtg | gaggagctag | tacaaatttg | taagatgaag | 1320 |
| aaagacgcac | aatattaa | | | | | 1338 |

<210> SEQ ID NO 53
<211> LENGTH: 447
<212> TYPE: PRT
<213> ORGANISM: ????(Panax notoginseng)

<400> SEQUENCE: 53

Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Gly Val Gly Val Gly Met Glu Val Val Arg Asp Glu
370                 375                 380

Asn Gly Lys Tyr Lys Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415

Ser Glu Lys Met Lys Glu Thr Gly Glu Gln Glu Ile Gly Arg Ala Val
            420                 425                 430

Glu Glu Leu Val Gln Ile Cys Lys Met Lys Lys Asp Ala Gln Tyr
        435                 440                 445

<210> SEQ ID NO 54
<211> LENGTH: 1344
<212> TYPE: DNA
<213> ORGANISM: ????(Panax notoginseng)

<400> SEQUENCE: 54

```
atggatatcg agaaaggtag aatcagtata gttatgctac cattttttagc ccatggtcac      60
atatctccat tccttgagct agccaagcat ctctcaaaaa gaaattgcaa tatattcctc     120
tgttctaccc caatcaatct tagctccatc aagaacagag tatctgataa ggattcctct     180
gcttcaataa aactagtaga gcttcatctt ccatcttccc ctgatcttcc tcctcagtac     240
cacaccacaa atggcctccc ttcccatctc atggtcccac tcaaaaacgc ctttgaaaca     300
gtaggcccca ccttctctga aatccttaaa accttagacc ctgatttgct tatttatgat     360
ttcaatccct catgggcacc ggagatcgct tgtctcaca atattccggc agtttatttc     420
ctaacctcgg cagcagccac ctcttccgtg ccctacgtg ctttgaaaaa cccaggtgaa     480
aaatacccat ttccagattt ttatgataac agtaatatta ccccctgaacc accttctgca    540
gataaaatga agctatttca tgattttgtt gcttgtttca acgatcttg cgacattatt      600
ttgattaaga gttttagaga actagaaggg aaatatattg atttgctttc cactttatct     660
aagaaaactt tggttcctgt tggtccactc gttcaagatc ctttgggaca tgatgaagat     720
ccaaaaacag ggcatcttat aaactggctt gacaaaaggg ctgaatctac agtggtgttt     780
gtctgctttg gaagtgagta ttttccctcc aatgaggaat tggaagaagt agcaattggg    840
ctagagatta gcatggttaa tttcatattg gctgtgagat tcttgaagg agagaaaaaa     900
ggggttttac cagaggggtt tgttcaaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttggggttc cagtaattgc catggccagg  1080
catcttgatc agccttttgaa tgctaagctg gcggcggagg tcggtgtggg catggaggtt   1140
gtgagagatg aaaatgggaa gtataagaga aagcgattg cagaggtaat aagaaaagtc    1200
gtgatggaga aaaatgggga ggttatcagg aggaaagcaa gggaattgag tgagaaaatg   1260
aaagagacag gagagcaaga gattggtagg gcagtggagg agctagtaca aatttgtaag  1320
atgaagaaag acgcacaata ttaa                                          1344
```

<210> SEQ ID NO 55
<211> LENGTH: 447
<212> TYPE: PRT
<213> ORGANISM: ????(Panax notoginseng)

<400> SEQUENCE: 55

```
Met Asp Ile Glu Lys Gly Arg Ile Ser Ile Val Met Leu Pro Phe Leu
1               5                   10                  15

Ala His Gly His Ile Ser Pro Phe Leu Glu Leu Ala Lys His Leu Ser
                20                  25                  30

Lys Arg Asn Cys Asn Ile Phe Leu Cys Ser Thr Pro Ile Asn Leu Ser
            35                  40                  45

Ser Ile Lys Asn Arg Val Ser Asp Lys Asp Ser Ala Ser Ile Lys
        50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125
```

| | | | | | | | | | | | | |
|---|---|---|---|---|---|---|---|---|---|---|---|---|
|Ile|Ala|Leu|Ser|His|Asn|Ile|Pro|Ala|Val|Tyr|Phe|Leu|Thr|Ser|Ala|
| |130| | | |135| | | |140| | | |

Ile Ala Leu Ser His Asn Ile Pro Ala Val Tyr Phe Leu Thr Ser Ala
    130             135            140

Ala Ala Thr Ser Ser Val Ala Leu Arg Ala Leu Lys Asn Pro Gly Glu
145             150            155            160

Lys Tyr Pro Phe Pro Asp Phe Tyr Asp Asn Ser Asn Ile Thr Pro Glu
    165             170            175

Pro Pro Ser Ala Asp Lys Met Lys Leu Phe His Asp Phe Val Ala Cys
        180             185            190

Phe Lys Arg Ser Cys Asp Ile Ile Leu Ile Lys Ser Phe Arg Glu Leu
    195             200            205

Glu Gly Lys Tyr Ile Asp Leu Leu Ser Thr Leu Ser Lys Lys Thr Leu
210             215            220

Val Pro Val Gly Pro Leu Val Gln Asp Pro Leu Gly His Asp Glu Asp
225             230            235            240

Pro Lys Thr Gly His Leu Ile Asn Trp Leu Asp Lys Arg Ala Glu Ser
        245             250            255

Thr Val Val Phe Val Cys Phe Gly Ser Glu Tyr Phe Pro Ser Asn Glu
    260             265            270

Glu Leu Glu Glu Val Ala Ile Gly Leu Glu Ile Ser Met Val Asn Phe
        275             280            285

Ile Leu Ala Val Arg Phe Leu Glu Gly Glu Lys Lys Gly Val Leu Pro
290             295            300

Glu Gly Phe Val Gln Arg Val Gly Asp Arg Gly Leu Val Val Glu Gly
305             310            315            320

Trp Ala Pro Gln Ala Arg Ile Leu Gly His Ser Ser Thr Gly Gly Phe
        325             330            335

Val Ser His Cys Gly Trp Ser Ser Ile Met Glu Ser Val Lys Phe Gly
    340             345            350

Val Pro Val Ile Ala Met Ala Arg His Leu Asp Gln Pro Leu Asn Ala
        355             360            365

Lys Leu Ala Ala Glu Val Gly Val Gly Met Glu Val Val Arg Asp Glu
370             375            380

Asn Gly Lys Tyr Lys Arg Glu Ala Ile Ala Glu Val Ile Arg Lys Val
385             390            395            400

Val Met Glu Lys Asn Gly Glu Val Ile Arg Arg Lys Ala Arg Glu Leu
        405             410            415

Ser Glu Lys Met Lys Glu Thr Gly Val Gln Glu Ile Gly Arg Ala Val
    420             425            430

Glu Glu Leu Val Gln Ile Cys Lys Met Lys Lys Asp Ala Gln Tyr
        435             440            445

<210> SEQ ID NO 56
<211> LENGTH: 1344
<212> TYPE: DNA
<213> ORGANISM: ????(Panax notoginseng)

<400> SEQUENCE: 56
atgtatatcg agaaaggtag aatcagtata gttatgctac cattttttagc ccatggtcac     60 atatctccat tctttgagct agccaagcat ctctcaaaaa gaaattgcaa tatattcctc    120
tgttctaccc caatcaatct tagctccatc aagaacagag tatctgataa ggattcctct    180
gcttcaataa aactagtaga gcttcatctt ccatcttccc ctgatcttcc tcctcagtac    240
cacaccacaa atggcctccc ttcccatctc atggtcccac tcaaaaacgc ctttgaaaca    300

```
gtaggcccca ccttctctga aatccttaaa accttagacc ctgatttgct tatttatgat    360
ttcaatccct catgggcacc ggagatcgct ttgtctcaca atattccggc agtttatttc    420
ctaacctcgg cagcagccac ctcttccgtg gccctacgtg ctttgaaaaa cccaggtgaa    480
aaatacccat ttccagattt ttatgataac agtaatatta ccctgaacc accttctgca     540
gataaaatga agctatttca tgattttgtt gcttgtttca aacgatcttg cgacattatt    600
ttgattaaga gttttagaga actagaaggg aaatatattg atttgctttc cactttatct    660
aagaaaactt tggttcctgt tggtccactc gttcaagatc ctttgggaca tgatgaagat    720
ccaaaaacag ggcatcttat aaactggctt gacaaaaggg ctgaatctac agtggtgttt    780
gtctgctttg gaagtgagta ttttccctcc aatgaggaat ggaagaagt agcaattggg     840
ctagagatta gcatggttaa tttcatattg gctgtgagat ttcttgaagg agagaaaaaa    900
ggggttttac cagagggtt tgttcaaagg gtaggagaca gaggattggt tgtggagggg     960
tgggctccac aggcaagaat tttaggacat tcaagcaccg gtgggtttgt gagccattgt   1020
gggtggagtt ctattatgga gagtgtgaag tttggggttc cagtaattgc catggccagg   1080
catcttgatc agcctttgaa tgctaagctg gcggcggagg tcggtgtggg catggaggtt   1140
gtgagagatg aaaatgggaa gtaagagaga aagcgattg cagaggtaat aagaaaagtc    1200
gtgatggaga aaatgggga ggttatcagg aggaaagcaa gggaattgag tgagaaaatg     1260
aaagagacag gagagcaaga gattggtagg gcagtggagg agctagtaca aatttgtaag   1320
atgaagaaag acgcacaata ttaa                                          1344
```

<210> SEQ ID NO 57
<211> LENGTH: 447
<212> TYPE: PRT
<213> ORGANISM: ????(Panax notoginseng)

<400> SEQUENCE: 57

Met Tyr Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
                20                  25                  30

Lys Arg Asn Cys Asn Ile Phe Leu Cys Ser Thr Pro Ile Asn Leu Ser
            35                  40                  45

Ser Ile Lys Asn Arg Val Ser Asp Lys Asp Ser Ala Ser Ile Lys
        50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
                100                 105                 110

Asp Pro Asp Leu Leu Ile Tyr Asp Phe Asn Pro Ser Trp Ala Pro Glu
            115                 120                 125

Ile Ala Leu Ser His Asn Ile Pro Ala Val Tyr Phe Leu Thr Ser Ala
        130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
                180                 185                 190

```
Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Lys Thr Leu
210                 215                 220

Val Pro Val Gly Pro Leu Val Gln Asp Pro Leu Gly His Asp Glu Asp
225                 230                 235                 240

Pro Lys Thr Gly His Leu Ile Asn Trp Leu Asp Lys Arg Ala Glu Ser
            245                 250                 255

Thr Val Val Phe Val Cys Phe Gly Ser Glu Tyr Phe Pro Ser Asn Glu
                260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
                340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Val Arg Asp Glu
    370                 375                 380

Asn Gly Lys Tyr Lys Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415

Ser Glu Lys Met Lys Glu Thr Gly Glu Gln Glu Ile Gly Arg Ala Val
                420                 425                 430

Glu Glu Leu Val Gln Ile Cys Lys Met Lys Lys Asp Ala Gln Tyr
        435                 440                 445

<210> SEQ ID NO 58
<211> LENGTH: 1344
<212> TYPE: DNA
<213> ORGANISM: ????(Panax notoginseng)

<400> SEQUENCE: 58
atggatatcg aaaaaggtag aatcagtata gttatgctgc cattttttagc ccatggtcac    60 atatctccat tctttgagct agccaagcat ctctcaaaaa gaaattgcaa tatattcctc   120
tgttctaccc caatcaatct tagctccatc aagaacagag tatctgataa ggattcctct   180
gcttctataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca ccttctctga atccttaaaa accttagacc ctgatttgct tatttatgat   360
ttcaatccct catgggcacc ggagatcgct ttgtctcaca atattccggc agtttatttc   420
ctaacctcgg cagcagccac ctcttccgtg gccctacgtg ctttgaaaaa cccaggtgaa   480
aaatacccat tccagatttt tatgataaac agtaatatta cccctgaacc accttctgca   540
gataaaatga agctatttca tgattttgtt gcttgtttca aacgatcttg cgacattatt   600
ttgattaaga gttttagaga actagaaggg aaatatattg atttgctttc cactttatct   660
```

```
aagaaaactt tggttcctgt tggtccactc gttcaagatc atttgggaca tgatgaagat    720
ccaaaaacag ggcatcttat aaactggctt gacaaaaggg ctgaatctac agtggtgttt    780
gtctgctttg aagtgagta ttttccctcc aatgaggaat tggaagaagt agcaattggg    840
ctagagatta gcatggttaa tttcatattg gctgttagat ttcttgaagg agagaaaaaa    900
ggggttttac cagaagggtt tgttcaaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttggggttc cagtaattgc catggccagg   1080
catcttgatc agcctttgaa tgctaagctg gcggcggagg ttggtgtggg catggaggtt   1140
gtgagagatg aaaatgggaa gtatacgaga gaagcgattg cagaggtaat aagaaaagtt   1200
gtgatggaga aaaatgggga ggttatcagg aggaaagcaa gggaattgag tgataaaatg   1260
aaagagaaag gagagcaaga gattggtagg gcagtggagg agctagtaca aatttgtaag   1320
atgaagaaag acgcacaata ttaa                                          1344
```

<210> SEQ ID NO 59
<211> LENGTH: 447
<212> TYPE: PRT
<213> ORGANISM: ????(Panax notoginseng)

<400> SEQUENCE: 59

Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ala Ser Ile Lys
    50                  55                  60

Leu Val Glu Leu His Leu Pro Ser Ser Pro Asp Leu Pro Pro Gln Tyr
65                  70                  75                  80

His Thr Thr Asn Gly Leu Pro Ser His Leu Met Val Pro Leu Lys Asn
                85                  90                  95

Ala Phe Glu Thr Val Gly Pro Thr Phe Ser Glu Ile Leu Lys Thr Leu
            100                 105                 110

Asp Pro Asp Leu Leu Ile Tyr Asp Phe Asn Pro Ser Trp Ala Pro Glu
        115                 120                 125

Ile Ala Leu Ser His Asn Ile Pro Ala Val Tyr Phe Leu Thr Ser Ala
    130                 135                 140

Ala Ala Thr Ser Ser Val Ala Leu Arg Ala Leu Lys Asn Pro Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Lys Thr Leu
    210                 215                 220

Val Pro Val Gly Pro Leu Val Gln Asp His Leu Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Val Ala Ile Gly Leu Glu Ile Ser Met Val Asn Phe
        275                 280                 285

Ile Leu Ala Val Arg Phe Leu Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Val Arg Asp Glu
    370                 375                 380

Asn Gly Lys Tyr Thr Arg Glu Ala Ile Ala Glu Val Ile Arg Lys Val
385                 390                 395                 400

Val Met Glu Lys Asn Gly Glu Val Ile Arg Arg Lys Ala Arg Glu Leu
                405                 410                 415

Ser Asp Lys Met Lys Glu Lys Gly Glu Gln Glu Ile Gly Arg Ala Val
            420                 425                 430

Glu Glu Leu Val Gln Ile Cys Lys Met Lys Lys Asp Ala Gln Tyr
        435                 440                 445

<210> SEQ ID NO 60
<211> LENGTH: 41
<212> TYPE: DNA
<213> ORGANISM: artificial sequence
<220> FEATURE:
<223> OTHER INFORMATION: primer

<400> SEQUENCE: 60
taagaaggag atataccatg gatatcgaaa aaggtagaat c                41

<210> SEQ ID NO 61
<211> LENGTH: 44
<212> TYPE: DNA
<213> ORGANISM: artificial sequence
<220> FEATURE:
<223> OTHER INFORMATION: primer

<400> SEQUENCE: 61
tgcggccgca agcttgtcga catattgtgc gtctttcttc atct            44

<210> SEQ ID NO 62
<211> LENGTH: 46
<212> TYPE: DNA
<213> ORGANISM: artificial sequence
<220> FEATURE:
<223> OTHER INFORMATION: primer

<400> SEQUENCE: 62
taagaaggag atataccatg ggtgataacc aaaaaggtag aatcag          46

<210> SEQ ID NO 63
<211> LENGTH: 44
<212> TYPE: DNA
<213> ORGANISM: artificial sequence
<220> FEATURE:

<223> OTHER INFORMATION: primer

<400> SEQUENCE: 63
tgcggccgca agcttgtcga cttgtgcatc tttcttcttc ttac         44

<210> SEQ ID NO 64
<211> LENGTH: 45
<212> TYPE: DNA
<213> ORGANISM: artificial sequence
<220> FEATURE:
<223> OTHER INFORMATION: primer

<400> SEQUENCE: 64
taagaaggag ataccatg ggtgatatcg agaaaggtag aatca         45

<210> SEQ ID NO 65
<211> LENGTH: 41
<212> TYPE: DNA
<213> ORGANISM: artificial sequence
<220> FEATURE:
<223> OTHER INFORMATION: primer

<400> SEQUENCE: 65
tgcggccgca agcttgtcga catattgtgc gtctttcttc a         41

<210> SEQ ID NO 66
<211> LENGTH: 45
<212> TYPE: DNA
<213> ORGANISM: artificial sequence
<220> FEATURE:
<223> OTHER INFORMATION: primer

<400> SEQUENCE: 66
taagaaggag ataccatg ggtgatatcg aaaaaggtag aatca         45

<210> SEQ ID NO 67
<211> LENGTH: 41
<212> TYPE: DNA
<213> ORGANISM: artificial sequence
<220> FEATURE:
<223> OTHER INFORMATION: primer

<400> SEQUENCE: 67
tgcggccgca agcttgtcga catattgtgc gtctttcttc a         41

<210> SEQ ID NO 68
<211> LENGTH: 45
<212> TYPE: DNA
<213> ORGANISM: artificial sequence
<220> FEATURE:
<223> OTHER INFORMATION: primer

<400> SEQUENCE: 68
taagaaggag ataccatg ggtgatatcg aaaaaggtag aatca         45

<210> SEQ ID NO 69
<211> LENGTH: 42
<212> TYPE: DNA
<213> ORGANISM: artificial sequence
<220> FEATURE:
<223> OTHER INFORMATION: primer

<400> SEQUENCE: 69
tgcggccgca agcttgtcga catattgtgc gtctttcatc at         42

```
<210> SEQ ID NO 70
<211> LENGTH: 47
<212> TYPE: DNA
<213> ORGANISM: artificial sequence
<220> FEATURE:
<223> OTHER INFORMATION: primer

<400> SEQUENCE: 70
taagaaggag ataccatg ggtgatatcg aaaaaggtag aatcagt          47

<210> SEQ ID NO 71
<211> LENGTH: 44
<212> TYPE: DNA
<213> ORGANISM: artificial sequence
<220> FEATURE:
<223> OTHER INFORMATION: primer

<400> SEQUENCE: 71
gtgcggccgc aagcttgtcg acatattgtg cgtctttctt catc          44

<210> SEQ ID NO 72
<211> LENGTH: 46
<212> TYPE: DNA
<213> ORGANISM: artificial sequence
<220> FEATURE:
<223> OTHER INFORMATION: primer

<400> SEQUENCE: 72
taagaaggag ataccatg ggtgatatcg aaaaaggtag aatcag           46

<210> SEQ ID NO 73
<211> LENGTH: 43
<212> TYPE: DNA
<213> ORGANISM: artificial sequence
<220> FEATURE:
<223> OTHER INFORMATION: primer

<400> SEQUENCE: 73
gtgcggccgc aagcttgtcg acatattgtg cgtctttctt cat           43

<210> SEQ ID NO 74
<211> LENGTH: 44
<212> TYPE: DNA
<213> ORGANISM: artificial sequence
<220> FEATURE:
<223> OTHER INFORMATION: primer

<400> SEQUENCE: 74
taagaaggag ataccatg ggtgatatcg agaaaggtag aatc            44

<210> SEQ ID NO 75
<211> LENGTH: 42
<212> TYPE: DNA
<213> ORGANISM: artificial sequence
<220> FEATURE:
<223> OTHER INFORMATION: primer

<400> SEQUENCE: 75
gtgcggccgc aagcttgtcg acatattgtg cgtctttctt ca            42

<210> SEQ ID NO 76
<211> LENGTH: 44
<212> TYPE: DNA
<213> ORGANISM: artificial sequence
<220> FEATURE:
<223> OTHER INFORMATION: primer
```

<400> SEQUENCE: 76
taagaaggag ataccatg ggtgatatcg agaaaggtag aatc                44

<210> SEQ ID NO 77
<211> LENGTH: 42
<212> TYPE: DNA
<213> ORGANISM: artificial sequence
<220> FEATURE:
<223> OTHER INFORMATION: primer

<400> SEQUENCE: 77
gtgcggccgc aagcttgtcg acatattgtg cgtctttctt ca                42

<210> SEQ ID NO 78
<211> LENGTH: 38
<212> TYPE: DNA
<213> ORGANISM: artificial sequence
<220> FEATURE:
<223> OTHER INFORMATION: primer

<400> SEQUENCE: 78
taagaaggag ataccatg tatatcgaga aaggtaga                       38

<210> SEQ ID NO 79
<211> LENGTH: 41
<212> TYPE: DNA
<213> ORGANISM: artificial sequence
<220> FEATURE:
<223> OTHER INFORMATION: primer

<400> SEQUENCE: 79
tgcggccgca agcttgtcga catattgtgc gtctttcttc a                 41

<210> SEQ ID NO 80
<211> LENGTH: 40
<212> TYPE: DNA
<213> ORGANISM: artificial sequence
<220> FEATURE:
<223> OTHER INFORMATION: primer

<400> SEQUENCE: 80
taagaaggag ataccatg gatatcgaaa aaggtagaat                     40

<210> SEQ ID NO 81
<211> LENGTH: 45
<212> TYPE: DNA
<213> ORGANISM: artificial sequence
<220> FEATURE:
<223> OTHER INFORMATION: primer

<400> SEQUENCE: 81
tgcggccgca agcttgtcga catattgtgc gtctttcttc atctt             45

<210> SEQ ID NO 82
<211> LENGTH: 22
<212> TYPE: DNA
<213> ORGANISM: artificial sequence
<220> FEATURE:
<223> OTHER INFORMATION: primer

<400> SEQUENCE: 82
agagttcatt catggataac ca                                      22

<210> SEQ ID NO 83
<211> LENGTH: 22

```
<212> TYPE: DNA
<213> ORGANISM: artificial sequence
<220> FEATURE:
<223> OTHER INFORMATION: primer

<400> SEQUENCE: 83
ttaagcgcat tcaaaaatat tc                                              22

<210> SEQ ID NO 84
<211> LENGTH: 21
<212> TYPE: DNA
<213> ORGANISM: artificial sequence
<220> FEATURE:
<223> OTHER INFORMATION: primer

<400> SEQUENCE: 84
agagttcatc atggatatcg a                                               21

<210> SEQ ID NO 85
<211> LENGTH: 22
<212> TYPE: DNA
<213> ORGANISM: artificial sequence
<220> FEATURE:
<223> OTHER INFORMATION: primer

<400> SEQUENCE: 85
catagctcat tcaaaatgac tc                                              22

<210> SEQ ID NO 86
<211> LENGTH: 21
<212> TYPE: DNA
<213> ORGANISM: artificial sequence
<220> FEATURE:
<223> OTHER INFORMATION: primer

<400> SEQUENCE: 86
catagctcat tcaaaatgaa t                                               21

<210> SEQ ID NO 87
<211> LENGTH: 34
<212> TYPE: DNA
<213> ORGANISM: artificial sequence
<220> FEATURE:
<223> OTHER INFORMATION: primer

<400> SEQUENCE: 87
tatctatcgt atacgccaga gttcatcatg gata                                 34

<210> SEQ ID NO 88
<211> LENGTH: 35
<212> TYPE: DNA
<213> ORGANISM: artificial sequence
<220> FEATURE:
<223> OTHER INFORMATION: primer

<400> SEQUENCE: 88
tgcagtcgag atacatctag catacaaaga aagag                                35

<210> SEQ ID NO 89
<211> LENGTH: 1329
<212> TYPE: DNA
<213> ORGANISM: Panax ginseng

<400> SEQUENCE: 89
atggataacc aaaaaggtag aatcagtata gcgttgctac cattttttagc ccatggtcac    60
```

```
atatctccct tctttgagct agccaaacaa ctcgcgaaaa gaaattgcaa tgttttcctc        120
tgttctaccc caatcaatct tagctccatc aaggataagg attcctctgc ttctataaaa        180
ctagttgagc ttcatcttcc atcttcccct gatcttcctc ctcactatca caccacaaat        240
ggcctccctt cccatctcat gctcccactc agaaacgcct ttgaaactgc aggccccacc        300
ttctctgaaa tccttaaaac cttaaacccc gatttgctta tttatgattt caatccctca        360
tgggcaccgg agatcgcttc gtctcacaat attccggcag tttatttcct aaccacggca        420
gcagccagct cttccattgg cctacatgct ttcaaaaacc caggtgaaaa atacccattt        480
ccagattttt atgataacag taatattacc cctgaaccac cttctgcaga taacatgaag        540
ctacttcatg attttatcgc ttgtttcgaa cgatcttgcg acattatttt gattaagagt        600
tttagagaac tagaagggaa atatattgat ttgctttcca ctttatctga taaaactttg        660
gttcctgttg gtccactcgt tcaagatcct atgggccata atgaagatcc aaaaacagag        720
cagattataa actggcttga caaagggct gaatctacag tggtgtttgt ctgctttgga        780
agtgagtatt ttctctccaa tgaggaattg gaagaagtag caattgggct agagattagc        840
atggttaatt tcatatgggc tgtgagatta attgaaggag agaaaaaagg ggttttacca        900
gagggatttg ttcaaagggt aggagacaga ggattggttg tggaggggtg ggctccacag        960
gcaagaattt taggacattc aagcaccggt gggtttgtga gccattgtgg gtggagttct        1020
attgcggaga gtatgaagtt tggggttcca gtaattgcca tggccaggca tcttgatcag        1080
cctttgaatg gtaagctggc ggcggaggtt ggtgtgggca tggaggttgt gagagatgaa        1140
aatgggaagt ataagagaga agggattgca gaggtaataa gaaagtcgt tgtggagaaa        1200 agtggggagg ttatgaggag gaaagcaagg gaattgagtg agaaaatgaa agagaaagga        1260
gaggaagaga ttgatagggc agtggaggag ctagtacaaa tttgtaagaa gaagaaagat        1320
gcacaatag                                                              1329
```

<210> SEQ ID NO 90
<211> LENGTH: 442
<212> TYPE: PRT
<213> ORGANISM: Panax ginseng

<400> SEQUENCE: 90

```
Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asp Lys Asp Ser Ser Ala Ser Ile Lys Leu Val Glu Leu
        50                  55                  60

His Leu Pro Ser Pro Asp Leu Pro His Tyr His Thr Thr Asn
65                  70                  75                  80

Gly Leu Pro Ser His Leu Met Leu Pro Leu Arg Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ala Ser Ser
        130                 135                 140
```

```
Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
        275                 280                 285

Arg Leu Ile Glu Gly Glu Lys Lys Gly Val Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
        355                 360                 365

Glu Val Gly Val Gly Met Glu Val Val Arg Asp Glu Asn Gly Lys Tyr
    370                 375                 380

Lys Arg Glu Gly Ile Ala Glu Val Ile Arg Lys Val Val Val Glu Lys
385                 390                 395                 400

Ser Gly Glu Val Met Arg Arg Lys Ala Arg Glu Leu Ser Glu Lys Met
                405                 410                 415

Lys Glu Lys Gly Glu Glu Ile Asp Arg Ala Val Glu Glu Leu Val
            420                 425                 430

Gln Ile Cys Lys Lys Lys Lys Asp Ala Gln
        435                 440
```

<210> SEQ ID NO 91
<211> LENGTH: 1329
<212> TYPE: DNA
<213> ORGANISM: Panax ginseng

<400> SEQUENCE: 91

```
atggataacc aagaaggtag aatcagtata gcgttgctac catttttagc ccatggtcac    60
atatctccct tctttgagct agccaaacaa ctcgcaaaaa gaaattgcaa tgttttcctc   120
tgttctaccc caatcaatct tagctccatc aagaataagg attcctctgc ttctataaaa   180
ctagttgagc ttcatcttcc atcttcccct gatcttcctc ctcactatca caccacaaat   240
ggcctccctt cccatctcat ggtcccactc ataaacgcct tgaaacagc aggccccacc    300 ttctctgaaa tccttaaaac cttaaacccc gattgctta tttatgattt caatccctca    360
tgggcaccgg agatcgcttc gtctcacaat attccggcag tttatttcct aaccacggca   420
```

```
gcagccagct cttccattgg cctacatgct ttcaaaaacc caggtgaaaa atacccattt    480 ccagatttttt atgataacag taatattacc cctgaaccac cttctgcaga taacatgaag   540
```

```
gcagccagct cttccattgg cctacatgct ttcaaaaacc caggtgaaaa atacccattt    480
ccagattttt atgataacag taatattacc cctgaaccac cttctgcaga taacatgaag    540
ctacttcatg attttatcgc ttgtttcgaa cgatcttgcg acattatttt gattaagagt    600
tttagagaac tagaagggaa atatattgat ttgctttcca ctttatctga taaaactttg    660
gttcctgttg gtccactcgt tcaagatcct atgggccata atgaagatcc aaaaacagag    720
cagattataa actggcttga caaaagggct gaatctacag tggtgttttgt ctgctttgga   780
agtgagtatt ttctctccaa tgaggaattg gaagaagtag caattgggct agagattagc    840
acggttaatt tcatatgggc tgtgagatta attgaaggag agaaaaaagg gatttttacca  900
gagggggtttg ttcaaagggt aggagacaga ggattggttg tggaggggtg ggctccacag   960
gcaagaattt taggacattc aagcaccggt gggtttgtga ccattgtgg gtggagttct    1020
attgcggaga gtatgaagtt tggggttcca gtaattgcca tggccaggca tcttgatcag   1080
cctttgaatg gtaagctggc ggcggaggtt ggtgtgggca tggaggttgt gagagatgag   1140
aatgggaagt ataagagaga agggattgca gaggtaataa gaaaagtggt tgtggagaaa   1200
agtgggagg ttatcaggag gaaagcaagg gagttgagtg agaaaatgaa agagaaagga   1260
gagcaagaga ttgataggggc attggaggag ctagtacaaa tttgtaagaa gaagaaagat  1320
gaacaatag                                                           1329
```

<210> SEQ ID NO 92
<211> LENGTH: 442
<212> TYPE: PRT
<213> ORGANISM: Panax ginseng

<400> SEQUENCE: 92

```
Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asn Lys Asp Ser Ser Ala Ser Ile Lys Leu Val Glu Leu
        50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Ile Asn Ala Phe Glu Thr
                85                  90                  95

Ala Gly Pro Thr Phe Ser Glu Ile Leu Lys Thr Leu Asn Pro Asp Leu
                100                 105                 110

Leu Ile Tyr Asp Phe Asn Pro Ser Trp Ala Pro Glu Ile Ala Ser Ser
            115                 120                 125

His Asn Ile Pro Ala Val Tyr Phe Leu Thr Thr Ala Ala Ala Ser Ser
        130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
                180                 185                 190

Cys Asp Ile Ile Leu Ile Lys Ser Phe Arg Glu Leu Glu Gly Lys Tyr
            195                 200                 205
```

```
Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
            275                 280                 285

Arg Leu Ile Glu Gly Glu Lys Lys Gly Ile Leu Pro Glu Gly Phe Val
290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
            355                 360                 365

Glu Val Gly Val Gly Met Glu Val Val Arg Asp Glu Asn Gly Lys Tyr
370                 375                 380

Lys Arg Glu Gly Ile Ala Glu Val Ile Arg Lys Val Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Leu Glu Glu Leu Val
            420                 425                 430

Gln Ile Cys Lys Lys Lys Lys Asp Glu Gln
            435                 440

<210> SEQ ID NO 93
<211> LENGTH: 1332
<212> TYPE: DNA
<213> ORGANISM: Panax ginseng

<400> SEQUENCE: 93
atggataacc aagaaggtag aatcagtata gcgttgctac cattttttagc ccatggtcac      60 atatctccct tctttgagct agccaaacaa ctcgcaaaaa gaaattgcaa tgttttcctc     120
tgttctaccc caatcaatct tagctccatc aagaataagg attcctctgc ttctataaaa     180
ctagttgagc ttcatcttcc atcttccccct gatcttcctc ctcactatca caccacaaat     240
ggcctccctt cccatctcat ggtcccactc ataaacgcct tgaaacagc aggccccacc      300 ttctctgaaa tccttaaaac cttaaacccc gatttgctta tttatgattt caatccctca     360
tgggcaccgg agatcgcttc gtctcacaat attccggcag tttatttcct aaccacggca     420
gcagccagct cttccattgg cctacatgct ttcaaaaacc caggtgaaaa atacccattt     480
ccagattttt atgataacag taataatacc cctgaaccac ttctgcaga taacatgaag     540 ctacttcatg attttatcgc ttgtttcgaa cgatcttgcg acattatttt gattaagagt     600
tttatagaac tagaagggaa atatatcgat ttgctttcca ctttatctga taaaactttg     660
gttcctgttg gtccactcgt tcaagatcct atgggccata tgaagatcc aaaaacagag     720 cagattataa actggcttga caaaagggct gaatctacag tggtgtttgt ctgcttttgga    780
```

```
agtgagtatt ttctctccaa tgaggaattg gaagaagtag caattgggct agagattagc    840
atggttaatt tcatatgggc tgtgagatta attgaaggag agaaaaaagg ggttttacca    900
gagggatttg ttcaaagggt aggagacaga ggattggttg tggaggggtg ggctccacag    960
gcaagaattt taggacattc aagcaccggt gggtttgtga gccattgtgg gtggagttct   1020
attatggaga gtgtgaagtt tggggttcca gtaattgcca tggccaggca tcttgatcag   1080
cctttgaatg ctaagctggc ggcggaggtt ggtgtgggca tggaggttat gagagatgaa   1140
aatgggaagt ataagagaga agcgattgca gaggtaataa gaaaagtcgt gatggagaaa   1200
aatggggagg ttatgaggag gaaagcaagg gaattgagtg agaaaatgaa agtgaaagga   1260
gagcaagaga ttggtagggc ggtggaggag ctagtacaaa tttgtaagaa gaagaagcag   1320
cacgcacaat at                                                      1332
```

<210> SEQ ID NO 94
<211> LENGTH: 444
<212> TYPE: PRT
<213> ORGANISM: Panax ginseng
<400> SEQUENCE: 94

```
Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asn Lys Asp Ser Ala Ser Ile Lys Leu Val Glu Leu
    50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Ile Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Asn Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Ile Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270
```

Val Ala Ile Gly Leu Glu Ile Ser Met Val Asn Phe Ile Trp Ala Val
            275                 280                 285

Arg Leu Ile Glu Gly Gly Lys Lys Gly Val Leu Pro Glu Gly Phe Val
        290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Met Glu Ser Val Lys Phe Gly Val Pro Val Ile
                340                 345                 350

Ala Met Ala Arg His Leu Asp Gln Pro Leu Asn Ala Lys Leu Ala Ala
            355                 360                 365

Glu Val Gly Val Gly Met Glu Val Met Arg Asp Glu Asn Gly Lys Tyr
        370                 375                 380

Lys Arg Glu Ala Ile Ala Glu Val Ile Arg Lys Val Val Met Glu Lys
385                 390                 395                 400

Asn Gly Glu Val Met Arg Arg Lys Ala Arg Glu Leu Ser Glu Lys Met
                405                 410                 415

Lys Val Lys Gly Glu Gln Glu Ile Gly Arg Ala Val Glu Glu Leu Val
                420                 425                 430

Gln Ile Cys Lys Lys Lys Gln His Ala Gln Tyr
            435                 440

<210> SEQ ID NO 95
<211> LENGTH: 1329
<212> TYPE: DNA
<213> ORGANISM: Panax ginseng

<400> SEQUENCE: 95
atggataacc aaaaaggtag aatcagtata gcgttgctac cattttttagc ccatggtcac        60 atatctccct tctttgagct agccaaacaa ctcgcgaaaa gaaattgcaa tgttttcctc       120
tgttctaccc caatcaatct tagctccatc aaggataagg attcctctgc ttctataaaa       180
ctagttgagc ttcatcttcc atcttcccct gatcttcctc ctcactatca caccacaaat       240
ggcctcccct tccatctcat gctcccactc agaaacgcct ttgaaactgc aggccccacc       300
ttctctgaaa tccttaaaac cttaaacccc gatttgctta tttatgattt caatccctca       360
tgggcaccgg agatcgcttc gtctcacaat attccggcag tttatttcct aaccacggca       420
gcagccagct cttccattgg cctacatgct ttcaaaaacc caggtgaaaa atacccattt       480
ccagattttt atgataacag taatattacc cctgaaccac ttctgcaga taacatgaag       540 ctacttcatg atttatcgc ttgtttcgaa cgatcttgcg acattatttt gattaagagt       600
tttagagaac tagaagggaa atatattgat ttgctttcca cttttatctga taaaactttg       660 gttcctgttg gtccactcgt tcaagatcct atgggccata tgaagatcc aaaaacagag       720 cagattataa actggcttga caaaatggct gaatctacag tggtgtttgt ctgctttgga       780
agtgagtatt ttctctccaa tgaggaattg aagaagtag caattgggct agagattagc       840
acggttaatt tcatatgggc tgtgagatta attgaaggag agaaaaaagg gattttacca       900
gaggggtttg ttcaaagggt aggagacaga ggattggttg tggaggggtg gctccacag       960 gcaagaattt taggacattc aagcaccggt gggtttgtga gccattgtgg gtggagttct      1020
attgcggaga gtatgaagtt tggggttcca gtaattgcca tggccaggca tcttgatcag      1080
cctttgaatg gtaagctggc ggcggaggtt ggtgtgggca tggaggttgt gagagatgag      1140

```
aatgggaagt ataagagaga agggattgca gaggtaataa gaaaagtggt tgtggagaaa    1200 agtgggagg ttatcaggag gaaagcaagg gagttgagtg agaaaatgaa agagaaagga    1260
gagcaagaga ttgatagggc attggaggag ctagtacaaa tttgtaagaa gaagaaagat    1320
gaacaatag                                                             1329

<210> SEQ ID NO 96
<211> LENGTH: 442
<212> TYPE: PRT
<213> ORGANISM: Panax ginseng

<400> SEQUENCE: 96

Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asp Lys Asp Ser Ser Ala Ser Ile Lys Leu Val Glu Leu
    50                  55                  60

His Leu Pro Ser Pro Asp Leu Pro His Tyr His Thr Thr Asn
65                  70                  75                  80

Gly Leu Pro Ser His Leu Met Leu Pro Leu Arg Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Met Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
        275                 280                 285

Arg Leu Ile Glu Gly Glu Lys Lys Gly Ile Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335
```

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
            355                 360                 365

Glu Val Gly Val Gly Met Glu Val Val Arg Asp Glu Asn Gly Lys Tyr
        370                 375                 380

Lys Arg Glu Gly Ile Ala Glu Val Ile Arg Lys Val Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Leu Glu Glu Leu Val
            420                 425                 430

Gln Ile Cys Lys Lys Lys Lys Asp Glu Gln
            435                 440

<210> SEQ ID NO 97
<211> LENGTH: 1347
<212> TYPE: DNA
<213> ORGANISM: Panax ginseng

<400> SEQUENCE: 97

```
atggatatcg aaaaaggtag aatcagtata gttatgctgc cattttttagc ccatggccac      60 atttctccat tctttgagct agccaagcat ctctcaaaaa gaaattgtaa tatattcctc     120
tgttctaccc caatcaatct tagctccatc aagaacagag tatctgataa ggattcctct     180
gcttctataa aactagtaga gcttcatctt ccctcttccc ctgatcttcc ccctcactac     240
cacaccacaa atggcctccc ttcccatctc atggtcccac tcagaaacgc ctttgaaaca     300
gcagccccca ccttctctga aatccttaaa accttaaacc ctgatttgct tatttatgat     360
ttcaatccct catgggcacc ggaaatcgct tcgtctcaca atattccggc agtttatttc     420
ctaacctcgg cagcagccac ctcttccatg ggcctacatg ctttcaaaaa ctcaggtgaa     480
aaatacccat ttccagattt ttatgataac agtaatatta cccctgaacc accttctgca     540
gataaaatga gctatttca tgattttgtc gcttgtttca acgatcttg cgacattatt      600 ttgattaaga gttttagaga actggaaggg aaatatattg attttctttc cactttatct     660
aagaaaactt tggttcctgt tggtccactc gttcaagatc ctatgggaca tgatgaagat     720
ccaaaaacag gcatcttat aaactggctt gacaagaggg ctgaatctac agtggtgttt     780
gtctgctttg gaagtgagta ttttccctcc aatgaggaat tggaagaatt agcaattggg     840
ctagagatta gcatggttag tttcatattg gctgtgagat ttcctgaagg agagaaaaaa     900 gggatttta cagaggggtt tgttcaaagg gtaggagaca gaggattggt tgtggagggg     960
tgggctccac aggcaagaat tttaggacat tcaagcaccg tgggtttgt gagccattgt    1020 gggtggagtt ctattatgga gagtgtgaag tttgggggttc cagtaattgc catggccagg    1080
catcttgatc agcctttgaa tgctaagctg cggcggagg ttggtgtggg catggaggtt    1140
atgagagatg aaaatgggaa gtataagaga gaagcgattg cagaggtaat aagaaaagtc    1200
gtgatggaga aaaatgggga ggttatgagg aggaaagcaa gggaattgag tgagaaaatg    1260
aaagtgaaag gagagcaaga gattggtagg gcggtggagg agctagtaca aatttgtaag    1320
aagaagaagc agcacgcaca atattaa                                        1347
```

<210> SEQ ID NO 98
<211> LENGTH: 448
<212> TYPE: PRT

<213> ORGANISM: Panax ginseng

<400> SEQUENCE: 98

```
Met Asp Ile Glu Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Val Ser Asp Lys Asp Ser Ser Ala Ser Ile Lys
    50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Val Pro Leu Arg Asn
                85                  90                  95

Ala Phe Glu Thr Ala Ala Pro Thr Phe Ser Glu Ile Leu Lys Thr Leu
            100                 105                 110

Asn Pro Asp Leu Leu Ile Tyr Asp Phe Asn Pro Ser Trp Ala Pro Glu
        115                 120                 125

Ile Ala Ser Ser His Asn Ile Pro Ala Val Tyr Phe Leu Thr Ser Ala
    130                 135                 140

Ala Ala Thr Ser Ser Met Gly Leu His Ala Phe Lys Asn Ser Gly Glu
145                 150                 155                 160

Lys Tyr Pro Phe Pro Asp Phe Tyr Asp Asn Ser Asn Ile Thr Pro Glu
                165                 170                 175

Pro Pro Ser Ala Asp Lys Met Lys Leu Phe His Asp Phe Val Ala Cys
            180                 185                 190

Phe Lys Arg Ser Cys Asp Ile Ile Leu Ile Lys Ser Phe Arg Glu Leu
        195                 200                 205

Glu Gly Lys Tyr Ile Asp Phe Leu Ser Thr Leu Ser Lys Lys Thr Leu
    210                 215                 220

Val Pro Val Gly Pro Leu Val Gln Asp Pro Met Gly His Asp Glu Asp
225                 230                 235                 240

Pro Lys Thr Gly His Leu Ile Asn Trp Leu Asp Lys Arg Ala Glu Ser
                245                 250                 255

Thr Val Val Phe Val Cys Phe Gly Ser Glu Tyr Phe Pro Ser Asn Glu
            260                 265                 270

Glu Leu Glu Glu Leu Ala Ile Gly Leu Glu Ile Ser Met Val Ser Phe
        275                 280                 285

Ile Leu Ala Val Arg Phe Pro Glu Gly Leu Lys Lys Gly Ile Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Met Glu Ser Val Lys Phe Gly
            340                 345                 350

Val Pro Val Ile Ala Met Ala Arg His Leu Asp Gln Pro Leu Asn Ala
        355                 360                 365

Lys Leu Ala Ala Glu Val Gly Val Gly Met Glu Val Met Arg Asp Glu
    370                 375                 380

Asn Gly Lys Tyr Lys Arg Glu Ala Ile Ala Glu Val Ile Arg Lys Val
385                 390                 395                 400
```

```
        Val Met Glu Lys Asn Gly Glu Val Met Arg Lys Ala Arg Glu Leu
                        405                 410                 415

Ser Glu Lys Met Lys Val Lys Gly Glu Gln Glu Ile Gly Arg Ala Val
                    420                 425                 430

Glu Glu Leu Val Gln Ile Cys Lys Lys Lys Gln His Ala Gln Tyr
                    435                 440                 445

<210> SEQ ID NO 99
<211> LENGTH: 1329
<212> TYPE: DNA
<213> ORGANISM: Panax ginseng

<400> SEQUENCE: 99
atggataacc aagaaggtag aatcagtata gcgttgctac cattttttagc ccatggtcac      60 atatctccct tctttgagct agccaaacaa ctcgcaaaaa gaaattgcaa tgttttcctc     120
tgttctaccc caatcaatct tagctccatc aagaataagg attcctctgc ttctataaaa     180
ctagttgagc ttcatcttcc atcttcccct gatcttcctc ctcactatca caccacaaat     240
ggcctccctt cccatctcat ggtcccactc ataaacgcct ttgaaacagc aggccccacc     300
ttctctgaaa tccttaaaac cttaaacccc gatttgctta tttatgattt caatccctca     360
tgggcaccgg agatcgcttc gtctcacaat attccggcag tttatttcct aaccacggca     420
gcagccagct cttccattgg cctacatgct ttcaaaaacc caggtgaaaa atacccattt     480
ccagattttt atgataacag taataatacc cctgaaccac cttctgcaga taacatgaag     540
ctacttcatg attttatcgc ttgtttcgaa cgatcttgcg acattatttt gattaagagt     600
tttatagaac tagaagggaa atatatcgat ttgctttcca ctttatctga taaaactttg     660
gttcctgttg gtccactcgt tcaagatcct atgggccata tgaagatcc aaaaacagag      720 cagattataa actggcttga caaaagggct gaatctacag tggtgtttgt ctactttgga     780
agtgagtatt ttctctccaa tgaggaattg aagaagtag caattgggct agagattagc      840
atggttaatt tcatatgggc tgtgagatta attgaaggag agaaaaaagg ggttttacca     900
gagggatttg ttcaaagggt aggagacaga ggattggttg tggaggggtg gctccacag     960 gcaagaattt taggacattc aagcaccggt gggtttgtga ccattgtgg gtggagttct    1020 attgcggaga gtatgaagtt tggggttcca gtaattgcca tggccaggca tcttgatcag    1080
cctttgaatg taagctggc ggcggaggtt ggtgtgggca tggaggttgt gagagatgaa     1140
aatgggaagt ataagagaga agggattgca gaggtaataa gaaaagtcgt tgtggagaaa    1200
agtggggagg ttatgaggag gaaagcaagg gaattgagtg agaaaatgaa agagaaagga    1260
gaggaagaga ttgatagggc agtggaggag ctagtacaaa tttgtaagaa gaagaaagat    1320
gcacaatag                                                            1329

<210> SEQ ID NO 100
<211> LENGTH: 442
<212> TYPE: PRT
<213> ORGANISM: artificial sequence
<220> FEATURE:
<223> OTHER INFORMATION: primer

<400> SEQUENCE: 100

Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
            20                  25                  30
```

```
Lys Arg Asn Cys Asn Val Phe Leu Cys Ser Thr Pro Ile Asn Leu Ser
             35                  40                  45

Ser Ile Lys Asn Lys Asp Ser Ser Ala Ser Ile Lys Leu Val Glu Leu
 50                  55                  60

His Leu Pro Ser Ser Pro Asp Leu Pro Pro His Tyr His Thr Thr Asn
 65                  70                  75                  80

Gly Leu Pro Ser His Leu Met Val Pro Leu Ile Asn Ala Phe Glu Thr
                 85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
            115                 120                 125

His Asn Ile Pro Ala Val Tyr Phe Leu Thr Thr Ala Ala Ala Ser Ser
130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Asn Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Ile Glu Leu Glu Gly Lys Tyr
            195                 200                 205

Ile Asp Leu Leu Ser Thr Leu Ser Asp Lys Thr Leu Val Pro Val Gly
            210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Tyr Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
            275                 280                 285

Arg Leu Ile Glu Gly Glu Lys Lys Gly Val Leu Pro Glu Gly Phe Val
290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
            355                 360                 365

Glu Val Gly Val Gly Met Glu Val Val Arg Asp Glu Asn Gly Lys Tyr
            370                 375                 380

Lys Arg Glu Gly Ile Ala Glu Val Ile Arg Lys Val Val Val Glu Lys
385                 390                 395                 400

Ser Gly Glu Val Met Arg Arg Lys Ala Arg Glu Leu Ser Glu Lys Met
                405                 410                 415

Lys Glu Lys Gly Glu Glu Glu Ile Asp Arg Ala Val Glu Glu Leu Val
            420                 425                 430

Gln Ile Cys Lys Lys Lys Lys Asp Ala Gln
            435                 440
```

```
<210> SEQ ID NO 101
<211> LENGTH: 48
<212> TYPE: DNA
<213> ORGANISM: artificial sequence
<220> FEATURE:
<223> OTHER INFORMATION: primer

<400> SEQUENCE: 101
aactttaaga aggagatata ccatgggcat ggataaccaa aaaggtag          48

<210> SEQ ID NO 102
<211> LENGTH: 46
<212> TYPE: DNA
<213> ORGANISM: artificial sequence
<220> FEATURE:
<223> OTHER INFORMATION: primer

<400> SEQUENCE: 102
tcgagtgcgg ccgcaagctt gtcgacctat tgtgcatctt tcttct            46

<210> SEQ ID NO 103
<211> LENGTH: 48
<212> TYPE: DNA
<213> ORGANISM: artificial sequence
<220> FEATURE:
<223> OTHER INFORMATION: primer

<400> SEQUENCE: 103
aactttaaga aggagatata ccatgggcat ggataaccaa gaaggtag          48

<210> SEQ ID NO 104
<211> LENGTH: 46
<212> TYPE: DNA
<213> ORGANISM: artificial sequence
<220> FEATURE:
<223> OTHER INFORMATION: primer

<400> SEQUENCE: 104
tcgagtgcgg ccgcaagctt gtcgacctat tgttcatctt tcttct            46

<210> SEQ ID NO 105
<211> LENGTH: 48
<212> TYPE: DNA
<213> ORGANISM: artificial sequence
<220> FEATURE:
<223> OTHER INFORMATION: primer

<400> SEQUENCE: 105
aactttaaga aggagatata ccatgggcat ggataaccaa gaaggtag          48

<210> SEQ ID NO 106
<211> LENGTH: 46
<212> TYPE: DNA
<213> ORGANISM: artificial sequence
<220> FEATURE:
<223> OTHER INFORMATION: primer

<400> SEQUENCE: 106
tcgagtgcgg ccgcaagctt gtcgacttaa tattgtgcgt gctgct            46

<210> SEQ ID NO 107
<211> LENGTH: 48
<212> TYPE: DNA
<213> ORGANISM: artificial sequence
<220> FEATURE:
<223> OTHER INFORMATION: primer
```

<400> SEQUENCE: 107
aactttaaga aggagatata ccatgggcat ggataaccaa aaaggtag                48

<210> SEQ ID NO 108
<211> LENGTH: 46
<212> TYPE: DNA
<213> ORGANISM: artificial sequence
<220> FEATURE:
<223> OTHER INFORMATION: primer

<400> SEQUENCE: 108
tcgagtgcgg ccgcaagctt gtcgacctat tgttcatctt tcttct                46

<210> SEQ ID NO 109
<211> LENGTH: 49
<212> TYPE: DNA
<213> ORGANISM: artificial sequence
<220> FEATURE:
<223> OTHER INFORMATION: primer

<400> SEQUENCE: 109
aactttaaga aggagatata ccatgggcat ggatatcgaa aaaggtaga                49

<210> SEQ ID NO 110
<211> LENGTH: 45
<212> TYPE: DNA
<213> ORGANISM: artificial sequence
<220> FEATURE:
<223> OTHER INFORMATION: primer

<400> SEQUENCE: 110
tcgagtgcgg ccgcaagctt gtcgacttaa tattgtgcgt gctgc                45

<210> SEQ ID NO 111
<211> LENGTH: 49
<212> TYPE: DNA
<213> ORGANISM: artificial sequence
<220> FEATURE:
<223> OTHER INFORMATION: primer

<400> SEQUENCE: 111
aactttaaga aggagatata ccatgggcat ggataaccaa gaaggtaga                49

<210> SEQ ID NO 112
<211> LENGTH: 48
<212> TYPE: DNA
<213> ORGANISM: artificial sequence
<220> FEATURE:
<223> OTHER INFORMATION: primer

<400> SEQUENCE: 112
tcgagtgcgg ccgcaagctt gtcgacctat tgtgcatctt tcttcttc                48

<210> SEQ ID NO 113
<211> LENGTH: 26
<212> TYPE: DNA
<213> ORGANISM: artificial sequence
<220> FEATURE:
<223> OTHER INFORMATION: primer

<400> SEQUENCE: 113
agtaagaaaa acagagttca tcatgg                26

<210> SEQ ID NO 114
<211> LENGTH: 20

```
<212> TYPE: DNA
<213> ORGANISM: artificial sequence
<220> FEATURE:
<223> OTHER INFORMATION: primer

<400> SEQUENCE: 114
gcctcggtta ggctagctgt                                                      20

<210> SEQ ID NO 115
<211> LENGTH: 1329
<212> TYPE: DNA
<213> ORGANISM: Panax ginseng
<220> FEATURE:
<221> NAME/KEY: misc_feature
<223> OTHER INFORMATION: GT29-19

<400> SEQUENCE: 115
atggataacc aagaaggtag aatcagtata gcgttgctac cattttttagc ccatggtcac         60 atatctccct tctttgagct agccaaacaa ctcgcaaaaa gaaattgcaa tgttttcctc        120
tgttctaccc caatcaatct tagctccatc aagaataagg attcctctgc ttctataaaa        180
ctagttgagc ttcatcttcc atcttcccct gatcttcctc ctcactatca caccacaaat        240
ggcctccctt cccatctcat ggtcccactc ataaacgcct ttgaaacagc aggccccacc        300
ttctctgaaa tccttaaaac cttaaacccc gatttgctta tttatgattt caatccctca        360
tgggcaccgg agatcgcttc gtctcacaat attccggcag tttatttcct aaccacggca        420
gcagccagct cttccattgg cctacatgct ttcaaaaacc caggtgaaaa atacccatttt        480 ccagatttt  tatgataacag taataatacc cctgaaccac ttctgcaga taacatgaag         540 ctacttcatg attttatcgc ttgtttcgaa cgatcttgcg acattatttt gattaagagt         600
tttatagaac tagaagggaa atatatcgat ttgctttcca ctttatctga taaaactttg        660
gttcctgttg gtccactcgt tcaagatcct atgggccata tgaagatcc aaaaacagag        720 cagattataa actggcttga caaaagggct gaatctacag tggtgtttgt ctgctttgga        780
agtgagtatt ttctctccaa tgaggaattg gaagaagtag caattgggct agagattagc        840
atggttaatt tcatatgggc tgtgagatta attgaaggag agaaaaaagg ggttttacca        900
gagggatttg ttcaaagggt aggagacaga ggattggttg tggaggggtg ggctccacag        960
gcaagaattt taggacattc aagcaccggt gggtttgtga gccattgtgg gtggagttct       1020
attacggaga gtatgaagtt tggggttcca gtaattgcca tggccaggca ttttgatcag       1080
cctttgaatg ctaagctggc ggcggaggtt ggtgtgggca tggaggttgt gagagatgaa       1140
aatgggaagt ataagagaga agatattgca ggggtaataa gaaaagtcgt ggtggagaaa       1200
agtggggagg ttatcaggag gaaagcaagg gaattgagtg agaaaatgaa agagatagga       1260
gagcaattga ttgatagggc agtggaggag ctagtacaaa tttgtaagaa gaagaaagat       1320
gaacaatag                                                             1329

<210> SEQ ID NO 116
<211> LENGTH: 442
<212> TYPE: PRT
<213> ORGANISM: Panax ginseng
<220> FEATURE:
<221> NAME/KEY: misc_feature
<223> OTHER INFORMATION: GT29-19

<400> SEQUENCE: 116

Met Asp Asn Gln Glu Gly Arg Ile Ser Ile Ala Leu Leu Pro Phe Leu
1               5                   10                  15
```

-continued

Ala His Gly His Ile Ser Pro Phe Phe Glu Leu Ala Lys Gln Leu Ala
              20                  25                  30

Lys Arg Asn Cys Asn Val Phe Leu Cys Ser Thr Pro Ile Asn Leu Ser
          35                  40                  45

Ser Ile Lys Asn Lys Asp Ser Ser Ala Ser Ile Lys Leu Val Glu Leu
50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Ile Asn Ala Phe Glu Thr
              85                  90                  95

Ala Gly Pro Thr Phe Ser Glu Ile Leu Lys Thr Leu Asn Pro Asp Leu
              100                 105                 110

Leu Ile Tyr Asp Phe Asn Pro Ser Trp Ala Pro Glu Ile Ala Ser Ser
          115                 120                 125

His Asn Ile Pro Ala Val Tyr Phe Leu Thr Thr Ala Ala Ser Ser
130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Asn Thr Pro Glu Pro Pro Ser Ala
              165                 170                 175

Asp Asn Met Lys Leu Leu His Asp Phe Ile Ala Cys Phe Glu Arg Ser
              180                 185                 190

Cys Asp Ile Ile Leu Ile Lys Ser Phe Ile Glu Leu Glu Gly Lys Tyr
          195                 200                 205

Ile Asp Leu Leu Ser Thr Leu Ser Asp Lys Thr Leu Val Pro Val Gly
210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Phe
              245                 250                 255

Val Cys Phe Gly Ser Glu Tyr Phe Leu Ser Asn Glu Glu Leu Glu Glu
              260                 265                 270

Val Ala Ile Gly Leu Glu Ile Ser Met Val Asn Phe Ile Trp Ala Val
              275                 280                 285

Arg Leu Ile Glu Gly Glu Lys Lys Gly Val Leu Pro Glu Gly Phe Val
290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
              325                 330                 335

Gly Trp Ser Ser Ile Thr Glu Ser Met Lys Phe Gly Val Pro Val Ile
              340                 345                 350

Ala Met Ala Arg His Phe Asp Gln Pro Leu Asn Ala Lys Leu Ala Ala
              355                 360                 365

Glu Val Gly Val Gly Met Glu Val Val Arg Asp Glu Asn Gly Lys Tyr
              370                 375                 380

Lys Arg Glu Asp Ile Ala Gly Val Ile Arg Lys Val Val Glu Lys
385                 390                 395                 400

Ser Gly Glu Val Ile Arg Arg Lys Ala Arg Glu Leu Ser Glu Lys Met
              405                 410                 415

Lys Glu Ile Gly Glu Gln Leu Ile Asp Arg Ala Val Glu Glu Leu Val
              420                 425                 430

Gln Ile Cys Lys Lys Lys Lys Asp Glu Gln
            435                 440

<210> SEQ ID NO 117
<211> LENGTH: 1329
<212> TYPE: DNA
<213> ORGANISM: Panax ginseng
<220> FEATURE:
<221> NAME/KEY: misc_feature
<223> OTHER INFORMATION: GT29-20

<400> SEQUENCE: 117

| | | |
|---|---|---|
| atggataacc aaaaaggtag aatcagtata gcgttgctac cattttttagc ccatggtcac | 60 | |
| atatctcccct tctttgagct agccaaacaa ctcgcgaaaa gaaattgcaa tgttttcctc | 120 | |
| tgttctaccc caatcaatct tagctccatc aaggataagg attcctctgc ttctataaaa | 180 | |
| ctagttgagc ttcatcttcc atcttcccct gatcttcctc ctcactatca caccacaaat | 240 | |
| ggcctcccctt cccatctcat gctcccactc agaaacgcct ttgaaactgc aggccccacc | 300 | |
| ttctctgaaa tccttaaaac cttaaacccc gatttgctta tttatgattt caatccctca | 360 | |
| tgggcaccgg agatcgcttc gtctcacaat attccggcag tttatttcct aaccacggca | 420 | |
| gcagccagct cttccattgg cctacatgct ttcaaaaacc caggtgaaaa atacccattt | 480 | |
| ccagatttt atgataacag taatattacc cctgaaccac ttctgcaga taacatgaag | 540 | |
| ctacttcatg attttatcgc ttgtttcgaa cgatcttgcg acattatttt gattaagagt | 600 | |
| tttagagaac tagaagggaa atatattgat ttgctttcca ctttatctga taaaactttg | 660 | |
| gttcctgttg gtccactcgt tcaagatcct atgggccata tgaagatcc aaaaacagag | 720 | |
| cagattataa actggcttga caaaagggct gaatctacag tggtgtttgt ctgctttgga | 780 | |
| agtgagtatt ttctctccaa tgaggaattg aagaagtag caattgggct agagattagc | 840 | |
| acggttaatt tcatatgggc tgtgagatta attgaaggag agaaaaaagg gattttacca | 900 | |
| gagggggtttg ttcaaaggc aggagacaga ggattggttg tggaggggtg ggctccacag | 960 | |
| gcaagaattt taggacattc aagcaccggt gggtttgtga gccattgtgg gtggagttct | 1020 | |
| attgcggaga gtatgaagtt tggggttcca gtaattgcca tggccaggca tcttgatcag | 1080 | |
| cctttgaatg gtaagctggc ggcggaggtt ggtgtgggca tggaggttgt gagagatgag | 1140 | |
| aatgggaagt ataagagaga agggattgca gaggtaataa gaaagtggt tgtggagaaa | 1200 | |
| agtggggagg ttatcaggag gaaagcaagg gagttgagtg agaaaatgaa agagaaagga | 1260 | |
| gagcaagaga ttgatagggc attggaggag ctagtacaaa tttgtaagaa gaagaaagat | 1320 | |
| gaacaatag | 1329 | |

<210> SEQ ID NO 118
<211> LENGTH: 442
<212> TYPE: PRT
<213> ORGANISM: Panax ginseng
<220> FEATURE:
<221> NAME/KEY: misc_feature
<223> OTHER INFORMATION: GT29-20

<400> SEQUENCE: 118

Met Asp Asn Gln Lys Gly Arg Ile Ser Ile Ala Leu Leu Pro Phe Leu
 1               5                  10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

```
Ser Ile Lys Asp Lys Asp Ser Ala Ser Ile Lys Leu Val Glu Leu
 50                  55                  60

His Leu Pro Ser Ser Pro Asp Leu Pro Pro His Tyr His Thr Thr Asn
 65                  70                  75                  80

Gly Leu Pro Ser His Leu Met Leu Pro Leu Arg Asn Ala Phe Glu Thr
                 85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
        275                 280                 285

Arg Leu Ile Glu Gly Glu Lys Lys Gly Ile Leu Pro Glu Gly Phe Val
    290                 295                 300

Gln Arg Ala Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
        355                 360                 365

Glu Val Gly Val Gly Met Glu Val Val Arg Asp Glu Asn Gly Lys Tyr
    370                 375                 380

Lys Arg Glu Gly Ile Ala Glu Val Ile Arg Lys Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Leu Glu Glu Leu Val
            420                 425                 430

Gln Ile Cys Lys Lys Lys Lys Asp Glu Gln
        435                 440

<210> SEQ ID NO 119
<211> LENGTH: 1329
```

-continued

<212> TYPE: DNA
<213> ORGANISM: Panax ginseng
<220> FEATURE:
<221> NAME/KEY: misc_feature
<223> OTHER INFORMATION: GT29-21

<400> SEQUENCE: 119

| | | | | | |
|---|---|---|---|---|---|
| atggataacc | aaaaaggtag | aatcagtata | gcgttgctac | cattttttagc | caatggtcac | 60 |
| atatctccct | tctttgagct | agccaaacaa | ctcgcgaaaa | gaaattgcaa | tgttttcctc | 120 |
| tgttctaccc | caatcaatct | tagctccatc | aaggataagg | attcctctgc | ttctataaaa | 180 |
| ctagttgagc | ttcatcttcc | atcttcccct | gatcttcctc | ctcactatca | caccacaaat | 240 |
| ggcctccctt | cccatctcat | gctcccactc | agaaacgcct | ttgaaactgc | aggccccacc | 300 |
| ttctctgaaa | tccttaaaac | cttaaacccc | gatttgctta | tttatgattt | caatccctca | 360 |
| tgggcaccgg | agatcgcttc | gtctcacaat | attccggcag | tttatttcct | aaccacggca | 420 |
| gcagccagct | cttccattgg | cctacatgct | ttcaaaaacc | caggtgaaaa | atacccattt | 480 |
| ccagattttt | atgataacag | taatattacc | cctgaaccaa | cttctgcaga | taacatgaag | 540 |
| ctacttcatg | attttatcgc | ttgtttcgaa | cgatcttgcg | acattatttt | gattaagagt | 600 |
| tttagagaac | tagaagggaa | atatattgat | ttgctttcca | ctttatctga | taaaactttg | 660 |
| gttcctgttg | gtccactcgt | tcaagatcct | atgggccata | tgaagatcc | aaaaacagag | 720 |
| cagattataa | actggcttga | caaaagggct | gaatctacag | tggtgtttgt | ctgctttgga | 780 |
| agtgagtatt | ttctctccaa | tgaggaattg | gaagaagtag | caattgggct | agagattagc | 840 |
| acggttaatt | tcatatgggc | tgtgagatta | attgaaggag | agaaaaaagg | gattttacca | 900 |
| gaggggtttg | ttcaaagggt | aggagacaga | ggattggttg | tggaggggtg | ggctccacag | 960 |
| gcaagaattt | taggacattc | aagcatcggt | gggtttgtga | gccattgtgg | gtggagttct | 1020 |
| attgcggaga | gtatgaagtt | tggggttcca | gtaattgcca | tggccaggca | tcttgatcag | 1080 |
| cctttgaatg | gtaagctggc | ggcggaggtt | ggtgtgggca | tggaggttgt | gagagatgag | 1140 |
| aatgggaagt | ataagagaga | agggattgca | gaggtaataa | gaaaagtggt | tgtggagaaa | 1200 |
| agtggggagg | ttatcaggag | gaaagcaagg | gagttgagtg | agaaaatgaa | agagaaagga | 1260 |
| gagcaagaga | ttgatagggc | attggaggag | ctagtacaaa | tttgtaagaa | gaagaaagat | 1320 |
| gaacaatag | | | | | | 1329 |

<210> SEQ ID NO 120
<211> LENGTH: 442
<212> TYPE: PRT
<213> ORGANISM: Panax ginseng
<220> FEATURE:
<221> NAME/KEY: misc_feature
<223> OTHER INFORMATION: GT29-21

<400> SEQUENCE: 120

| Met | Asp | Asn | Gln | Lys | Gly | Arg | Ile | Ser | Ile | Ala | Leu | Leu | Pro | Phe | Leu |
|---|---|---|---|---|---|---|---|---|---|---|---|---|---|---|---|
| 1 | | | | 5 | | | | | 10 | | | | | 15 | |

| Ala | Asn | Gly | His | Ile | Ser | Pro | Phe | Phe | Glu | Leu | Ala | Lys | Gln | Leu | Ala |
|---|---|---|---|---|---|---|---|---|---|---|---|---|---|---|---|
| | | | 20 | | | | | 25 | | | | | 30 | | |

| Lys | Arg | Asn | Cys | Asn | Val | Phe | Leu | Cys | Ser | Thr | Pro | Ile | Asn | Leu | Ser |
|---|---|---|---|---|---|---|---|---|---|---|---|---|---|---|---|
| | | | 35 | | | | | 40 | | | | | 45 | | |

| Ser | Ile | Lys | Asp | Lys | Asp | Ser | Ser | Ala | Ser | Ile | Lys | Leu | Val | Glu | Leu |
|---|---|---|---|---|---|---|---|---|---|---|---|---|---|---|---|
| | | 50 | | | | | 55 | | | | | 60 | | | |

| His | Leu | Pro | Ser | Ser | Pro | Asp | Leu | Pro | Pro | His | Tyr | His | Thr | Thr | Asn |
|---|---|---|---|---|---|---|---|---|---|---|---|---|---|---|---|
| 65 | | | | | 70 | | | | | 75 | | | | | 80 |

```
Gly Leu Pro Ser His Leu Met Leu Pro Leu Arg Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
        275                 280                 285

Arg Leu Ile Glu Gly Glu Lys Lys Gly Ile Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Ile Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
        355                 360                 365

Glu Val Gly Val Gly Met Glu Val Val Arg Asp Glu Asn Gly Lys Tyr
    370                 375                 380

Lys Arg Glu Gly Ile Ala Glu Val Ile Arg Lys Val Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Leu Glu Glu Leu Val
            420                 425                 430

Gln Ile Cys Lys Lys Lys Asp Glu Gln
        435                 440

<210> SEQ ID NO 121
<211> LENGTH: 1329
<212> TYPE: DNA
<213> ORGANISM: Panax ginseng
<220> FEATURE:
<221> NAME/KEY: misc_feature
<223> OTHER INFORMATION: GT29-22
```

<400> SEQUENCE: 121

```
atggataacc aaaaaggtag aatcagtata gcgttgctac cattttttagc ccatggtcac    60
atatctccct tctttgagct agccaaacaa ctcgcgaaaa gaaattgcaa tgttttcctc   120
tgttctaccc caatcaatct tagctccatc aaggataagg attcctctgc ttctataaaa   180
ctagttgagc ttcatcttcc atcttcccct gatcttcctc ctcactatca caccacaaat   240
ggcctccctt cccatctcat gctcccactc agaaacgcct ttgaaactgc aggccccacc   300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa atacccattt   480
ccagatttt atgataacag taatattacc cctgaaccac cttctgcaga taacatgaag   540
ctacttcatg attttatcgc ttgtttcgaa cgatcttgcg acattatttt gattaagagt   600
tttagagaac tagaagggaa atatattgat ttgctttcca ctttatctga taaaactttg   660
gttcctgttg gtccactcgt tcaagatcct atgggccata tgaagatcc aaaaacagag   720
cagattataa actggcttga caaaagggct gaatctacag tggtgtttgt ctgctttgga   780
agtgagtatt ttctctccaa tgaggaattg aagaagtag caattgggct agagattagc   840
acggttaatt tcatatgggc tgtgagatta attgaaggag agaaaaaagg gattttacca   900
gagggtttg ttcaaagggt aggagacaga ggattggttg tggaggggtg ggctccacag   960
gcaagaattt taggacattc aagcaccggt gggtttgtga gccattgtgg gtggagttct  1020
attgcggaga ttatgaagtt tggggttcca gtaattgcca tggccaggca tcttgatcag  1080
cctttgaatg gtaagctggc ggcggaggtt ggtgtgggca tggaggttgt gagagatgag  1140
aatgggaagt ataagagaga agggattgca gaggtaataa gaaagtggt tgtggagaaa  1200
agtggggagg ttatcaggag gaaagcaagg gagttgagtg agaaaatgaa agagaaagga  1260
gagcaagaga ttgatagggc attggaggag ctagtacaaa tttgtaagaa gaagaaagat  1320
gaacaatag                                                           1329
```

<210> SEQ ID NO 122
<211> LENGTH: 442
<212> TYPE: PRT
<213> ORGANISM: Panax ginseng
<220> FEATURE:
<221> NAME/KEY: misc_feature
<223> OTHER INFORMATION: GT29-22

<400> SEQUENCE: 122

```
Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asp Lys Asp Ser Ser Ala Ser Ile Lys Leu Val Glu Leu
        50                  55                  60

His Leu Pro Ser Ser Pro Asp Leu Pro His Tyr His Thr Thr Asn
65                  70                  75                  80

Gly Leu Pro Ser His Leu Met Leu Pro Leu Arg Asn Ala Phe Glu Thr
                85                  90                  95

Ala Gly Pro Thr Phe Ser Glu Ile Leu Lys Thr Leu Asn Pro Asp Leu
                100                 105                 110
```

Leu Ile Tyr Asp Phe Asn Pro Ser Trp Ala Pro Glu Ile Ala Ser Ser
            115                 120                 125

His Asn Ile Pro Ala Val Tyr Phe Leu Thr Thr Ala Ala Ala Ser Ser
        130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
        275                 280                 285

Arg Leu Ile Glu Gly Glu Lys Lys Gly Ile Leu Pro Glu Gly Phe Val
    290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ile Met Lys Phe Gly Val Pro Val Ile
            340                 345                 350

Ala Met Ala Arg His Leu Asp Gln Pro Leu Asn Gly Lys Leu Ala Ala
        355                 360                 365

Glu Val Gly Val Gly Met Glu Val Val Arg Asp Glu Asn Gly Lys Tyr
    370                 375                 380

Lys Arg Glu Gly Ile Ala Glu Val Ile Arg Lys Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Glu Ile Asp Arg Ala Leu Glu Glu Leu Val
            420                 425                 430

Gln Ile Cys Lys Lys Lys Asp Glu Gln
        435                 440

<210> SEQ ID NO 123
<211> LENGTH: 1329
<212> TYPE: DNA
<213> ORGANISM: Panax ginseng
<220> FEATURE:
<221> NAME/KEY: misc_feature
<223> OTHER INFORMATION: GT29-23

<400> SEQUENCE: 123
atggataacc aagaaggtag aatcagtata gcgttgctac cattttttagc ccatggtcac      60 atatctccct tctttgagct agccaaacaa ctcgcaaaaa gaaattgcaa tgttttcctc     120

```
tgttctaccc caatcaatct tagctccatc aagaataagg attcctctgc ttctataaaa    180
ctagttgagc ttcatcttcc atcttcccct gatcttcctc ctcactatca caccacaaat    240
ggcctccctt cccatctcat ggtcccactc ataaacgcct ttgaaacagc aggcccacc     300 ttctctgaaa tccttaaaac cttaaacccc gatttgctta tttatgattt caatccctca    360
tgggcaccgg agatcgcttc gtctcacaat attccggcag tttatttcct aaccacggca    420
gcagccagct cttccattgg cctacatgct ttcaaaaacc caggtgaaaa atacccattt    480
ccagattttt atgataacag taataatacc cctgaaccac cttctgcaga taacatgaag    540
ctacttcatg attttatcgc ttgtttcgaa cgatcttgcg acattatttt gattaagagt    600
tttatagaac tagaagggaa atatatcgat ttgctttcca ctttatctga taaaactttg    660
gttcctgttg gtccactcgt tcaagatcct atgggccata atgaagatcc aaaaacagag    720
cagattataa actggcttga caaaagggct gaatctacag tggtgtttgt ctgctttgga    780
agtgagtatt ttctctccaa tgaggaattg gaagaagtag caattgggct agagattagc    840
atggttaatt tcatatgggc tgtgagatta attgaaggag agaaaaaagg ggttttacca    900
gagggatttg ttcaaagggt aggagacaga ggattggttg tggagggtg ggctccacac     960 gcaagaattt taggacattc aagcaccggt gggtttgtga gccattgtgg gtggagttct   1020
attgcggaga gtatgaagtt tggggttcca gtaattgcca tggccaggca tcttgatcag   1080
cctttgaatg gtaagctggc ggcggaggtt ggtgtgggca tggaggttgt gagagatgaa   1140
aatgggaagt ataagagaga agggattgca gaggtaataa gaaaagtcgt tgtggagaaa   1200 agtgggagg ttatgaggag gaaagcaagg gaattgagtg agaaaatgaa agagaaagga    1260
gaggaagaga ttgatagggc agtggaggag ctagtacaaa tttgtaagaa gaagaaagat   1320
gcacaatag                                                           1329

<210> SEQ ID NO 124
<211> LENGTH: 442
<212> TYPE: PRT
<213> ORGANISM: Panax ginseng
<220> FEATURE:
<221> NAME/KEY: misc_feature
<223> OTHER INFORMATION: GT29-23

<400> SEQUENCE: 124

Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asn Lys Asp Ser Ser Ala Ser Ile Lys Leu Val Glu Leu
        50                  55                  60

His Leu Pro Ser Pro Asp Leu Pro His Tyr His Thr Thr Asn
65                  70                  75                  80

Gly Leu Pro Ser His Leu Met Val Pro Leu Ile Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
    130                 135                 140
```

-continued

Ser Ile Gly Leu His Ala Phe Lys Asn Pro Gly Glu Lys Tyr Pro Phe
145                 150                 155                 160

Pro Asp Phe Tyr Asp Asn Ser Asn Asn Thr Pro Glu Pro Pro Ser Ala
            165                 170                 175

Asp Asn Met Lys Leu Leu His Asp Phe Ile Ala Cys Phe Glu Arg Ser
        180                 185                 190

Cys Asp Ile Ile Leu Ile Lys Ser Phe Ile Glu Leu Glu Gly Lys Tyr
    195                 200                 205

Ile Asp Leu Leu Ser Thr Leu Ser Asp Lys Thr Leu Val Pro Val Gly
210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
        275                 280                 285

Arg Leu Ile Glu Gly Glu Lys Lys Gly Val Leu Pro Glu Gly Phe Val
290                 295                 300

Gln Arg Val Gly Asp Arg Gly Leu Val Val Glu Gly Trp Ala Pro His
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
        355                 360                 365

Glu Val Gly Val Gly Met Glu Val Val Arg Asp Glu Asn Gly Lys Tyr
370                 375                 380

Lys Arg Glu Gly Ile Ala Glu Val Ile Arg Lys Val Val Val Glu Lys
385                 390                 395                 400

Ser Gly Glu Val Met Arg Arg Lys Ala Arg Glu Leu Ser Glu Lys Met
                405                 410                 415

Lys Glu Lys Gly Glu Glu Glu Ile Asp Arg Ala Val Glu Glu Leu Val
            420                 425                 430

Gln Ile Cys Lys Lys Lys Lys Asp Ala Gln
        435                 440

<210> SEQ ID NO 125
<211> LENGTH: 48
<212> TYPE: DNA
<213> ORGANISM: artificial sequence
<220> FEATURE:
<223> OTHER INFORMATION: primer

<400> SEQUENCE: 125
aactttaaga aggagatata ccatgggcat ggataaccaa gaaggtag                48

<210> SEQ ID NO 126
<211> LENGTH: 46
<212> TYPE: DNA
<213> ORGANISM: artificial sequence
<220> FEATURE:
<223> OTHER INFORMATION: primer

<400> SEQUENCE: 126

```
tcgagtgcgg ccgcaagctt gtcgacttgt tcatctttct tcttct          46
```

<210> SEQ ID NO 127
<211> LENGTH: 48
<212> TYPE: DNA
<213> ORGANISM: artificial sequence
<220> FEATURE:
<223> OTHER INFORMATION: primer

<400> SEQUENCE: 127

```
aactttaaga aggagatata ccatgggcat ggataaccaa aaaggtag        48
```

<210> SEQ ID NO 128
<211> LENGTH: 46
<212> TYPE: DNA
<213> ORGANISM: artificial sequence
<220> FEATURE:
<223> OTHER INFORMATION: primer

<400> SEQUENCE: 128

```
tcgagtgcgg ccgcaagctt gtcgacttgt tcatctttct tcttct          46
```

<210> SEQ ID NO 129
<211> LENGTH: 48
<212> TYPE: DNA
<213> ORGANISM: artificial sequence
<220> FEATURE:
<223> OTHER INFORMATION: primer

<400> SEQUENCE: 129

```
aactttaaga aggagatata ccatgggcat ggataaccaa aaaggtag        48
```

<210> SEQ ID NO 130
<211> LENGTH: 46
<212> TYPE: DNA
<213> ORGANISM: artificial sequence
<220> FEATURE:
<223> OTHER INFORMATION: primer

<400> SEQUENCE: 130

```
tcgagtgcgg ccgcaagctt gtcgacttgt tcatctttct tcttct          46
```

<210> SEQ ID NO 131
<211> LENGTH: 48
<212> TYPE: DNA
<213> ORGANISM: artificial sequence
<220> FEATURE:
<223> OTHER INFORMATION: primer

<400> SEQUENCE: 131

```
aactttaaga aggagatata ccatgggcat ggataaccaa aaaggtag        48
```

<210> SEQ ID NO 132
<211> LENGTH: 46
<212> TYPE: DNA
<213> ORGANISM: artificial sequence
<220> FEATURE:
<223> OTHER INFORMATION: primer

<400> SEQUENCE: 132

```
tcgagtgcgg ccgcaagctt gtcgacttgt tcatctttct tcttct          46
```

<210> SEQ ID NO 133
<211> LENGTH: 48
<212> TYPE: DNA

```
<213> ORGANISM: artificial sequence
<220> FEATURE:
<223> OTHER INFORMATION: primer

<400> SEQUENCE: 133
aactttaaga aggagatata ccatgggcat ggataaccaa gaaggtag                48

<210> SEQ ID NO 134
<211> LENGTH: 46
<212> TYPE: DNA
<213> ORGANISM: artificial sequence
<220> FEATURE:
<223> OTHER INFORMATION: primer

<400> SEQUENCE: 134
tcgagtgcgg ccgcaagctt gtcgacttgt gcatctttct tcttct                  46
```

GROUP OF UDP-GLYCOSYLTRANSFERASE FOR CATALYZING CARBOHYDRATE CHAIN ELONGATION AND APPLICATION THEREOF

CROSS-REFERENCE TO RELATED APPLICATIONS

The present application is a U.S. National Stage Application under 35 U.S.C. § 371 of International Application No. PCT/CN2018/087678, filed on May 21, 2019, which claims the benefit of the filing date of Chinese Application No. 201710359069.7, filed on May 19, 2017, the contents of each of which are incorporated by reference herein in their entireties.

TECHNICAL FIELD

The present invention relates to the field of biotechnology and plant biology, and in particular, the present invention relates to a group of glycosyltransferases and uses thereof.

BACKGROUND

Ginsenoside is a generic term for saponins isolated from the plants of *Panax* genus (such as ginseng, *Panax notoginseng*, American ginseng, etc.) and *Gynostemma pentaphyllum*, and is a class of triterpenoids. Ginsenosides may also be called as ginsenosides, notoginsenosides, and gypenosides depending on the source from which they are isolated. Ginsenosides are the main biologically active ingredient in these medicinal plants. Currently, about 150 kinds of saponins have been isolated. Structurally, ginsenosides are mainly bioactive small molecules formed by glycosylation of sapogenins. There are only a few saponins of ginsenosides, mainly of which are protopanoxadiol and protopanaxatriol of dammarane type tetracyclic triterpenes, and oleanolic acid. Glycosylation of sapogenin can increase its water solubility, alter its subcellular localization, and produce different biological activities. Most of the protopanaxadiol saponins are glycosylated on the C3 and/or C20 hydroxyl groups, while the protopanaxatriol saponins are glycosylated on the C6 and/or C20 hydroxyl groups. Different types of glycosylation and varying degrees of glycosylation modification produce ginsenosides with a multitude of molecular structures.

Ginsenosides with different glycosylation modifications have different biological activities. For example, Rb1, Rb2 and Rb3 are Rds with a molecule of glucose, arabinose and xylose extended on the C20-O-Glc, respectively. The experiment has confirmed that the rich saponin Rb1 has the effects of protecting nerve cells and anti-inflammation and anti-oxidation; Rb2 has the effects of inhibiting tumor angiogenesis and tumor metastasis, reducing blood glucose in diabetic mice and reducing blood lipid; Rb3 has the effects of slowing down myocardial ischemia and anti-depression.

Ginsenosides are prepared by using total saponins of ginseng or *Panax notoginseng* or rich saponins as raw materials, depending on a hydrolysis method of chemical, enzymatic and microbial fermentation. Since wild ginseng resources have been basically depleted, ginsenoside resources are currently derived from artificial cultivation of ginseng or notoginseng. Their artificial cultivation has a long growth cycle (generally 5-7 years or more) and is geographically restricted. It is often subject to pests and diseases, thereby requiring a large amount of pesticides. Therefore, there is a serious continuous cropping obstacle during the artificial cultivation of ginseng or *Panax notoginseng* (the ginseng or *Panax notoginseng* plantation needs to fallow for more than 5-15 years to overcome the continuous cropping obstacle), so the yield, quality and security of ginsenosides are all facing challenges.

The development of synthetic biology offers new opportunities for heterologous synthesis of plant-derived natural products. Using yeast as a chassis, through the assembly and optimization of metabolic pathways, it has been realized to synthesize artemisinic acid or dihydroartemisinic acid with cheap monosaccharides, and then to produce artemisinin by one-step chemical conversion, which indicates the synthetic biology has a great potential for drug synthesis in natural products. Ginsenoside monomers are heterologously synthesized by synthetic biological methods using the yeast chassis cells, and the raw materials are cheap monosaccharides, and the preparation process is a safe and controllable fermentation process, thereby avoiding any external contamination (for example, pesticides used in the artificial planting of raw plants). Therefore, the preparation of ginsenoside monomer by synthetic biology technology not only has cost advantages, but also ensures the quality and safety of the finished product. Synthetic biological techniques are used to prepare a sufficient amount of various high-purity natural and non-natural ginseno side monomers for activity determination and clinical experiments to promote the development of innovative drugs for rare ginsenosides.

In recent years, through the transcriptome and functional genomic studies on ginseng, notoginseng and American ginseng, the analysis of the saponin synthesis pathway of ginsenosides has made great progress. In 2006, Japanese and Korean scientists identified the terpenoid cyclase element (dammarenediol synthase, PgDDS), which converts epoxy squalene to dammarene diol. From 2011 to 2012, Korean scientists further identified cytochrome P450 elements CYP716A4 and CYP716A53v2, which oxidize dammarene diol to protopanaxadiol and further oxidize protopanaxadiol to protopanaxatriol.

The artificial synthesis of these pharmaceutically active ginsenosides by synthetic biological methods requires not only the construction of a metabolic pathway for the synthesis of sapogenins, but also the identification of a UDP-glycosyltransferase that catalyzes the glycosylation of ginsenosides. The function of UDP-glycosyltransferase is to transfer glycosyl groups from glycosyl donors (nucleoside diphosphates such as UDP-glucose, UDP-rhamnose, UDP-xylose and UDP-arabinose) to different glycosyl acceptors. According to the genome analysis of plants that have been sequenced, the plant genome often encodes hundreds of different glycosyltransferases. Since the substrates (including glycosyl donors and glycosyl acceptors) that may be catalyzed by UDP-glycosyltransferase are very diverse, the functional identification of this UDP-glycosyltransferase poses great difficulties. Until 2014, the first UDP-glycosyltransferase (UGTPg1) involved in ginsenoside glycosylation was identified by Chinese scholars, which can be transferred to a glucosyl group on the C20 hydroxyl group of the Protopanaxadiol ginsenoside. Subsequently, Korean scientists cloned two UDP-glycosyltransferase elements (PgUGT74AE2 and PgUGT94Q2) in ginseng, which can transfer a glucosyl group and a glucosyl extension to the C3 position of the Protopanaxadiol saponin. Almost at the same time, Chinese scholars also independently cloned two glycosyltransferase elements UGTPg45 and UGTPg29, which have the same functions as PgUGT74AE2 and PgUGT94Q2, from ginseng. In 2015, Chinese scholars further identified a UDP-glycosyltransferase element (UGTPg100) that can transfer a glucosyl group to the C6 position of the Protopanaxatriol. In 2015, Korean scholars discovered a glycosyltransferase GpUGT23 that extends a glucosyl group on C20 of Protopanaxadiol and protopanaxatriol saponin in *Gynostemma pentaphyllum*. However, up to now, in addition to a glycosyltransferase plant extending a glycosyl at the C3 position, other glycosyltransferases in ginseng that catalyze the extension of the carbohydrate chain have not been reported.

Under this background, the inventors have cloned and identified the glycosyltransferase which can extend a glucosyl or xylosyltaxol on the C20 of the Protopanaxadiol and protopanaxatriol saponin and the glycosyltransferase which can extend a xylosyltaxol on the C6 of the protopanaxatriol saponin. The glycosyltransferase can be used for the preparation of ginsenosides including ginsenoside Rb1, ginsenoside Rb3, gypenoside LXXV, gypenoside XVII, notoginsenoside U, notoginsenoside R1, notoginsenoside R2 and notoginsenoside R3.

SUMMARY OF THE INVENTION

The present invention provides a novel set of glycosyltransferases and a method for catalyzing a glycosylation reaction of a tetracyclic triterpenoid using the glycosyltransferases.

In a first aspect of the present invention, it provides an in vitro glycosylation method, comprising the steps of:

transferring a glycosyl group from the glycosyl donor to the following positions of the tetracyclic triterpenoid in the presence of a glycosyltransferase:

the first glycosyl group on position C20 and/or position C3;

thereby forming a glycosylated tetracyclic triterpenoid;

wherein the glycosyltransferase is selected from the group consisting of:

a glycosyltransferase as shown in SEQ ID NO.: 4, 6, 8, 8, 39, 41, 43, 45, 47, 49, 51, 53, 55, 57, 59, 98, or 100 or a derivative polypeptide thereof.

In another preferred embodiment, the tetracyclic triterpenoids glycosylated at the position C20 include ginsenosides Rd, CK, F1 and F2.

In a second aspect of the present invention, it provides an in vitro glycosylation method, comprising the steps of:

transferring a glycosyl group from a glycosyl donor to the following positions of the tetracyclic triterpenoid in the presence of a glycosyltransferase:

the first glycosyl group on position C6;

thereby forming a glycosylated tetracyclic triterpenoid;

wherein the glycosyltransferase is selected from the group consisting of:

a glycosyltransferase as shown in SEQ ID NO.: 12, 14, 16, 18, 20, 22, 24, 26, 28 and 30 or a derivative polypeptide thereof.

In another preferred embodiment, the tetracyclic triterpenoids glycosylated at the position C6 includes Rg1 or Rh1.

The present invention provides a method for in vitro glycosylation comprising the steps of:

transferring a glycosyl group from a glycosyl donor to the following positions of the tetracyclic triterpenoid in the presence of a glycosyltransferase:

the first glycosyl group on position C3;

thereby forming a glycosylated tetracyclic triterpenoid;

wherein the glycosyltransferase is selected from the group consisting of:

a glycosyltransferase as shown in SEQ ID NO.: 39, 41, 43, 45, 47, 49, 51, 53, 55, 57, 59, 90, 92, 94, 96, 98, 100, 116, 118, 120, 122, and 124 or a derivative polypeptide thereof.

In another preferred embodiment, the tetracyclic triterpenoids glycosylated on the position C3 includes F2 or Rh2.

In another preferred embodiment, the derivative polypeptide is independently selected from the group consisting of:

(a) a polypeptide of any one or more of the amino acid sequences as shown in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;

(b) a derivative polypeptide formed by adding a tag sequence, a signal sequence or a secretion signal sequence to SEQ ID NOs: 4, 6, 8, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 and having glycosyltransferase activity;

(c) a derivative polypeptide of an amino acid sequence having an identity of 95% with the amino acid sequence of any one or more of SEQ ID NOs: 4, 6, 8, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124 and having glycosyltransferase activity.

In another preferred embodiment, (c) further includes a derivative polypeptide formed by substitution, deletion or addition of one or several amino acid residues of any one or more of the amino acid sequences of SEQ ID NOs.: 4, 6, 8, 14, 16, 18, 20, 22, 24, 26, 28, 30, 39, 41, 43, 45 47, 49, 51, 53, 55, 57, 59, 90, 92, 94, 96, 98, 100, 116, 118, 120, 122, and 124 and having the glycosyltransferase activity.

In a third aspect of the present invention, it provides an isolated polypeptide, wherein the isolated polypeptide is:

a polypeptide or a derivative polypeptide thereof of any one or more of the amino acid sequences as shown in SEQ ID NOs.: 4, 6, 8, 28, 30, 39, 41, 43, 45, 47, 49, 51, 53, 55, 57, 59, 90, 92, 94, 96, 98, 100, 116, 118, 120, 122, and 124;

wherein the derivative polypeptide is selected from the group consisting of:

(a) a polypeptide of any one or more of the amino acid sequences in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;

(b) a derivative polypeptide formed by adding a tag sequence, a signal sequence or a secretion signal sequence to SEQ ID NOs: 4, 6, 8, 28, 30, 39, 41, 43, 45, 47, 49, 51, 53, 55, 57, 59, 90, 92, 94, 96, 98, 100, 116, 118, 120, 122, or 124 and having a glycosyltransferase activity;

(c) a derivative polypeptide of an amino acid sequence having an identity of 95% with the amino acid sequence as shown in any one or more of SEQ ID NOs: 4, 6, 8, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, (c) further includes a derivative polypeptide formed by substitution, deletion or addition of one or several amino acid residues of any one or more of the amino acid sequences of SEQ ID NOs.: 4, 6, 8, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, the isolated polypeptide is used for in vitro glycosylation.

In a fourth aspect of the present invention, it provides an isolated polynucleotide, wherein the polynucleotide is selected from the group consisting of:

(A) a nucleotide sequence encoding the polypeptide of claim 4;

(B) a nucleotide sequence encoding a polypeptide as shown in SEQ ID NOs: 4, 6, 8, 28, 30, 39, 41, 43, 45, 47, 49, 51, 53, 55, 57, 59, 90, 92, 94, 96, 100, 116, 118, 120, 122 or 124;

(C) a nucleotide sequence as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123;

(D) a nucleotide sequence having an identity of 95% (preferably 98%) with a nucleotide sequence as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123;

(E) a nucleotide sequence complementary (preferably completely complementary) to the nucleotide sequence of any of (A)-(D).

In another preferred embodiment, (D) further includes a nucleotide sequence formed by truncation or addition of 1-60 (preferably 1-30, more preferably 1-10) nucleotides at 5' end and/or 3' end of the nucleotide sequences of SEQ ID NOs.: 3, 5, 7, 27, 29, 38, 40, 42, 44, 46, 48, 50, 52, 54, 56, 58, 89, 91, 93, 95, 97, 99, 115, 117, 119, 121, or 123.

In another preferred embodiment, the nucleotide sequences as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123, encoding the polypeptides as shown in SEQ ID NOs: 4, 6, 8, 28, 30, 39, 41, 43, 45, 47, 49, 51, 53, 55, 57, 59, 90, 92, 94, 96, 98, 100, 116, 118, 120, 122, or 124.

In a fifth aspect of the present invention, it provides a vector comprising the polynucleotide according to the fourth aspect of the present invention, or expressing the isolated polypeptide according to the third aspect of the present invention.

Use of the isolated polypeptide according to the third aspect of the present invention for catalyzing one or more of the following reactions, or preparing a catalytic formulation which catalyzes one or more of the following reactions:
transferring the glycosyl group from the glycosyl donor to the following positions of the tetracyclic triterpenoid to extend the carbohydrate chain:
(i) the first glycosyl group on position C-6;
(ii) the first glycosyl group on position C-20; and/or
(iii) the first glycosyl group on position C3.

In another preferred embodiment, the glycosyl group transfer comprises the addition or substitution of a glycosyl group on a specific position.

In another preferred embodiment, it also provides a use of a polypeptide or a derivative
polypeptide thereof for catalyzing the following reactions or for preparing a catalytic formulation which catalyzes the following reactions:
transferring a glycosyl group from a glycosyl donor to the following positions of the tetracyclic triterpenoid in the presence of a glycosyltransferase:
the first glycosyl group on position C-6; or the first glycosyl group on position C-20;
and/or the first glycosyl group on position C-3;
thereby forming a glycosylated tetracyclic triterpenoid;
wherein the glycosyltransferase is selected from the group consisting of:
a glycosyltransferase, or a derivative polypeptide thereof as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124.

In another preferred embodiment, it also provides a use of a polypeptide or a derivative
polypeptide thereof for catalyzing the following reactions, or for preparing a catalytic formulation which catalyzes the following reactions:
transferring a glycosyl group from glycosyl donor to the following positions of the tetracyclic triterpenoid in the presence of a glycosyltransferase:
the first glycosyl group on position C20 and/or position C3;
thereby forming a glycosylated tetracyclic triterpenoid;
wherein the glycosyltransferase is selected from the group consisting of:
a glycosyltransferase or a derivative polypeptide thereof as shown in SEQ ID NO.: 4, 6, 8, 39, 41, 43, 45, 47, 49, 51, 53, 55, 57, 59, 98, and 100.

In another preferred embodiment, it also provides a use of a polypeptide or a derivative
polypeptide thereof for catalyzing the following reactions or for preparing a catalytic formulation which catalyzes the following reactions:
transferring a glycosyl group from a glycosyl donor to the following positions of the tetracyclic triterpenoid in the presence of a glycosyltransferase:
the first glycosyl group on position C6;
thereby forming a glycosylated tetracyclic triterpenoid;
wherein the glycosyltransferase is selected from the group consisting of:
a glycosyltransferase or a derivative polypeptide thereof as shown in SEQ ID NO.: 12, 14, 16, 18, 20, 22, 24, 26, 28, and 30.

In another preferred embodiment, it also provides a use of a polypeptide or a derivative
polypeptide thereof for catalyzing the following reactions or for preparing a catalytic formulation which catalyzes the following reactions:
transferring a glycosyl group from a glycosyl donor to the following positions of the tetracyclic triterpenoid in the presence of a glycosyltransferase:
the first glycosyl group on position C-3;
thereby forming a glycosylated tetracyclic triterpenoid;
wherein the glycosyltransferase is selected from the group consisting of:
a glycosyltransferase or a derivative polypeptide thereof as shown in SEQ ID NO.: 39, 41, 43, 45, 47, 49, 51, 53, 55, 57, 59, 90, 92, 94, 96, 98, 100, 116, 118,120, 122, and 124.

In another preferred embodiment, the derivative polypeptide is each selected from the group consisting of:
(a) a polypeptide having an amino acid sequence of any one of SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;
(b) a derivative polypeptide formed by adding a tag sequence, a signal sequence or a secretion signal sequence to SEQ ID NOs: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 and having a glycosyltransferase activity;
(c) a derivative polypeptide of an amino acid sequence having an identity of 95% with the amino acid sequence as shown in any one of SEQ ID NOs: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, the glycosyl donor comprises a nucleoside diphosphate selected from the group consisting of UDP-glucose, ADP-glucose, TDP-glucose, CDP-glucose, GDP-glucose, UDP-acetylglucose, ADP-acetylglucose, TDP-acetylglucose, CDP-acetylglucose, GDP-acetylglucose, UDP-xylose, ADP-xylose, TDP-xylose, CDP-xylose, GDP-xylose, UDP-galacturonic acid, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, UDP-xylose, ADP-xylose, TDP-xylose, CDP-xylose, GDP-xylose, and other nucleoside diphosphate hexose and nucleoside pentose diphosphate, and a combination thereof.

In another preferred embodiment, the glycosyl donor comprises a uridine diphosphate (UDP) saccharide selected from the group consisting of UDP-glucose, UDP-galacturonic acid, UDP-galactose, UDP-arabinose, UDP-rhamnose, UDP-xylose, and other uridine diphosphate hexose and uridine pentose diphosphate, and a combination thereof.

In another preferred embodiment, the isolated polypeptide is used to catalyze one or more of the following reactions or to prepare a catalytic formulation which catalyzes one or more of the following reactions:

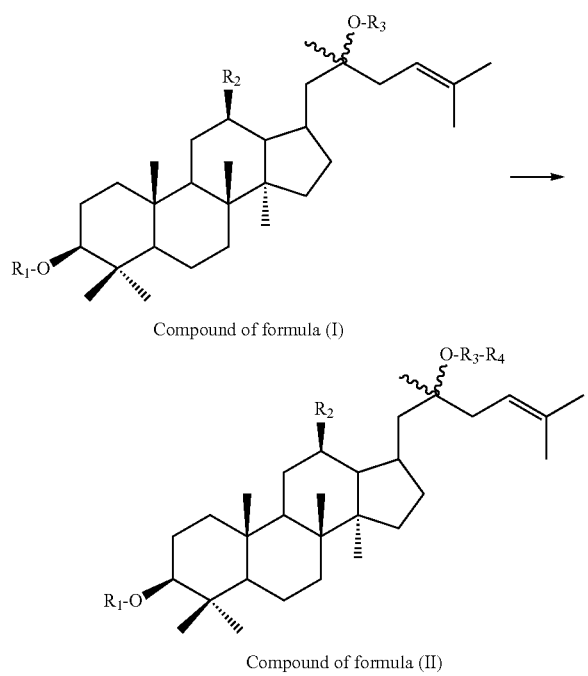

Compound of formula (I)

Compound of formula (II)

wherein, R1 is H, a monosaccharide glycosyl or a polysaccharide glycosyl; R2 is H or OH; R3 is a monosaccharide glycosyl; and R4 is a monosaccharide glycosyl; and the polypeptide is selected from the group consisting of SEQ ID NOs: 4, 6, 8, 39, 41, 43, 45, 47, 49, 51, 53, 55, 57, 59, 98, 100, 116, 118, 120, 122, or 124 or a derivative polypeptide thereof.

In another preferred embodiment, the monosaccharide comprises glucose (Glc), rhamnose (Rha), acetylglucose (Glc(6)Ac), arabinofuranose (Araf), arabian pyranose (Arap), or xylose (Xyl), etc.

In another preferred embodiment, the polysaccharide comprises a polysaccharide consisting of 2-4 monosaccharides such as Glc(2-1)Glc, Glc(6-1)Glc, Glc(6)Ac, Glc(2-1)Rha, Glc(6-1)Arap, Glc(6-1)Xyl, Glc(6-1)Araf, Glc(3-1)Glc (3-1), Glc(2-1) Glu(6)Ac, Glc(6-1)Arap(4-1)Xyl, Glc(6-1)Arap(2-1)Xyl, or Glc(6-1)Arap(3-1)Xyl.

In another preferred embodiment, the compound with the substitution of R1-R4 is shown in the following table:

| substrate | R1 | R2 | R3 | R4 | product |
|---|---|---|---|---|---|
| CK | H | OH | Glc | Glc | Gypenoside LXXV |
| DMG | H | H | Glc | Glc | DMGG |
| F2 | Glc | OH | Glc | Glc | Gypenoside XVII |
| Rd | Glc(2-1)Glc | OH | Glc | Glc | Rb1 |
| CK | H | OH | Glc | Xyl | Gypenoside XIII |
| DMG | H | H | Glc | Xyl | DMGX |
| F2 | Glc | OH | Glc | Xyl | Gypenoside IX |
| Rd | Glc(2-1)Glc | OH | Glc | Xyl | Rb3 | that is, when R1 is H, R2 is OH, and R3 is a glucosyl, the compound of formula (I) is ginsenoside CK (CK);

when the R1 is H, R2 is OH, and both R3 and R4 are glucosyls, the compound of the formula (II) is Gypenoside LXXV;

when the R1 is H, R2 is OH, R3 is a glucosyl, and R4 is a xylose group, the compound of the formula (II) is Gypenoside XIII;

when both R1 and R2 are H and R3 is a glucosyl, the compound of formula (I) is ginsenoside DMG;

when both R1 and R2 are H, and both R3 and R4 are glucosyls, the compound of formula (II) is saponin DMGG (20-O-β-(D-glucopyranosyl)-β-(D-glucopyranosyl)-dammarenediol);

when both R1 and R2 are H, R3 is a glucosyl, and R4 is a xylose group, the compound of formula (II) is saponin DMGX (20-O-β-(D-xylopyranosyl)-β-(D-glucopyranosyl)-dammarenediol);

when R1 is a glucosyl, R2 is OH, and R3 is a glucosyl, the compound of formula (I) is ginsenoside F2 (F2);

when R1 is a glucosyl, R2 is OH, and both R3 and R4 are glucosyls, the compound of formula (II) is Gypenoside XVII;

when R1 is a glucosyl, R2 is OH, R3 is a glucosyl, and R4 is a xylose group, the compound of formula (II) is Gypenoside IX;

when R1 is two glucosyls (Glc(2-1)Glc), R2 is OH, and R3 is a glucosyl, the compound
of formula (I) is ginsenoside Rd;

when R1 is two glucosyls (Glc(2-1)Glc), R2 is OH, and both R3 and R4 are glucosyls, the compound of formula (II) is ginsenoside Rb1; or when R1 is two glucosyls (Glc(2-1)Glc), R2 is OH, R3 is a glucosyl, and R4 is a xylose group, the compound of formula (II) is ginsenoside Rb3;

when the R1 is H, R2 is OH, R3 is a glucosyl, and R4 is an arabinose group, the compound of the formula (II) is ginsenoside F3;

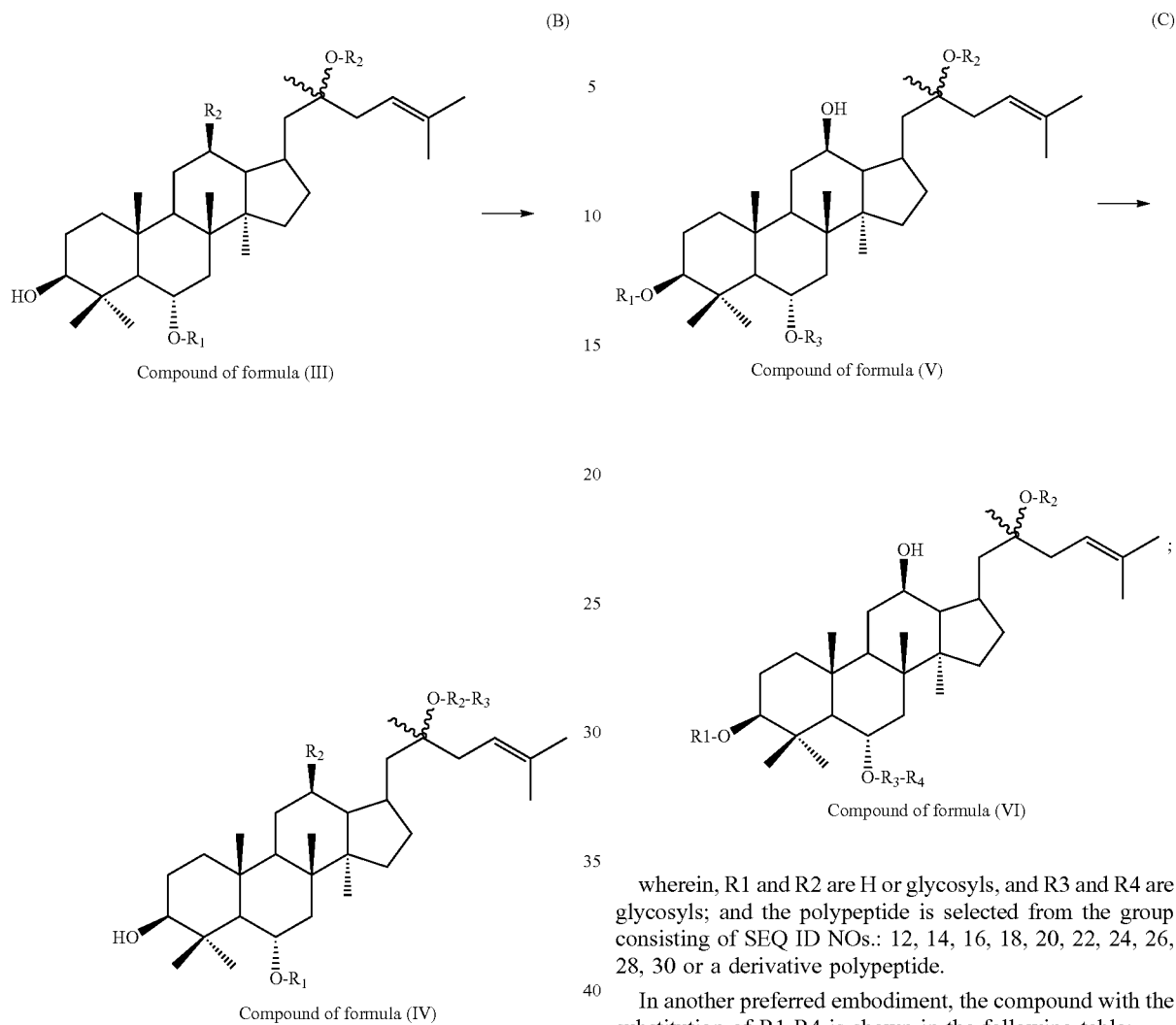

Compound of formula (III)

Compound of formula (V)

Compound of formula (IV)

Compound of formula (VI)

wherein, R1 is H, a glycosyl or polysaccharide glycosyl group, R2 is a glycosyl group, and R3 is a glycosyl group, and the polypeptide is selected from the group consisting of SEQ ID NOs.: 4 and a derivative polypeptide thereof.

In another preferred embodiment, the compound with the substitution of R1-R3 is shown in the following table:

| substrate | R1 | R2 | R3 | product |
|---|---|---|---|---|
| F1 | H | Glc | Glc | notoginsenoside U |
| Rg1 | Glc | Glc | Glc | notoginsenoside R3 | that is, when R1 is H, and R2 is a glucosyl, the compound of the formula (III) is ginsenoside F1 (F1);

when R1 is H, and both R2 and R3 are glucosyls, the compound of the formula (IV) is notoginsenoside U; when R1 and R2 are glucosyls, the compound of the formula (III) is ginsenoside Rg1 (Rg1); or when R1, R2 and R3 are glucosyl groups, the compound of the formula (IV) is notoginsenoside R3 (R3);

wherein, R1 and R2 are H or glycosyls, and R3 and R4 are glycosyls; and the polypeptide is selected from the group consisting of SEQ ID NOs.: 12, 14, 16, 18, 20, 22, 24, 26, 28, 30 or a derivative polypeptide.

In another preferred embodiment, the compound with the substitution of R1-R4 is shown in the following table:

| substrate | R1 | R2 | R3 | R4 | product |
|---|---|---|---|---|---|
| Rg1 | H | Glc | Glc | Xyl | notoginsenoside R1 |
| Rg1 | H | Glc | Glc | Glc | 20-O-Glucosylginsenoside Rf |
| Rh1 | H | H | Glc | Xyl | notoginsenoside R2 |
| Rh1 | H | H | Glc | Glc | ginsenoside Rf | that is, when R1 is H, and both R2 and R3 are glucosyls, the compound of the formula (V) is ginsenoside Rg1;

when R1 is H, R2 and R3 are glucosyls, and R4 is a xylose group, the compound of formula (VI) is notoginsenoside R1;

when R1 is H, R2 and R3 are glucosyls, and R4 is a glucosyl, the compound of formula (VI) is saponin 20-O-Glucosylginsenoside Rf;

when R1 and R2 are H, and R3 is a glucosyl, the compound of formula (V) is ginsenoside Rh1;

when R1 and R2 are H, R3 is a glucosyl, and R4 is a xylose group, the compound of the formula (VI) is notoginsenoside R2; when R1 and R2 are H, R3 and R4 are glucosyls, the compound of formula (VI) is ginsenoside Rf.

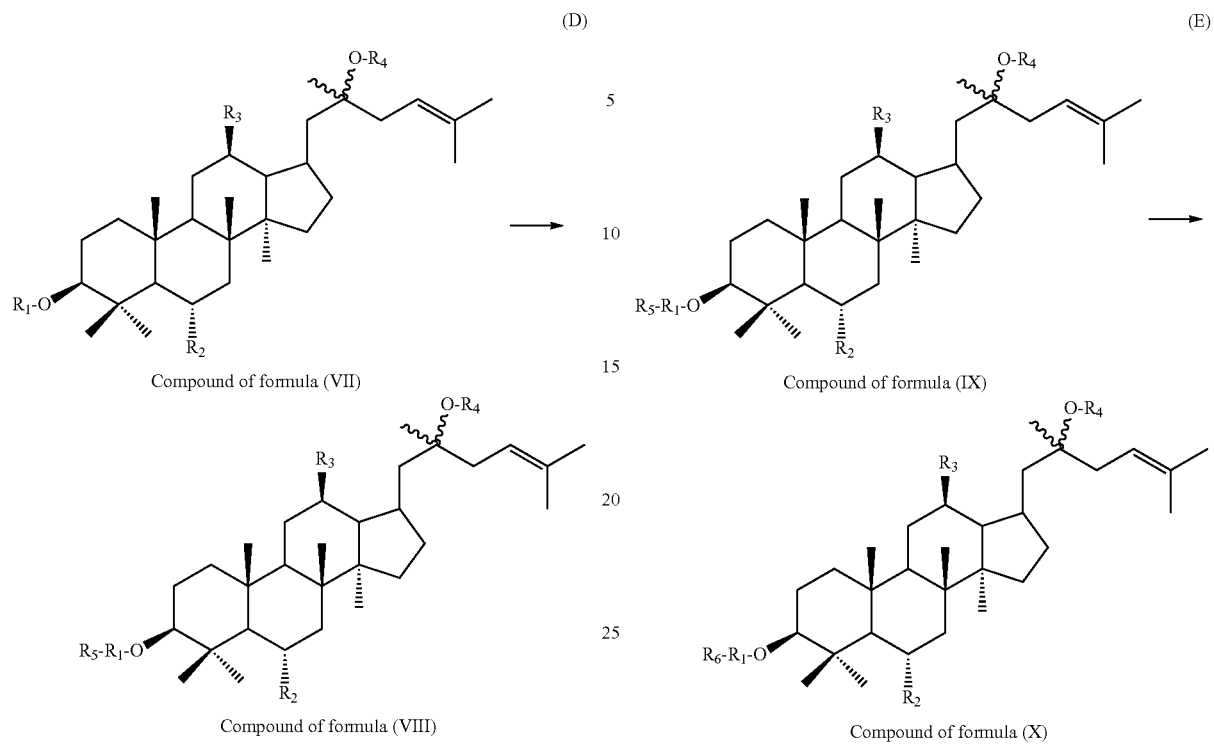

Compound of formula (VII)

Compound of formula (VIII)

Compound of formula (IX)

Compound of formula (X)

wherein, R1 is a glycosyl; R2 and R3 are OH or H; R4 is a glycosyl or H; R5 is a glycosyl, and R5-R1-O is a first glycosyl-derived glycosyl at C3 position; and the polypeptide is selected from the group consisting of SEQ ID NOs.: 39, 41, 43, 45, 47, 49, 51, 53, 55, 57, 59, 98, 100, 116, 118, 120, 122, and 124 and a derivative polypeptide thereof;

the compound with the substitution of R1-R4 is shown in the following table:

| substrate | R1 | R2 | R3 | R4 | R5 | product |
|---|---|---|---|---|---|---|
| Rh2 | Glc | H | OH | H | Glc | Rg3 |
| F2 | Glc | H | OH | Glc | Glc | Rd |
| Gypenoside XVII | Glc | H | OH | Glc(6,1)Glc | Glc | Rb1 |
| Gypenoside IX | Glc | H | OH | Glc(6,1)xyl | Glc | Rb3 | that is, when R1 is a glucosyl; R2 is H, R3 is OH, R4 is H, and the compound of the formula (VII) is Rh2;

R1 is a glucosyl; R2 is H, R3 is OH, R4 is a glucosyl, and the compound of the formula (VII) is F2;

R1 is a glucosyl; R2 is H, R3 is OH, R4 is two glucosyls, and the compound of formula (VII) is Gypenoside XVII;

R1 is a glucosyl; R2 is H, R3 is OH, R4 is a glucosyl group with a xylosyl group extended, and the compound of formula (VII) is Gypenoside IX; when the substrate of (VII) compound is Rh2, the product of formula (VIII) is Rg3; when the substrate of (VII) compound is F2, the product of formula (VIII) is Rd; when the substrate of (VII) compound is Gypenoside XVII, the product of formula (VIII) is Rb1; when the substrate of (VII) compound is Gypenoside IX, the product of formula (VIII) is Rb3.

wherein, R1 is a glycosyl; R2 and R3 are OH or H; R4 is a glycosyl or H; R5 is a glycosyl, R5-R1-O is a derivative glycosyl from the first glycosyl on C3 position; and R6 is a glycosyl, R6-R1-O is a derivative glycosyl from the first glycosyl on C3 position, and the polypeptide is selected from the group consisting of SEQ ID NOs.: 41, 45, 90, 92, 94 and 96 and a derivative polypeptide thereof;

R1 is two glucosyls, R2 is H, R3 is OH, R4 is H, and the compound of formula (IX) is Rg3.

R1 is two glucosyls, R2 is H, R3 is OH, R4 is a glucosyl, and the compound of formula (IX) is Rd.

In another preferred embodiment, the glycosyl is selected from the group consisting of: a glucosyl, a xylose group, a galacturonic acid group, a galactosyl, an arabinose group, a rhamnosyl, and other hexose and pentose groups.

In another preferred embodiment, the compounds of (I), (III), (V), (VII), (IX) in the reaction formula include, but are not limited to, dammarane tetracyclic triterpenoids in S or R configuration, lanostanes tetracyclic triterpenoids, apotirucallane tetracyclic triterpenoids, tirucallanes tetracyclic triterpenoids, cycloartanes (cycloaltine) tetracyclic triterpenoids, cucurbitane tetracyclic triterpenoids or meliacanes tetracyclic triterpenoid.

In another preferred embodiment, the compounds of (II), (IV), (VI), (VIII), or (X) in the reaction formula include ginsenoside Rg3, ginsenoside Rd, ginsenoside Rb1, ginsenoside Rb3, saponin DMGG, saponin DMGX, gypenoside LXXV, gypenoside XVII, gypenoside XIII, gypenoside IX, notoginsenoside U and, notoginsenoside R1, and notoginsenoside R2, notoginsenoside R3, 3-O-β-(D-xylopyranosyl)-β-(D-glucopyranos yl)-PPD; 3-O-β-(D-xylopyranosyl)-β-(D-glucopyranosyl)-CK, 20-O-Glucosylginsenoside Rf and Ginsenoside F3.

In a sixth aspect of the present invention, it provides a method for performing a glycosyl transfer catalytic reaction, comprising the steps of: performing a glycosyl transfer catalytic reaction in the presence of the polypeptide or a derivative polypeptide thereof according to the third aspect of the present invention.

In another preferred embodiment, the method further includes the steps: in the presence of a glycosyl donor and a polypeptide and a derivative polypeptide thereof according to the third aspect of the present invention, converting the compound of formula (I) to the compound of formula (II), or converting the compound of formula (III) to the compound of formula (IV), or converting the compound of formula (V) to the compound of formula (VI); or converting the compound of formula (VII) to the compound of formula (VIII), or converting the compound (IX) to the compound of the formula (IX). In another preferred embodiment, the method further comprises adding the polypeptide and the derivative polypeptide thereof to a catalytic reaction, respectively; and/or adding the polypeptide and the derivative polypeptide thereof simultaneously to a catalytic reaction.

In another preferred embodiment, the method further includes co-expressing a nucleotide sequence encoding a glycosyltransferase with a key gene in the anabolic pathway of dammarenediol and/or protopanoxadiol and/or protopanaxatriol in the host cell, thereby obtaining the compound of formula (II), (IV), (VI), (VIII), or (X).

In another preferred embodiment, the host cell is a yeast cell or an *E. coli* cell.

In another preferred embodiment, the polypeptide is a polypeptide having an amino acid sequence as shown in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 or a derivative polypeptide thereof.

In another preferred embodiment, the nucleotide sequence encoding the polypeptide is as shown in SEQ ID NOs.: 3, 5, 7, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123.

In another preferred embodiment, the method further includes: providing an additive for regulating the enzyme activity to the reaction system.

In another preferred embodiment, the additive for regulating enzyme activity is: an additive that increases enzyme activity or inhibits enzyme activity.

In another preferred embodiment, the additive for regulating the enzyme activity is selected from the group consisting of $Ca^1+$, $Co^2+$, $Mn^2+$, $Ba^2+$, $Al^3±$, $Ni^2+$, $Zn^2+$, and $Fe^2+$. In another preferred embodiment, the additive for regulating the enzyme activity is a substance capable of generating $Ca^1+$, $Co^2+$, $Mn^2+$, $Ba^2+$, $Al^3±$, $Ni^2+$, $Zn^2+$, or Fee+. In another preferred embodiment, the glycosyl donor is a nucleoside diphosphate saccharide selected from the group consisting of UDP-glucose, ADP-glucose, TDP-glucose, CDP-glucose, GDP-glucose, UDP-xylose, ADP-xylose, TDP-xylose, CDP-xylose, GDP-xylose, UDP-galacturonic acid, UDP-acetylglucose, ADP-acetylglucose, TDP-acetylglucose, CDP-acetylglucose, GDP-acetylglucose, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, and other nucleoside diphosphate hexose and nucleoside diphosphate pentose, and a combination thereof. In another preferred embodiment, the glycosyl donor is a uridine diphosphate saccharide, selected from the group consisting of UDP-glucose, UDP-xylose, UDP-galacturonic acid, UDP-galactose, UDP-arabinose, UDP-rhamnose, and other uridine diphosphate hexose and uridine diphosphate pentose, and a combination thereof.

In another preferred embodiment, the pH of the reaction system is: pH 4.0-10.0, preferably pH 5.5-9.0.

In another preferred embodiment, the temperature of the reaction system is: 10° C.-105° C., preferably 20° C.-50° C.

In another preferred embodiment, the key genes in the dammarenediol anabolic pathway include (but are not limited to): a dammarenediol synthase gene.

In another preferred embodiment, the key genes in the ginsenoside CK anabolic pathway include (but are not limited to): a dammarenediol synthase gene, cytochrome P450 CYP716A47 gene, gene of reductase for P450 CYP716A47, and glycosyltransferase UGTPg1 at C20 position of tetracyclic triterpenes (Genbank accession number KF377585.1), and a combination thereof.

In another preferred embodiment, the key genes in the ginsenoside F1 anabolic pathway include (but are not limited to): a dammarenediol synthase gene, a cytochrome P450 CYP716A47 gene, a gene of reductase for P450 CYP716A47, a cytochrome P450 CYP716A53V2 gene and a gene of a reductase thereof and a glycosyltransferase UGTPg1 at C20 position of tetracyclic triterpene, and a combination thereof.

In another preferred example, the key genes in the ginsenoside Rg1 anabolic pathway include (but are not limited to): a dammarenediol synthase gene, a cytochrome P450 CYP716A47 gene, a gene of reductase for P450 CYP716A47, and glycosyltransferase UGTPg1 and UGTPg100 at C20 and C6 position of tetracyclic triterpenes (Genbank accession number AKQ76388.1), and a combination thereof.

In another preferred embodiment, the substrate of the glycosyl-catalyzed reaction is a compound of formula (I), (III), (V), (VII), (IX), and the products are compounds (II), (IV), (VI), (VIII), (X);

In another preferred embodiment, the compound of formula (I) is ginsenoside CK, and the compound of formula (II) is gypenosides LXXV (20-O-β-(D-glucopyranosyl)-((β-(D-glucopyranosyl)-protopanaxadiol);

or, the compound of formula (I) is ginsenoside DMG, and the compound of formula (II) is a new ginsenoside DMGG (20-O-β-(D-glucopyranosyl)-(β-(D-glucopyranosyl)-dammarenediol);

the compound of formula (I) is ginsenoside F2, and the compound of formula (II) is gypenosides XVII (3-O-β-(D-glucopyranosyl)-20-O-β-(D-glucopyranosyl)-(β-(D-glucopyranosyl)-protopanaxadiol);

or, the compound of formula (I) is ginsenoside Rd, and the compound of formula (II) is ginsenoside Rb1 (3-O-β-(D-glucopyranosyl)-β-(D-glucopyranosyl)-20-O-β-(D-glucopyranosyl)-β-(D-glucopyranosyl)-protopanaxadiol);

or, the compound of formula (I) is ginsenoside Rd, and the compound of formula (II) is ginsenoside Rb3 (3-O-β-(D-glucopyranosyl)-β-(D-glucopyranosyl)-20-O-β-(D-xylopyranosyl)-β-(D-glucopyranosyl)-protopanaxadiol);

the compound of formula (I) is ginsenoside CK, and the compound of formula (II) is gypenosides XIII;

the compound of formula (I) is ginsenoside DMG, and the compound of formula (II) is ginsenoside DMGX (20-O-β-(D-glucopyranosyl)-β-(D-glucopyranosyl)-dammarenediol);

the compound of formula (I) is ginsenoside F2, and the compound of formula (II) is gypenosides IX;

the compound of formula (I) is ginsenoside CK, and the compound of formula (II) is ginsenoside F3; in another preferred embodiment, the compound of formula (III) is ginsenoside F1, and the compound of formula (IV) is notoginsenoside U (20-O-β-(D-glucopyranosyl)-β-(D-glucopyranosyl)-protopanaxatriol);

In another preferred embodiment, the compound of formula (III) is ginsenoside Rg1, and the compound of formula (IV) is notoginsenoside R3;

In another preferred embodiment, the compound of formula (V) is ginsenoside Rg1, and the compound of formula (VI) is notoginsenoside R1 (6-O-β-(D-xylopyranosyl)-β-(D-glucopyranosyl)-20-O-β-(D-glucopyranosyl)-protopanaxatriol);

the compound of formula (V) is ginsenoside Rg1, and the compound of formula (VI) is 20-O-Glucosylginsenoside Rf;

the compound of formula (V) is ginsenoside Rh1, and the compound of formula (VI) is notoginsenoside R2 (6-O-β-(D-xylopyranosyl)-β-(D-glucopyranosyl)-protopanaxatriol).

Or, the compound of formula (V) is ginsenoside Rh1, and the compound of formula (VI) is ginsenoside Rf.

In another preferred embodiment, the compound of formula (III) is ginsenoside Rg1, and the compound of formula (IV) is notoginsenoside R3;

In another preferred embodiment, the compound of formula (VII) is Rh2, and the product of compound of formula (VIII) is Rg3;

the compound of formula (VII) is F2, and the product of compound of formula (VIII) is Rd;

the compound of formula (VII) is Gypenoside XVII, and the product of compound of formula (VIII) is Rb1;

the compound of formula (VII) is Gypenoside IX, and the product of compound of formula (VIII) is Rb3.

In another preferred embodiment, the compound of formula (IX) is Rg3, and the product of compound of formula (X) is 3-O-β-(D-xylopyranosyl)-β-(D-glucopyranosyl)-PPD;

the compound of formula (IX) is Rd, and the product of compound of formula (X) is 3-O-β-(D-xylopyranosyl)-β-(D-glucopyranosyl)-CK.

In a seventh aspect of the present invention, it provides a genetically engineered host cell containing the vector according to the fifth aspect of the present invention, or with a polynucleotide according to the fourth aspect of the present invention integrated into the gene thereof.

In another preferred embodiment, the cell is a prokaryotic cell or a eukaryotic cell.

In another preferred embodiment, the host cell is a eukaryotic cell, such as a yeast cell or a plant cell.

In another preferred embodiment, the host cell is a *Saccharomyces cerevisiae* cell.

In another preferred embodiment, the host cell is a prokaryotic cell, such as *E. coli*.

In another preferred embodiment, the host cell is a ginseng cell.

In another preferred embodiment, the host cell is not a cell that naturally produces compounds of formula (II), (IV), (VI), (VII), or (X).

In another preferred embodiment, the host cell is not a cell that naturally produces ginsenoside Rg3, ginsenoside Rd, ginsenoside Rb1, ginsenoside Rb3, saponin DMGG, saponin DMGX, gypenosides LXXV, gypenosides XVII, gypenosides XIII, gypenosides IX, notoginsenoside U and notoginsenoside R1, notoginsenoside R2, notoginsenoside R3, 3-O-β-(D-xylopyranosyl)-β-(D-glucopyranosyl)-PPD; 3-O-β-(D-xylopyranosyl)-β-(D-glucopyranosyl)-CK, 20-O-Glucosylginsenoside Rf or Ginsenoside F3.

In another preferred embodiment, the key genes in the dammarene glycol anabolic pathway include (but are not limited to): a dammarene glycol synthase gene.

In another preferred example, the host cell contains key genes in the ginsenoside CK anabolic pathway including (but not limited to): a dammarene glycol synthase gene, a cytochrome P450 CYP716A47 gene, and a P450 CYP716A47 reductase gene and a glycosyltransferase UGTPg1 at the C20 site of the tetracyclic triterpene, or a combination thereof.

In another preferred example, the host cell contains key genes in the ginsenoside F1 anabolic pathway including (but not limited to): a dammarene glycol synthase gene, a cytochrome P450 CYP716A47 gene, and a reductase gene for P450 CYP716A47, a cytochrome P450 CYP716A53V2 gene and a glycosyltransferase UGTPg1 on the C20 site of the tetracyclic triterpene, or a combination thereof.

In another preferred example, the key genes in the ginsenoside Rg1 anabolic pathway include (but are not limited to): a dammarene glycol synthase gene, a cytochrome P450 CYP716A47 gene, a gene of a reductase for P450 CYP716A47, and glycosyltransferase UGTPg1 and UGTPg100 (Genbank accession number AKQ76388.1) on C20 and C6 of cyclotriterpenes, or a combination thereof.

In an eighth aspect of the present invention, it provides use of the host cell according to the seventh aspect of the present invention for preparing an enzyme catalytic reagent, or for producing a glycosyltransferase, or as a catalytic cell, or for producing formula (II), (IV), (VI), (VIII) or (X) compounds.

In a ninth aspect of the present invention, it provides a method for producing a transgenic plant, comprising the steps of: regenerating a genetically engineered host cell of claim 8 into a plant, and the genetically engineered host cell is a plant cell.

In another preferred embodiment, the genetically engineered host cell is a ginseng cell.

In another preferred embodiment, the genetically engineered host cell is a *Panax notoginseng* cell.

It should be understood that, within the scope of the present invention, each technical feature of the present invention described above and in the following (as examples) may be combined with each other to form a new or preferred technical solution, which is not listed here due to space limitations.

Figure 2:
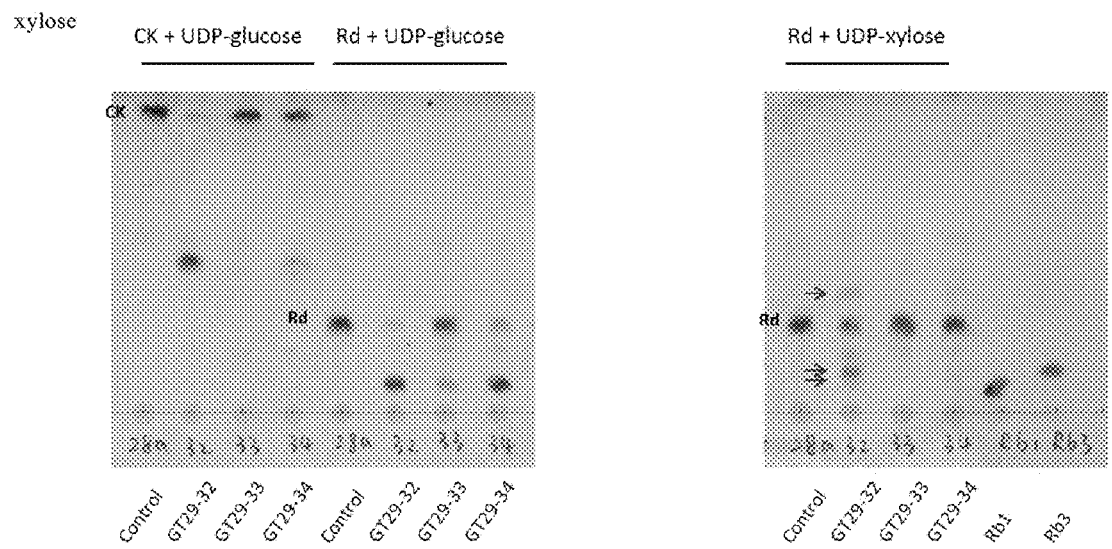

FIG. 2 shows a TLC pattern of a transglycosyl reaction catalyzed by glycosyltransferases GT29-32, GT29-33 and GT29-34 with ginsenoside CK or Rd as a glycosyl acceptor and UDP-glucose or UDP-xylose as a glycosyl donor. Control represents the lysate supernatant of the pet28a empty vector recombinant as an enzyme solution; GT29-32, GT29-33 and GT29-34 respectively represent the lysate supernatants of recombinant *E. coli* BL21-GT29-32, BL21-GT29-33 and BL21-GT29-34 as an enzyme solution.

Figure 3:
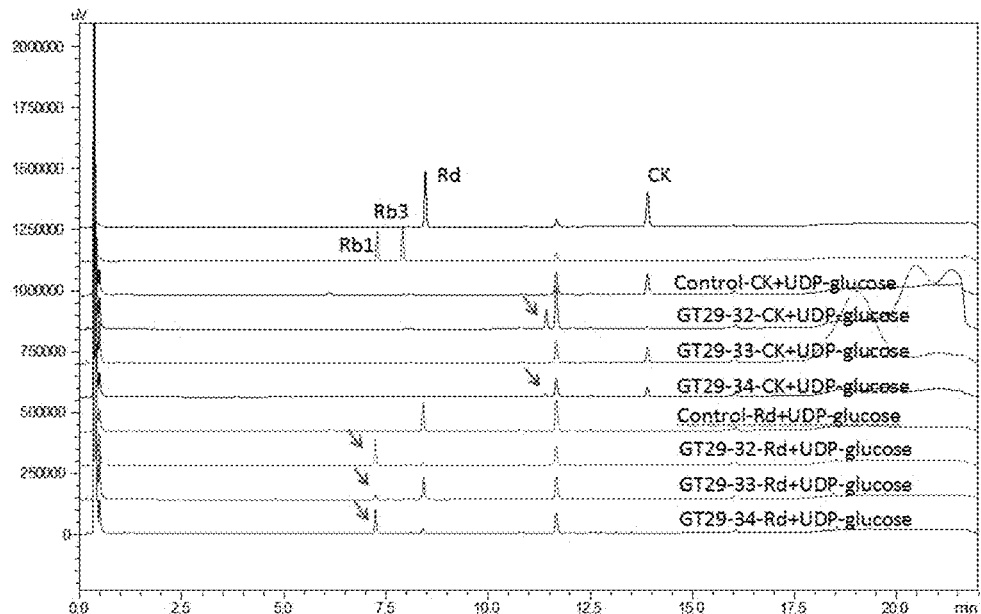

FIG. 3 shows an HPLC pattern of a transglycosyl reaction catalyzed by glycosyltransferases GT29-32, GT29-33 and GT29-34 with ginsenoside CK or Rd as a glycosyl acceptor and UDP-glucose as a glycosyl donor. Control represents the lysate supernatant of the pet28a empty vector recombinant as an enzyme solution; GT29-32, GT29-33 and GT29-34 respectively represent the lysate supernatants of recombinant *E. coli* BL21-GT29-32, BL21-GT29-33 and BL21-GT29-34 as an enzyme solution.

Figure 4:
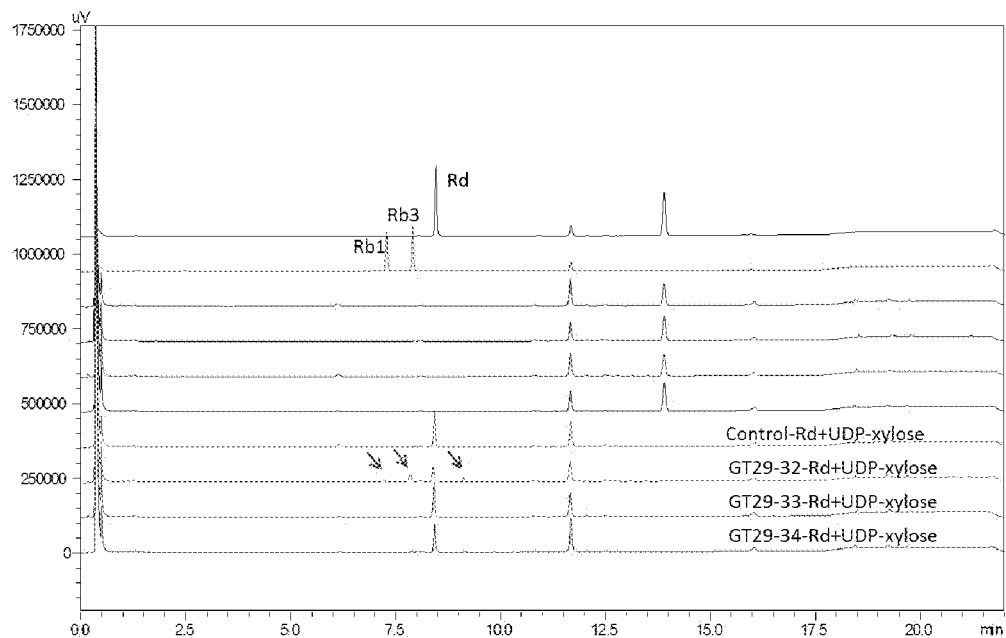

FIG. 4 shows an HPLC pattern of a transglycosyl reaction catalyzed by glycosyltransferases GT29-32, GT29-33, and GT29-34 with ginsenoside Rd as a glycosyl acceptor and UDP-xylose as a glycosyl donor. Control represents the lysate supernatant of the pet28a empty vector recombinant as an enzyme solution; GT29-32, GT29-33, and GT29-34 respectively represent the lysate supernatants of recombinant *E. coli* BL21-GT29-32, BL21-GT29-33 and BL21-GT29-34 as an enzyme solution.

Figure 5:
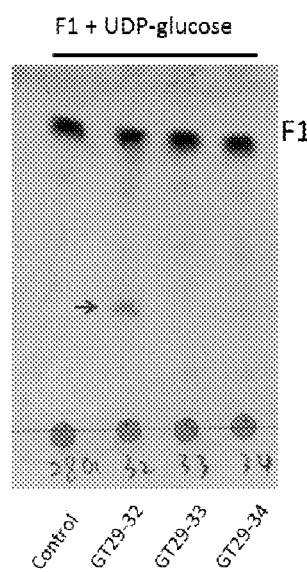

FIG. 5 shows a TLC pattern of a transglycosyl reaction catalyzed by glycosyltransferases GT29-32, GT29-33 and GT29-34 with ginsenoside F1 as a glycosyl acceptor and UDP-glucose as a glycosyl donor. Control represents the lysate supernatant of the pet28a empty vector recombinant as an enzyme solution; GT29-32, GT29-33, and GT29-34 respectively represent the lysate supernatants of recombinant *E. coli* BL21-GT29-32, BL21-GT29-33 and BL21-GT29-34 as an enzyme solution.

Figure 6:
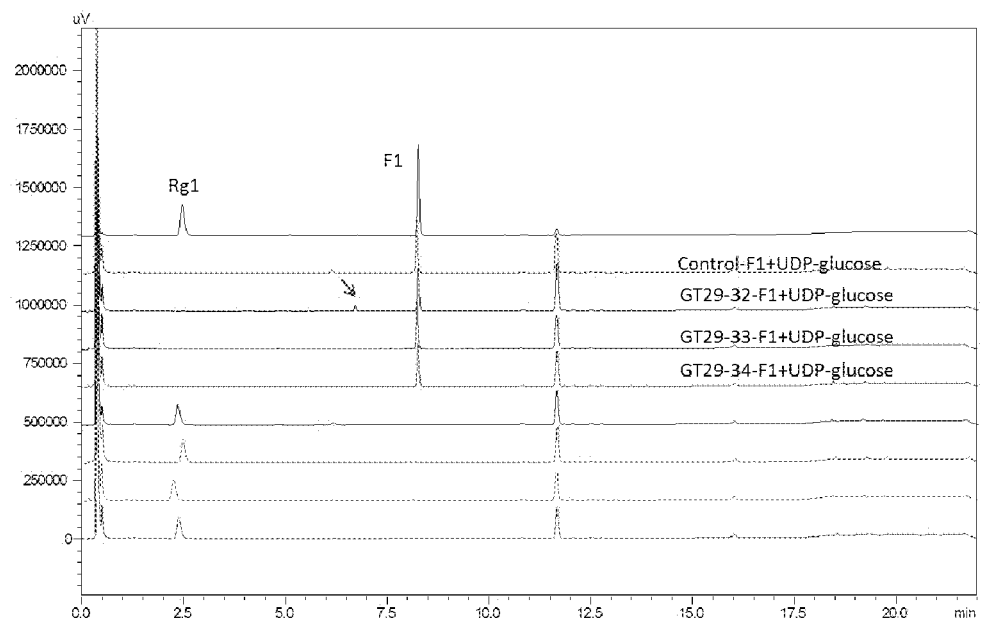

FIG. 6 shows an HPLC pattern of a transglycosyl reaction catalyzed by glycosyltransferases GT29-32, GT29-33, and GT29-34 using ginsenoside F1 as a glycosyl acceptor and UDP-glucose as a glycosyl donor. Control represents the lysate supernatant of the pet28a empty vector recombinant as an enzyme solution; GT29-32, GT29-33, and GT29-34 respectively represent the lysate supernatants of recombinant *E. coli* BL21-GT29-32, BL21-GT29-33 and BL21-GT29-34 as an enzyme solution.

Figure 7:
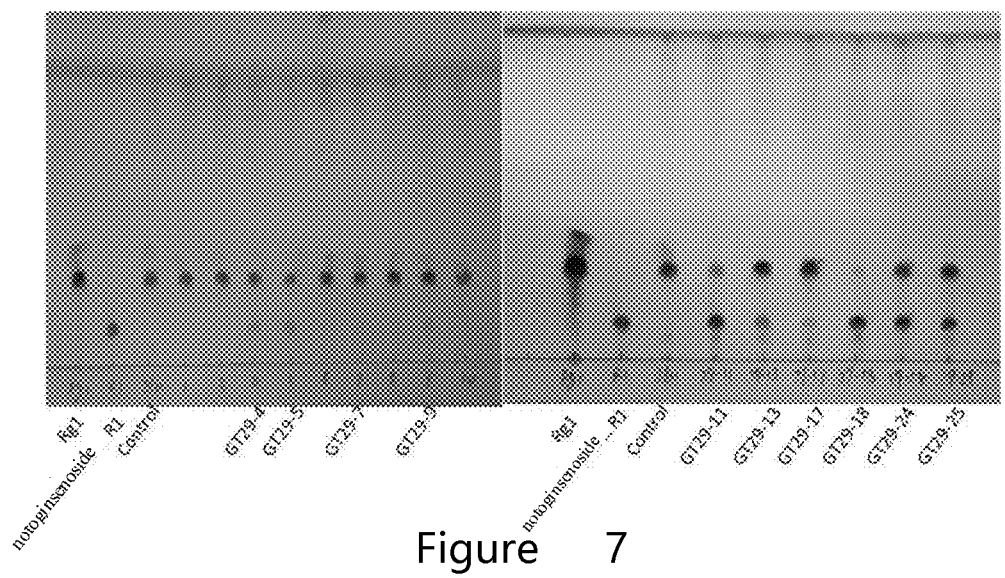

FIG. 7 shows a TLC pattern of a transglycosyl reaction catalyzed by the glycosyltransferases GT29-4, GT29-5, GT29-7, GT29-9, GT29-11, GT29-13, GT29-17, GT29-18, GT29-24 and GT29-25 with ginsenoside Rg1 as a glycosyl acceptor and UDP-xylose as a glycosyl donor. Control represents the lysate supernatant of the pet28a empty vector recombinant as an enzyme solution; GT29-4, GT29-5, GT29-7, GT29-9, GT29-11, GT29-13, GT29-17, GT29-18, GT29-24 and GT29-25 respectively represent the lysate supernatants of recombinant *E. coli* BL21-GT29-4, BL21-GT29-5, BL21-GT29-7, BL21-GT29-9, BL21-GT29-11, BL21-GT29-13, BL21-GT29-17, BL21-GT29-18, BL21-GT29-24 and BL21-GT29-25 as an enzyme solution.

Figure 8:
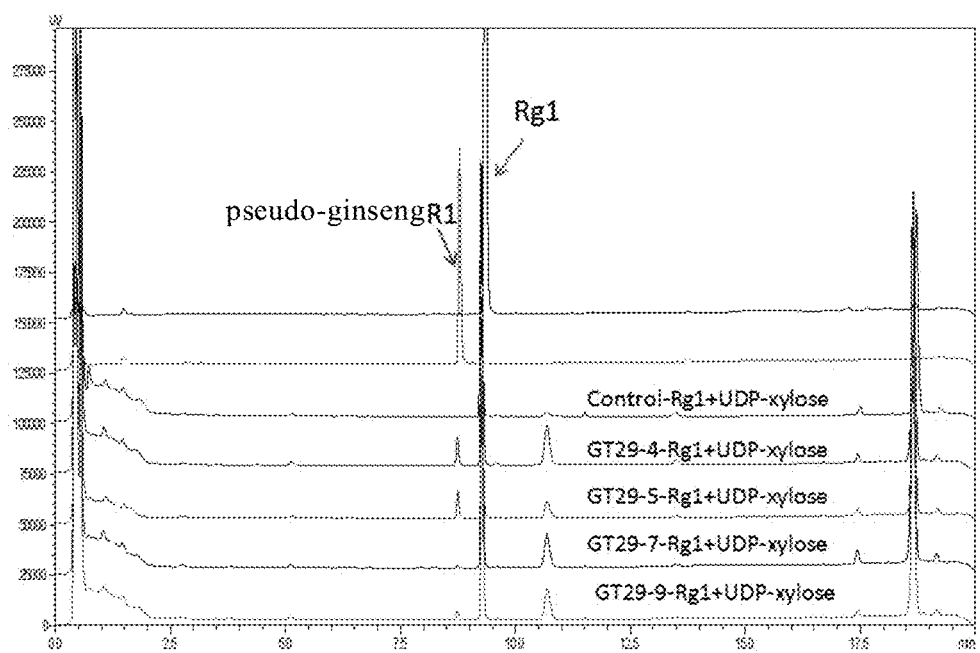

FIG. 8 shows an HPLC pattern of a transglycosyl reaction catalyzed by the glycosyltransferases GT29-4, GT29-5, GT29-7 and GT29-9 using ginsenoside Rg1 as a glycosyl acceptor and UDP-xylose as a glycosyl donor. Control represents the lysate supernatant of the pet28a empty vector recombinant as an enzyme solution; GT29-4, GT29-5, GT29-7, and GT29-9, respectively represents the lysate supernatants of recombinant *E. coli* BL21-GT29-4, BL21-GT29-5, BL21-GT29-7 and BL21-GT29-9 as an enzyme solution.

Figure 9:
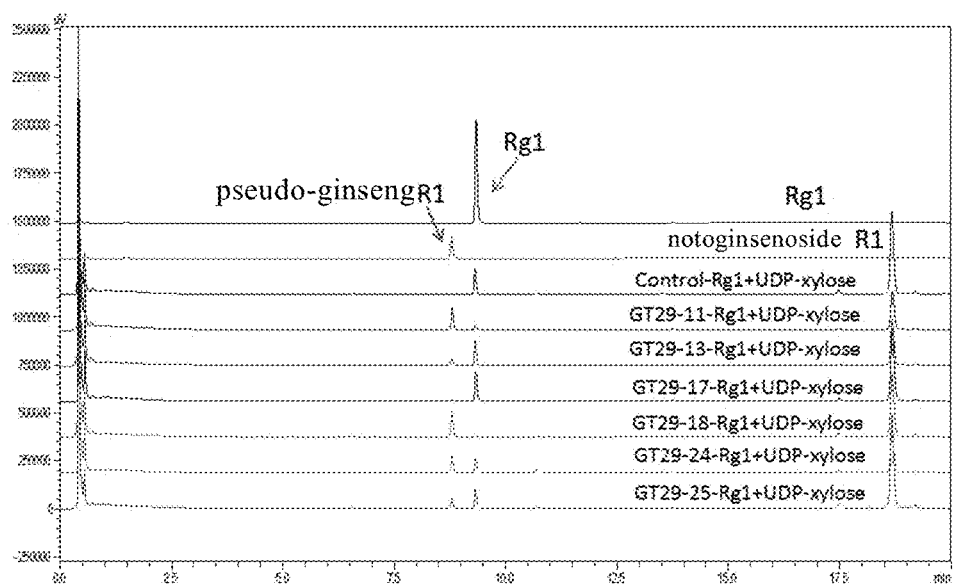

FIG. 9 shows an HPLC pattern of a transglycosyl reaction catalyzed by the glycosyltransferases GT29-11, GT29-13, GT29-17, GT29-18, GT29-24 and GT29-25 with the ginsenoside Rg1 as a glycosyl receptor and UDP-xylose as a glycosyl donor. Control represents the lysate supernatant of the pet28a empty vector recombinant as an enzyme solution; GT29-11, GT29-13, GT29-17, GT29-18, GT29-24 and GT29-25 respectively represents the lysate supernatants of recombinant *E. coli* BL21-GT29-11, BL21-GT29-13, BL21-GT29-17, BL21-GT29-18, BL21-GT29-24, and BL21-GT29-25 as an enzyme solution.

Figure 10:
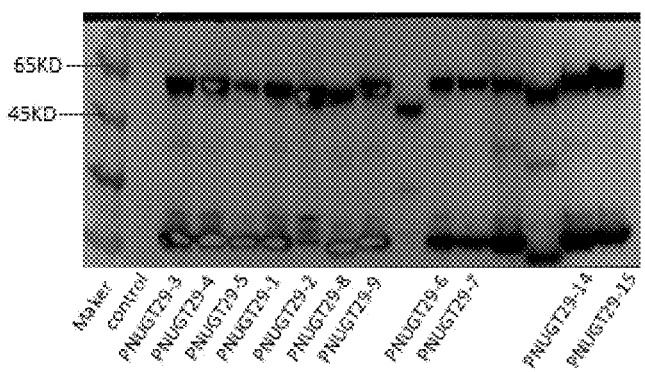

FIG. 10 shows Western blot detection for the protein expressions of glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as enzyme solution.

Figure 11:
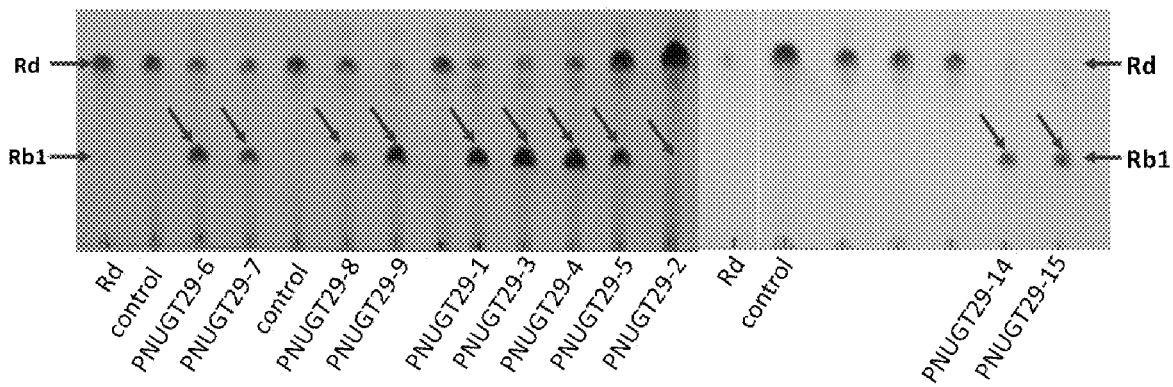

FIG. 11 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside Rd as a glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as an enzyme solution.

Figure 12:
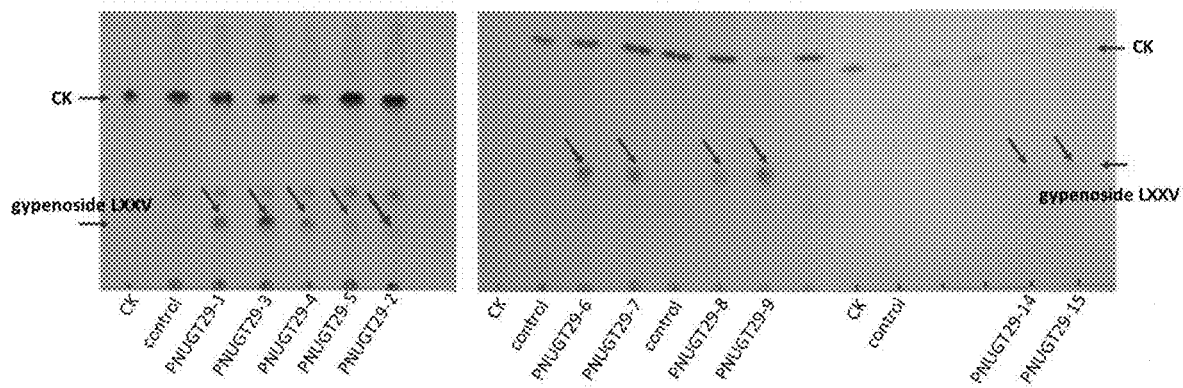

FIG. 12 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside CK as glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as an enzyme solution.

Figure 13:
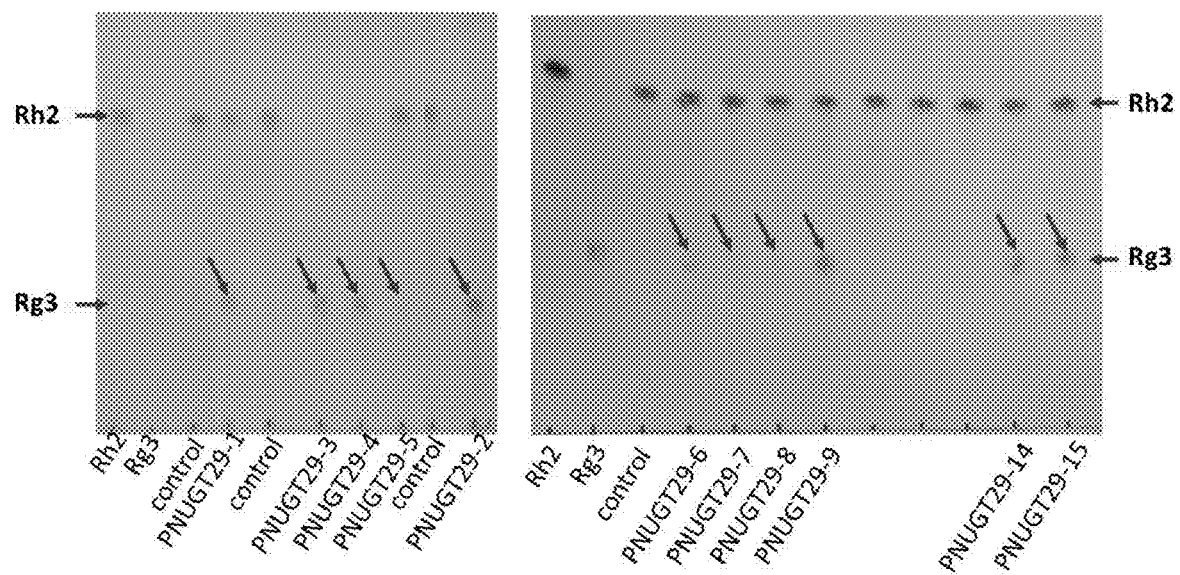

FIG. 13 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside Rh2 as a glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as enzyme solution.

Figure 14:
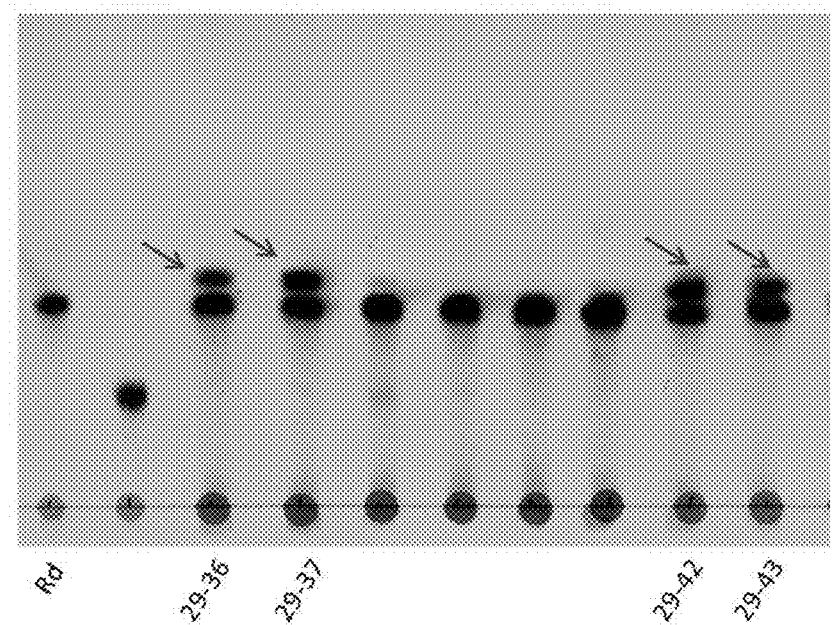

FIG. 14 shows a TLC pattern of a transglycosyl reaction catalyzed by the glycosyltransferases GT29-36, GT29-36, GT29-42 and GT29-43 with ginsenoside Rd as a glycosyl acceptor and UDP-xylose as a glycosyl donor. GT29-36, GT29-36, GT29-42 and GT29-43 respectively represents the lysate supernatants of recombinant *E. coli* BL21-GT29-36, BL21-GT29-36, BL21-GT29-42 and BL21-GT29-43 as an enzyme solution.

Figure 15:
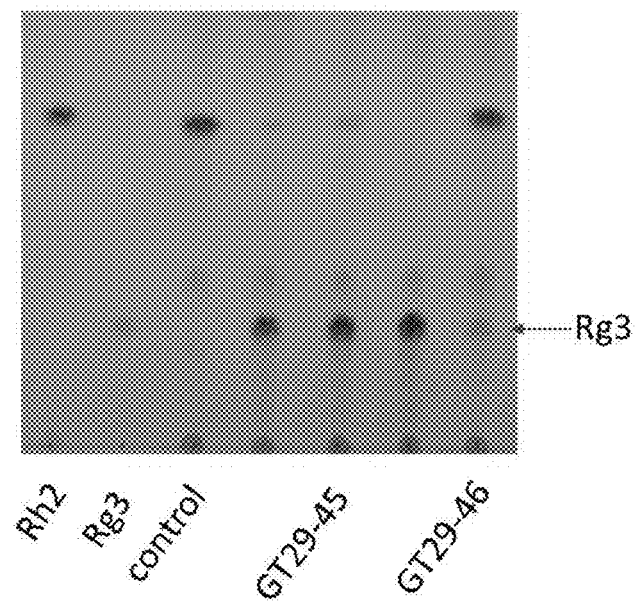

FIG. 15 shows a TLC pattern of a transglycosyl reaction catalyzed by the glycosyltransferase GT29-45 and GT29-46 using ginsenoside Rh2 as a glycosyl acceptor and UDP-glucose as a glycosyl donor. Control represents the lysate supernatant of the pet28a empty vector recombinant as an enzyme solution; GT29-45 and GT29-46 respectively represents the lysate supernatant of the recombinant *E. coli* BL21-GT29-45 and BL21-GT29-46 as an enzyme solution.

Figure 16:
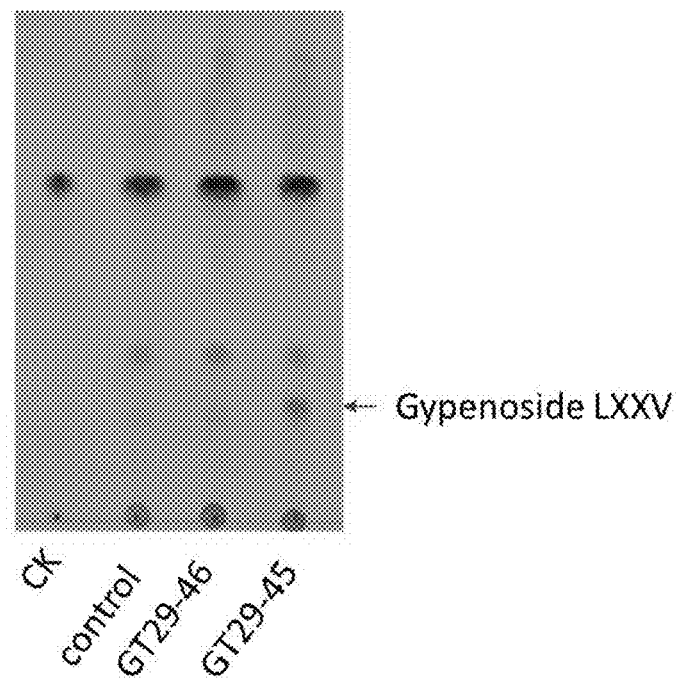

FIG. 16 shows a TLC pattern of a transglycosyl reaction catalyzed by glycosyltransferases GT29-45 and GT29-46 using ginsenoside CK as a glycosyl acceptor and UDP-glucose as a glycosyl donor. Control represents the lysate supernatant of the pet28a empty vector recombinant as an enzyme solution; GT29-45 and GT29-46 respectively represents the lysate supernatant of the recombinant *E. coli* BL21-GT29-45 and BL21-GT29-46 as an enzyme solution.

Figure 17:
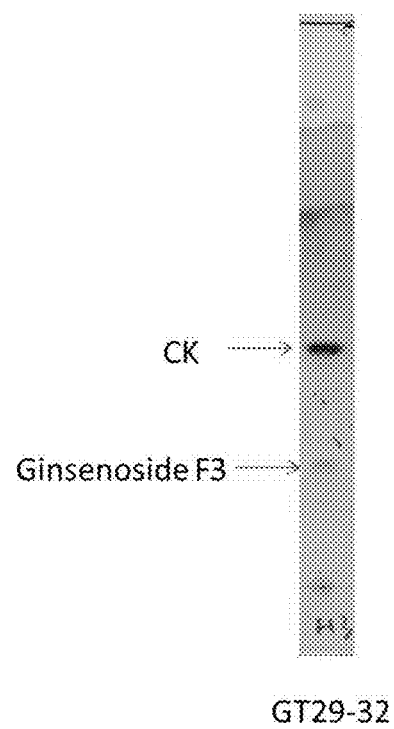

FIG. 17 shows a TLC pattern of a transglycosyl reaction catalyzed by glycosyltransferase GT29-32 using ginsenoside CK as a glycosyl acceptor and UDP-arabinose as a glycosyl donor. Control represents the lysate supernatant of the pet28a empty vector recombinant as an enzyme solution; GT29-32 represents the lysate supernatant of the recombinant *E. coli* BL21-GT29-32 as an enzyme solution.

DETAILED DESCRIPTION

After an extensive and in-depth study, the present inventors have firstly provided a new glycosyltransferase and the corresponding glycosyltransfer catalytic sites. Specifically, the glycosyltransferases GT29-32 (SEQ ID NO.: 4), GT29-33 (SEQ ID NO.: 6), GT29-34 (SEQ ID NO.: 8), GT29-4 (SEQ ID NO.: 12), GT29-5 (SEQ ID NO.: 14), GT29-7 (SEQ ID NO.: 16), GT29-9 (SEQ ID NO.: 18), GT29-11 (SEQ ID NO.: 20), GT29-13 (SEQ ID NO.: 22), GT29-17 (SEQ ID NO.: 24), GT29-18 (SEQ ID NO.: 26), GT29-19 (SEQ ID NO.: 116), GT29-20 (SEQ ID NO.:118), GT29-21 (SEQ ID NO.:120), GT29-22 (SEQ ID NO.:122), GT29-23 (SEQ ID NO.:124)), GT29-24 (SEQ ID NO.: 28), GT29-25 (SEQ ID NO.: 30), GT29-36 (SEQ ID NO.: 90), GT29-37 (SEQ ID NO.: 92), GT29-42 (SEQ ID NO.: 94), GT29-43 (SEQ ID NO.: 96), GT29-45 (SEQ ID NO.: 98), GT29-46 (SEQ ID NO.: 100), PNUGT29-1 (SEQ ID NO.: 39), PNUGT29-2 (SEQ ID NO.: 41), PNUGT29-3 (SEQ ID NO.: 43), PNUGT29-4 (SEQ ID NO.: 45), PNUGT29-5 ((SEQ ID NO.: 47), PNUGT29-6 (SEQ ID NO.: 49), PNUGT29-7 (SEQ ID NO.: 51), PNUGT29-8 (SEQ ID NO.: 53), PNUGT29-9 (SEQ ID NO.: 55), PNUGT29-14 (SEQ ID NO.: 57), PNUGT29-15 (SEQ ID NO.: 59) can specifically and efficiently catalyze the hydroxyl glycosylation of the first glycosyl group on the C-20, C-6, or C3 position of a tetracyclic triterpene compound substrate or replace the original glycosyl group with a glycosyl group to extend the carbohydrate chain.

The glycosyltransferase of the present invention is particularly capable of converting ginsenosides CK, DMG, F2, Rd, F1, Rh1, and Rg1 to ginsenoside Rg3, ginsenoside Rd, ginsenoside Rb1, ginsenoside Rb3, saponin DMGG, saponin DMGX, gypenosides LXXV, gypenosides XVII, gypenosides XIII, gypenosides IX, notoginsenoside U and notoginsenoside R1 and notoginsenoside R2, notoginsenoside R3, 3-O-β-(D-xylopyranosyl)-β-(D-glucopyranosyl)-PPD 3-O-β-(D-xylopyranosyl)-β-(D-glucopyranosyl)-CK, 20-O-Glucosylginsenoside Rf and Ginsenoside F3.

Definition

As used herein, the terms "active polypeptide", "polypeptide of the present invention and the derivative polypeptide thereof", "the enzyme of the present invention" and "glycosyltransferase" can be used interchangeably and all refer to GT29-32 (SEQ ID NO.: 4), GT29-33 (SEQ ID NO.: 6), GT29-34 (SEQ ID NO.: 8), GT29-4 (SEQ ID NO.: 12), GT29-5 (SEQ ID NO.: 14), GT29-7 (SEQ ID NO.: 16), GT29-9 (SEQ ID NO.: 18), GT29-11 (SEQ ID NO.: 20), GT29-13 (SEQ ID NO.: 22), GT29-17 (SEQ ID NO.: 24), GT29-18 (SEQ ID NO.: 26), GT29-19 (SEQ ID NO.: 116), GT29-20 (SEQ ID NO.: 118), GT29-21 (SEQ ID NO.:120), GT29-22 (SEQ ID NO.:122), GT29-23 (SEQ ID NO.:124), GT29-24 (SEQ ID NO.: 28), GT29-25 (SEQ ID NO.: 30), GT29-36 (SEQ ID NO.: 90), GT29-37 (SEQ ID NO.: 92), GT29-42 (SEQ ID NO.: 94), GT29-43 (SEQ ID NO.: 96), GT29-45 (SEQ ID NO.: 98), GT29-46 (SEQ ID NO.: 100), PNUGT29-1 (SEQ ID NO.: 39), PNUGT29-2 (SEQ ID NO.: 41), PNUGT29-3 (SEQ ID NO.: 43), PNUGT29-4 (SEQ ID NO.: 45), PNUGT29-5 (SEQ ID NO.: 47), PNUGT29-6 (SEQ ID NO.: 49), PNUGT29-7 (SEQ ID NO.: 51), PNUGT29-8 (SEQ ID NO.: 53), PNUGT29-9 (SEQ ID NO.: 55), PNUGT29-14 (SEQ ID NO.: 57), PNUGT29-15 (SEQ ID NO.: 59) polypeptides and the derivative polypeptides thereof.

As used herein, "the isolated polypeptide" or "active polypeptide" means that the polypeptide is substantially free of other proteins, lipids, carbohydrates, or other substances with which it is naturally associated. Those skilled in the art can purify the polypeptide using standard protein purification techniques. Substantially pure polypeptides can form a single main band on a non-reduced polyacrylamide gel. The purity of the polypeptide can be further analyzed using the amino acid sequence.

The active polypeptide of the present invention may be a recombinant polypeptide, a natural polypeptide, or a synthetic polypeptide. The polypeptides of the present invention may be naturally purified products or chemically synthesized products, or produced from prokaryotic or eukaryotic hosts (e.g., bacteria, yeast, plants) using recombinant techniques. Depending on the host used in the recombinant production protocol, the polypeptides of the present invention may be glycosylated or may be non-glycosylated. The polypeptides of the present invention may also include or exclude the starting methionine residue.

The present invention further provides fragments, derivatives and analogs of the polypeptides. As used herein, the terms "fragment", "derivative" and "analog" refer to a polypeptide that substantially retains the same biological function or activity of the polypeptide.

The polypeptide fragment, derivative or analog of the present invention may be (i) a polypeptide having one or more conservative or non-conservative amino acid residues (preferably conservative amino acid residues) substituted, and such substituted amino acid residues may or may not be encoded by the genetic code, or (ii) a polypeptide having a substituent group in one or more amino acid residues, or (iii) a polypeptide formed by fusion of a mature polypeptide with another compound, such as a compound that extends the half-life of the polypeptide, such as polyethylene glycol, or (iv) a polypeptide formed by fusing an additional amino acid sequence to this polypeptide sequence (such as a leader sequence or a secreted sequence or a sequence or protease sequence used to purify this polypeptide, or a fusion protein formed with an antigen IgG fragment). In accordance with the teachings herein, these fragments, derivatives, and analogs are within the scope of those skilled in the art.

The active polypeptide of the present invention has glycosyltransferase activity and can catalyze one or more of the following reactions:

Rha, Glc (6-1) Arap, Glc (6-1) Xyl, Glc (6-1) Araf, Glc (3-1) Glc (3-1), Glc (2-1) Glu (6) Ac, Glc (6-1) Arap (4-1) Xyl, Glc (6-1) Arap (2-1) Xyl, or Glc (6-1) Arap (3-1) Xyl and other polysaccharides composed of 2-4 monosaccharides.

The R1-R4 substituted compounds are shown in the table below:

| substrate | R1 | R2 | R3 | R4 | product |
|---|---|---|---|---|---|
| CK | H | OH | Glc | Glc | Gypenosides LXXV |
| DMG | H | H | Glc | Glc | DMGG |
| F2 | Glc | OH | Glc | Glc | Gypenosides XVII |
| Rd | Glc(2-1)Glc | OH | Glc | Glc | Rb1 |
| CK | H | OH | Glc | Xyl | Gypenosides XIII |
| DMG | H | H | Glc | Xyl | DMGX |
| F2 | Glc | OH | Glc | Xyl | Gypenosides IX |
| Rd | Glc(2-1)Glc | OH | Glc | Xyl | Rb3 |
| CK | H | OH | Glc | Arabinose | Ginsenoside F3 | that is, when R1 is H, R2 is OH, and R3 is a glucosyl, the compound of formula (I) is ginsenoside CK (CK);
when R1 and R2 are both H, and R3 is a glucosyl, the compound of Formula (I) is ginsenoside DMG;
when R1 is a glucosyl, R2 is OH, and R3 is a glucosyl, the compound of Formula (I) is ginsenoside F2 (F2); or
when R1 is two glucosyls (Glc (2-1) Glc), R2 is OH, and R3 is a glucosyl, the compound of Formula (I) is ginsenoside Rd;

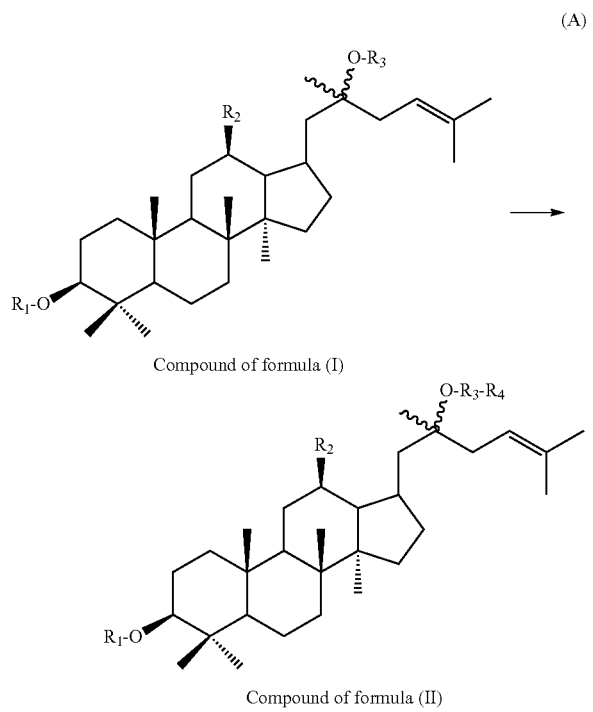

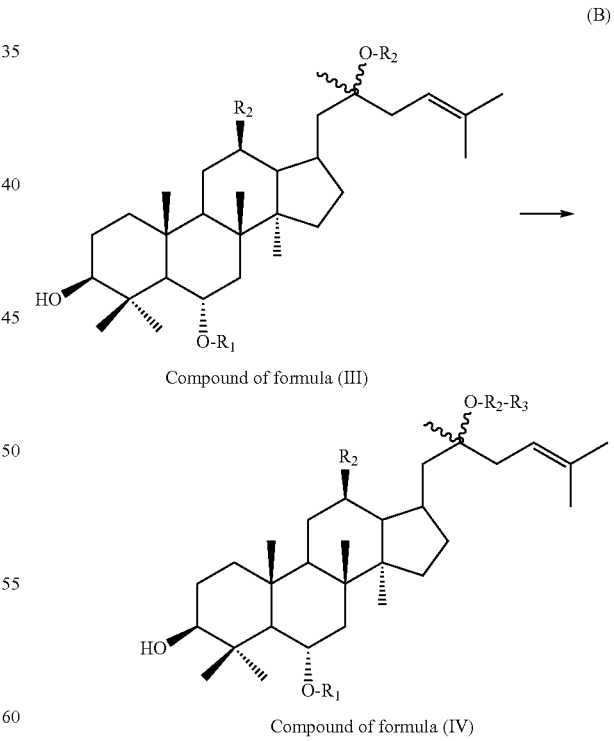

wherein R1 is H, a monosaccharide glycosyl or a polysaccharide glycosyl; R2 is H or OH; R3 is a monosaccharide glycosyl; R4 is a monosaccharide glycosyl, and the polypeptide is selected from SEQ ID NO: 4, 6, 8, 39, 41, 43, 45, 47, 49, 51, 53, 55, 57, 59, 98, 100, 116, 118, 120, 122, and 124 and a derivative polypeptide thereof.

In another preferred embodiment, the monosaccharide comprises glucose (Glc), rhamnose (Rha), acetylglucose (Glc(6)Ac), arabinofuranose (Araf), arabinopyranose (Arap), or xylose (Xyl) and the like.

In another preferred embodiment, the polysaccharide comprises Glc (2-1) Glc, Glc (6-1) Glc, Glc (6) Ac, Glc (2-1)

wherein R1 is H, a glycosyl or a polysaccharide glycosyl, R2 is a glycosyl, R3 is a glycosyl, the polypeptide is selected from SEQ ID NOs.: 4 and a derivative polypeptide thereof;

The R1-R3 substituted compounds are shown in the table below:

| substrate | R1 | R2 | R3 | product |
|---|---|---|---|---|
| F1 | H | Glc | Glc | Notoginsenoside U |
| Rg1 | Glc | Glc | Glc | Notoginsenoside R3 | that is, when R1 is H and R2 is a glucosyl, the compound of Formula (III) is ginsenoside F1 (F1); or when R1 and R2 are glucosyls, the compound of Formula (III) is ginsenoside Rg1 (Rg1);

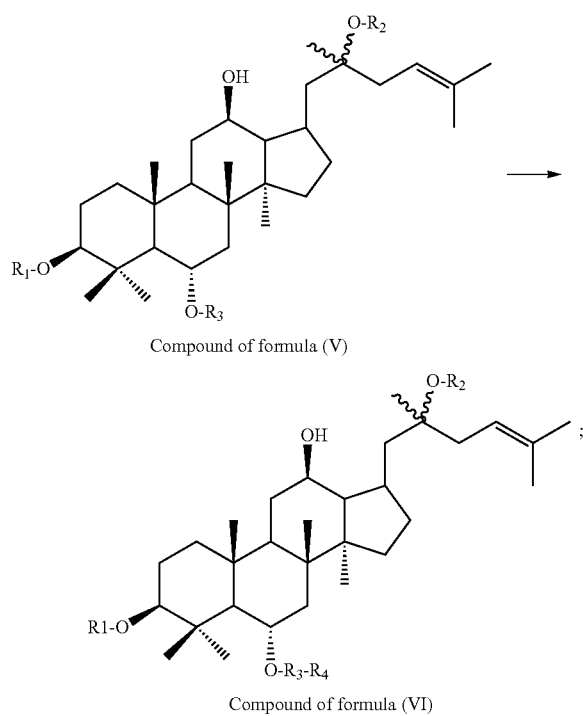

Compound of formula (V)

Compound of formula (VI)

wherein R1 and R2 are H or glycosyls, and R3 and R4 are glycosyls. The polypeptide is selected from SEQ ID NOs.: 12, 14, 16, 18, 20, 22, 24, 26, 28, 30 or a derivative polypeptide thereof;

The R1-R4 substituted compounds are shown in the table below:

| substrate | R1 | R2 | R3 | R4 | product |
|---|---|---|---|---|---|
| Rg1 | H | Glc | Glc | Xyl | Notoginsenoside R1 |
| Rg1 | H | Glc | Glc | Glc | 20-O-Glucosylginsenoside Rf |
| Rh1 | H | H | Glc | Xyl | Notoginsenoside R2 |
| Rh1 | H | H | Glc | Glc | Ginsenoside Rf | that is, when R1 is H and both R2 and R3 are glucosyls, the compound of Formula (V) is ginsenoside Rg1;

when R1 and R2 are H, and R3 is glucosyl, the compound of Formula (V) is ginsenoside Rh1.

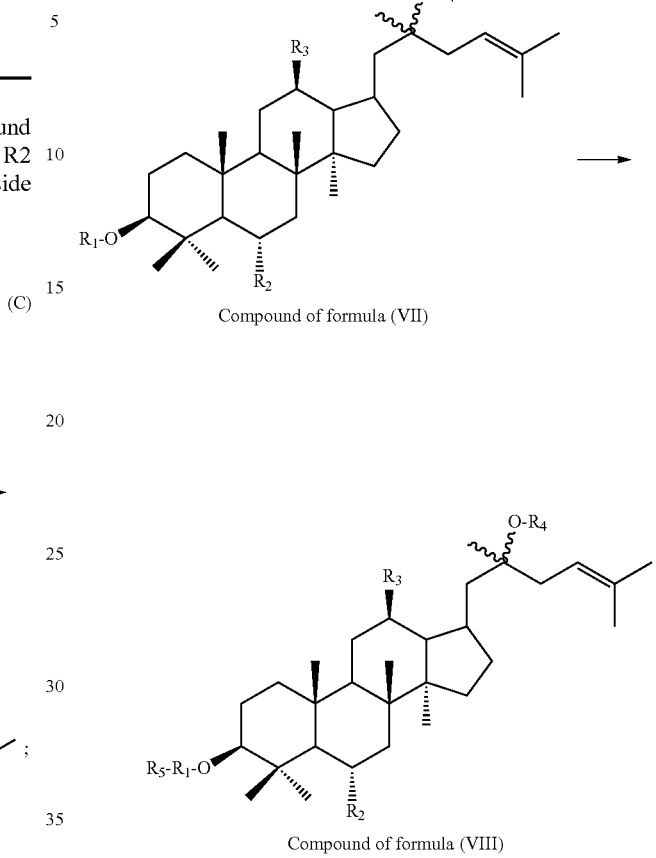

Compound of formula (VII)

Compound of formula (VIII)

wherein R1 is a glycosyl; R2 and R3 are OH or H; R4 is a glycosyl or H; R5 is a glycosyl, R5-R1-O is a glycosyl derived from the first glycosyl of C3; and the polypeptide is selected from SEQ ID NOs.: 26, 28, 30, 39, 41, 43, 45, 47, 49, 51, 53, 55, 57, 59, 98, 100, 116, 118, 120, 122, and 124 and a derivative polypeptide thereof;

| substrate | R1 | R2 | R3 | R4 | R5 | product |
|---|---|---|---|---|---|---|
| Rh2 | Glc | H | OH | H | Glc | Rg3 |
| F2 | Glc | H | OH | Glc | Glc | Rd |
| Gypenoside XVII | Glc | H | OH | Glc(6,1)Glc | Glc | Rb1 |
| Gypenoside IX | Glc | H | OH | Glc(6,1)xyl | Glc | Rb3 | that is, when R1 is a glucosyl; R2 is H, R3 is OH, R4 is H, and the compound of Formula (VII) is Rh2;

R1 is a glucosyl; R2 is H, R3 is OH, R4 is a glucosyl, and the compound of Formula (VII) is F2;

R1 is a glucosyl; R2 is H, R3 is OH, R4 is two glucosyl groups, and the compound of Formula (VII) is Gypenoside XVII;

R1 is a glucosyl; R2 is H, R3 is OH, R4 is a glucosyl extended with a xylose, the compound of Formula (VII) is Gypenoside IX;

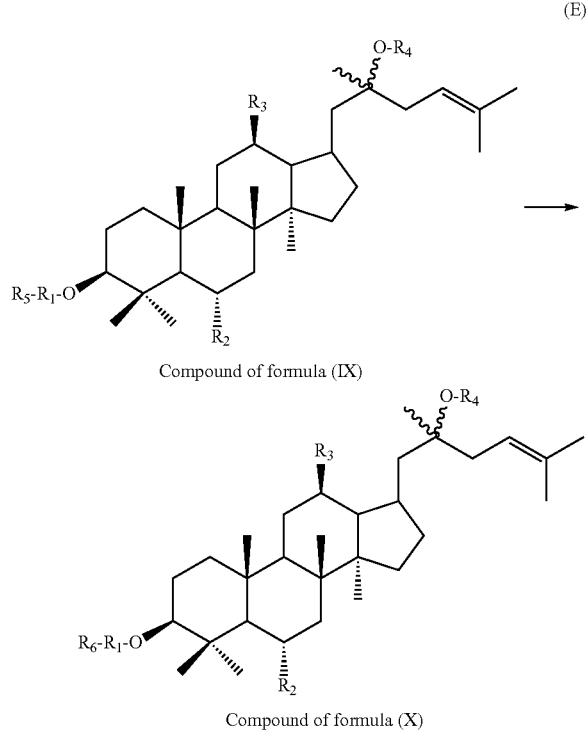

Compound of formula (IX)

Compound of formula (X)

wherein R1 is a glycosyl; R2 and R3 are OH or H; R4 is a glycosyl or H; R5 is a glycosyl and R5-R1-O is a glycosyl derived from the first glycosyl of C3; R6 is a glycosyl and R6-R1-O is a glycosyl derived from the first glycosyl of C3, and the polypeptide is selected from SEQ ID NOs.: 41, 45, 90, 92, 94, and 96 and a derivative polypeptide thereof;

R1 is two glucosyl groups, R2 is H, R3 is OH, R4 is H, and the compound of Formula (IX) is Rg3.

R1 is two glucosyl groups, R2 is H, R3 is OH, R4 is glucosyl, and the compound of Formula (IX) is Rd.

The preferred sequence of the polypeptide is as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124, and the term also includes polypeptide variants and the derived polypeptides that have the same function as the indicated polypeptides of SEQ ID NO 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124. These variant forms include (but are not limited to): one or more (usually 1-50, preferably 1-30, more preferably 1-20, most preferably 1-10) amino acid deletions, insertions and/or substitutions and the addition of one or several (usually within 20, preferably within 10, more preferably within 5) amino acids at the C-terminus and/or N-terminus. For example, in the art, the substitution of amino acids with similar or close properties usually does not change the function of the protein. As another example, adding one or several amino acids to the C-terminus and/or N-terminus usually does not change the function of the protein. The term also includes active fragments and active derivatives of the polypeptides of the present invention. The present invention also provides analogues of the polypeptides. The difference between these analogues and the natural polypeptide of the present invention may be a difference in amino acid sequence, a difference in the modification form that does not affect the sequence, or both. These polypeptides include natural or induced genetic variants. Induced variants can be obtained by various techniques, such as random mutagenesis by radiation or exposure to mutagen, or by site-directed mutagenesis or other known molecular biology techniques. Analogs also include analogs with residues different from natural L-amino acids (such as D-amino acids), and analogs with non-naturally occurring or synthetic amino acids (such as (3, y-amino acids). It should be understood that the polypeptide of the present invention is not limited to the representative polypeptides exemplified above.

Modified (usually without changing the primary structure) forms include: in vivo or in vitro chemically derived forms of the polypeptide such as acetylation or carboxylation. Modifications also include glycosylation, such as those produced by glycosylation modification during the synthesis and processing of polypeptides or during further processing steps. This modification can be accomplished by exposing the polypeptide to an enzyme that performs glycosylation (such as mammalian glycosylation or deglycosylation enzymes). Modified forms also include sequences with phosphorylated amino acid residues (e.g., phosphotyrosine, phosphoserine, phosphothreonine). Also included are peptides that have been modified to improve their proteolytic resistance or optimize their solubility. The amino or carboxyl terminus of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 protein of the present invention may also contain one or more polypeptide fragments as protein tags. Any suitable tags can be used in the present invention. For example, the tags may be FLAG, HA, HA1, c-Myc, Poly-His, Poly-Arg, Strep-TagII, AU1, EE, T7, 4A6, c, B, gE, and Tyl. These tags can be used to purify proteins. Table 1 lists some of the commercially available tags.

TABLE 1

| tag | number of residues |
| --- | --- |
| Poly-Arg | 5-6 (usually 5) |
| Poly-His | 2-10 (usually 6) |
| FLAG | 8 |
| Strep-TagII | 8 |
| C-myc | 10 |
| GST | 220 |

In order to make the translated protein secreted and expressed (such as secreted out of the cell), a signal peptide sequence, such as pelB signal peptide and the like can be added to the amino terminus of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15. The signal peptide can be cleaved during the secretion of the polypeptide from the cell.

The polynucleotide of the present invention may be in the form of DNA or RNA. DNA form includes cDNA, genomic DNA, or synthetic DNA. DNA can be single-stranded or double-stranded. DNA can be a coding strand or a non-coding strand. The coding region sequence encoding the mature polypeptide can be the same with the coding region sequence as shown in SEQ ID NO.: 3, 5, 7, 11, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123 or degenerate variants. As used herein, "degenerate variant" in the present invention refers to a nucleic acid sequence encoding the protein having SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124, but differing in the coding region sequences as shown in SEQ ID NO.: 3, 5, 7, 11, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123, respectively.

Polynucleotides encoding mature polypeptides of SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 include: coding sequences encoding mature polypeptides only; coding sequences encoding mature polypeptides and various additional coding sequences; mature polypeptide coding sequences (and optional additional coding sequences) and non-coding sequences.

The term "polynucleotide encoding a polypeptide" may include a polynucleotide encoding the polypeptide, or a polynucleotide further including additional coding and/or non-coding sequences.

The present invention also relates to variants of the aforementioned polynucleotides, which encode fragments, analogues and derivatives of polypeptides or polypeptides having the same amino acid sequence as the present invention. This polynucleotide variant may be a naturally occurring allelic variant or a non-naturally occurring variant. These nucleotide variants include substitution variants, deletion variants and insertion variants. As known in the art, an allelic variant is a form of substitution of a polynucleotide. It may be a substitution, deletion, or insertion of one or more nucleotides, but it will not substantially change the function of the polypeptide encoded.

The present invention also relates to polynucleotides that hybridize to the above-mentioned sequences and have at least 50%, preferably at least 70%, more preferably at least 80%, 85%, 90%, 95% identity between the two sequences. The present invention particularly relates to polynucleotides that can hybridize to the polynucleotides of the present invention under stringent conditions (or stringent conditions). In the present invention, "stringent conditions" means: (1) hybridization and elution at a lower ionic strength and higher temperature, such as 0.2×SSC, 0.1% SDS, 60° C.; or (2) added with denaturing agents during hybridization, such as 50% (v/v) formamide, 0.1% calf serum/0.1% Ficoll, 42° C., etc.; or (3) hybridization only when the identity between the two sequences is at least 90%, more preferably at least 95%. Furthermore, the polypeptides encoded by the hybridizable polynucleotides have the same biological function and activity as the mature polypeptides as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124.

The present invention also relates to a nucleic acid fragment hybridized to the aforementioned sequences. As used herein, "nucleic acid fragment" contains at least 15 nucleotides in length, preferably at least 30 nucleotides, more preferably at least 50 nucleotides, and most preferably at least 100 nucleotides or more. Nucleic acid fragments can be used in nucleic acid amplification techniques (such as PCR) to determine and/or isolate polynucleotides encoding GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 protein.

The polypeptide and polynucleotide in the present invention are preferably provided in an isolated form, and are more preferably purified to homogeneity.

A full-length nucleotide sequence or fragment thereof of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 of the present invention can usually be obtained by PCR amplification method, recombination method or artificial synthesis method. For the PCR amplification method, primers can be designed according to the relevant nucleotide sequence disclosed in the present invention, especially the open reading frame sequence, and a commercially available cDNA library or cDNA library prepared according to conventional methods known to those skilled in the art is used as a 25 template to amplify and obtain the relevant sequences. When the sequence is long, it is often necessary to perform two or more PCR amplifications, and then splice the amplified fragments together in the correct order.

Once the relevant sequence is obtained, the relevant sequence can be obtained in large quantities by the recombination method. This is usually done by cloning it into a vector, then transferring it into cells, and then isolating and obtaining the relevant sequence from the proliferated host cells by conventional methods.

In addition, artificial synthetic methods can be used to synthesize the relevant sequences, especially when the length of the fragments is short. Generally, a long sequence can be obtained by synthesizing multiple small fragments and then connecting them.

At present, the DNA sequence encoding the protein (or fragment or derivative thereof) of the present invention can be obtained completely by chemical synthesis. This DNA sequence can then be introduced into various existing DNA molecules (or such as vectors) and cells known in the art. In addition, mutations can also be introduced into the protein sequence of the present invention by chemical synthesis.

The method of amplifying DNA/RNA using PCR technology is preferably used to obtain the gene of the present invention. Especially when it is difficult to obtain full-length cDNA from the library, the RACE method (RACE-cDNA terminal rapid amplification method) can be preferably used, and the primers used for PCR can be appropriately selected based on the sequence information of the present invention disclosed herein, and can be synthesized by conventional methods. The amplified DNA/RNA fragments can be separated and purified by conventional methods such as gel electrophoresis.

The present invention also relates to a vector comprising the polynucleotide of the present invention, and a host cell produced by genetic engineering using the vector of the present invention or the protein coding sequence of GT29-32, GT29-33, GT29-34, GT29-4, GT29-5, GT29-7, GT29-9, GT29-11, GT29-13, GT29-17, GT29-18, GT29-19, GT29-

20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15, and the method of producing the polypeptide of the present invention by recombinant technology.

Through the conventional recombinant DNA technology, the polynucleotide sequence of the present invention can be used to express or produce recombinant GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 polypeptide.

Generally speaking, there are the following steps:

(1). transforming or transducing a suitable host cell with a polynucleotide (or a variant) encoding a polypeptide of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9. PNUGT29-14 or PNUGT29-15 of the present invention, or with a recombinant expression vector containing the polynucleotide;

(2). culturing a host cell in a suitable medium;

(3). isolating and purifying proteins from culture medium or cells.

In the present invention, polynucleotide sequences of GT29-32, GT29-33, GT29-34, GT29-4, GT29-5, GT29-7, GT29-9, GT29-11, GT29-13, GT29-17, GT29-18, GT29 19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15 can be inserted into recombinant expression vectors. The term "recombinant expression vector" refers to a bacterial plasmid, bacteriophage, a yeast plasmid, plant cell virus, mammalian cell virus such as adenovirus, retrovirus, or other vectors well known in the art. As long as it can replicate and stabilize in the host, any plasmid and vector can be used. An important feature of expression vectors is that they usually contain an origin of replication, a promoter, a marker gene and a translation control element.

Methods well known to those skilled in the art can be used to construct expression vectors containing GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15 encoding DNA sequences and appropriate transcription/translation control signals. These methods include in vitro recombinant DNA technology, DNA synthesis technology, in vivo recombinant technology and the like. The DNA sequence can be effectively linked to an appropriate promoter in an expression vector to guide mRNA synthesis. Representative examples of these promoters are: lac or trp promoters of $E.\ coli$; λ phage PL promoters; eukaryotic promoters including CMV immediate early promoters, HSV thymidine kinase promoters, early and late SV40 promoters, retroviral LTRs and other known promoters that control gene expression in prokaryotic or eukaryotic cells or their viruses. The expression vector also includes a ribosome binding site for translation initiation and a transcription terminator.

In addition, the expression vector preferably contains one or more selectable marker genes to provide phenotypic traits for selection of transformed host cells, such as dihydrofolate reductase, neomycin resistance, and green fluorescent protein (GFP) for eukaryotic cell culture, or tetracycline or ampicillin resistance for $E.\ coli$.

Vectors containing the appropriate DNA sequences and appropriate promoters or control sequences as described above can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are: *E. coli, Streptomyces*; bacterial cells of *Salmonella typhimurium*; fungal cells such as yeast; plant cells; insect cells of *Drosophila* S2 or Sf9; animal cells such as CHO, COS, 293 cells, or Bowes melanoma cells and the like.

When the polynucleotide of the present invention is expressed in higher eukaryotic cells, if an enhancer sequence is inserted into the vector, transcription will be enhanced. Enhancers are cis-acting factors of DNA, usually about 10 to 300 base pairs, which act on the promoter to enhance gene transcription. Examples include 100 to 270 base pair of SV40 enhancers on the late side of the replication start point, polyoma enhancers on the late side of the replication start point, and adenovirus enhancers.

Those of ordinary skill in the art know how to select appropriate vectors, promoters, enhancers and host cells.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the $CaCl_2$ method. The procedures used are well known in the art. Another method is to use $MgCl_2$. If necessary, transformation can also be carried out by electroporation. When the host is a eukaryote, the following DNA transfection methods can be used: calcium phosphate co-precipitation method, conventional mechanical methods such as microinjection, electroporation, liposome packaging, etc.

The obtained transformant can be cultured by a conventional method and express the polypeptide encoded by the gene of the present invention. Depending on the host cell used, the medium used in the culture can be selected from various conventional mediums. The cultivation is carried out under conditions suitable for the growth of host cells. When the host cell grows to an appropriate cell density, the selected promoter is induced by an appropriate method (such as temperature conversion or chemical induction), and the cell is cultured for a period of time.

The recombinant polypeptide in the above method may be expressed in a cell, on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, bacteria disruption through osmosis, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

Use

The active polypeptide or glycosyltransferase involved in the present invention can be used to artificially synthesize known ginsenosides and new ginsenosides and the derivatives thereof, and can convert CK, DMG, F2, Rd, F1, Rh1 and Rg1 into ginsenoside Rg3, ginsenoside Rd, ginsenoside Rb1, ginsenoside Rb3, saponin DMGG, saponin DMGX, Gypenosides LXXV, Gypenosides XVII, Gypenosides XIII, Gypenosides IX, notoginsenoside U and, notoginsenoside R1, and notoginsenoside R2, notoginsenoside R3, 3-O-β-(D-xylopyranosyl)-β-(D-glucopyranosyl)-PPD; 3-O-β-(D-xylopyranosyl)-β-(D-glucopyranosyl)-CK, 20-O-Glucosylginsenoside Rf and Ginsenoside F3.

The Main Advantages of the Invention:

(1) The glycosyltransferase of the present invention can specifically and efficiently transfer a glycosyl or replace a glycosyl on the first glycosyl on the C-20 position/or the first glycosyl on the C-6 or C-3 position of the substrate of the tetracyclic triterpene compound to extend the carbohydrate chain;

(2) The glycosyltransferase of the present invention is particularly capable of converting CK, DMG, F2, Rd, F1, Rh1 and Rg1 into active ginsenoside Rg3, ginsenoside Rd, ginsenoside Rb1, ginsenoside Rb3, saponin DMGG, Saponin DMGX, Gypenosides LXXV, Gypenosides XVII, Gypenosides XIII, Gypenosides IX, notoginsenoside U, notoginsenoside R1, and notoginsenoside R2, notoginsenoside R3, 3-O-β-(D-xylopyranosyl)-β-(D-glucopyranosyl)-PPD; 3-O-β-(D-xylopyranosyl)-β-(D-glucopyranosyl)-CK, 20-O-Glucosylginsenoside Rf and Ginsenoside F3.

(3) Ginsenoside Rb1 has the effect of protecting nerve cells and anti-inflammatory and antioxidant; and ginsenoside Rb3 has the effect of alleviating myocardial ischemia and anti-depression. Notoginsenoside R1 is the main active ingredient of notoginsenoside with anti-inflammatory effects. Notoginsenoside R2 has a neuroprotective effect.

Example 1 Isolation of Ginseng Glycosyltransferase and the Coding Gene Thereof

Ginseng RNA was extracted and reverse transcription was performed to obtain ginseng cDNA. PCR amplification was performed using primer pair 1 (SEQ ID NO.: 1 and SEQ ID NO.: 2) or primer pair 2 (SEQ ID NO.: 9 and SEQ ID NO.: 10) or primer pair 3 (SEQ ID NO.: 113 and SEQ ID NO.: 114) using this cDNA as a template to obtain a 1.4-1.5 kb amplification product. The high-fidelity KOD DNA polymerase from Bao Bioengineering Co., Ltd. was used as the DNA polymerase. PCR products were detected by agarose gel electrophoresis.

The target DNA band was cut off under UV irradiation. Then the Axygen Gel Extraction Kit (AEYGEN) was used to recover DNA from the agarose gel, that is, the amplified DNA fragment. After A was added at the end of this DNA fragment using rTaq DNA polymerase from Bao Bioengineering Co., Ltd., it was ligated with the commercially available cloning vector pMD18-T Vector, and the ligation product was transformed into commercially available E. coli EPI300 competent cells. The transformed E. coli solution was coated on LB plates supplemented with AMP 50 ug/mL, IPTG 0.5 mM, X-Gal 25 μg/mL, and the recombinant clone was further verified by PCR and enzyme digestion. Several clones were selected and the recombinant plasmids were extracted and sequenced to obtain 29 different nucleic acid sequences, named GT29-32 (SEQ ID NO.: 3), GT29-33 (SEQ ID NO.: 5), GT29-34 (SEQ ID NO.: 7), GT29-4 (SEQ ID NO.: 11), GT29-5 (SEQ ID NO.: 13), GT29-7 (SEQ ID NO.: 15), GT29-9 (SEQ ID NO.: 17), GT29-11 (SEQ ID NO.: 19), GT29-13 (SEQ ID NO.: 21), GT29-17 (SEQ ID NO.: 23), GT29-18 (SEQ ID NO.: 25), GT29-19 (SEQ ID NO.: 116), GT29-20 (SEQ ID NO.: 118), GT29-21 (SEQ ID NO.: 120), GT29-22 (SEQ ID NO.: 122)), GT29-23 (SEQ ID NO.: 124), GT29-24 (SEQ ID NO.: 27), GT29-25 (SEQ ID NO.: 29), GT29-36 (SEQ ID NO.: 89), GT29-37 (SEQ ID NO.: 91), GT29-42 (SEQ ID NO.: 93), GT29-42 (SEQ ID NO.: 95), GT29-45 (SEQ ID NO.: 97) and GT29-46 (SEQ ID NO.: 99), respectively. Using BESTORF software to find ORF. Through sequence alignment, it was found that the extension products all have the conserved functional domain of glycosyltransferase family 1, indicating that it is a glycosyltransferase gene.

GT29-32: The glycosyltransferase gene GT29-32 encodes a protein GT29-32 containing 442 amino acids and has the amino acid sequence as shown in SEQ ID NO: 4 in the sequence listing. The theoretical molecular weight of this protein is predicted to be 49.2 kDa by software, and the isoelectric point pI is 6.09. The amino acid sequence identity between the glycosyltransferase and the functionally identified glycosyltransferase UGTPg29 (Genbank accession AKA44579.1) is 92%.

GT29-33: The glycosyltransferase gene GT29-33 encodes a protein GT29-33 containing 448 amino acids with the amino acid sequence as shown in SEQ ID NO: 6 in the sequence listing. The theoretical molecular weight of the protein is predicted to be 50.0 kDa by software, and the isoelectric point pI is 6.77. The amino acid sequence identity between the glycosyltransferase and the functionally identified glycosyltransferase UGTPg29 is 90%.

GT29-34: The glycosyltransferase gene GT29-34 encodes a protein GT29-34 containing 446 amino acids and has the amino acid sequence as shown in SEQ ID NO: 8 in the sequence listing. The theoretical molecular weight of the protein is predicted to be 49.7 kDa by software, and the isoelectric point pI is 6.23. The amino acid sequence identity between the glycosyltransferase and the functionally identified glycosyltransferase UGTPg29 is 90%.

GT29-4: The glycosyltransferase gene GT29-4 encodes a protein GT29-4 containing 446 amino acids with the amino acid sequence as shown in SEQ ID NO: 12 in the sequence listing. The theoretical molecular weight of the protein is predicted to be 49.8 kDa by software, and the isoelectric point pI is 5.63. The amino acid sequence identity between the glycosyltransferase and the functionally identified glycosyltransferase UGTPg29 is 92%.

GT29-5: The glycosyltransferase gene GT29-5 encodes a protein GT29-5 containing 446 amino acids with the amino acid sequence as shown in SEQ ID NO: 14 in the sequence listing. The theoretical molecular weight of the protein is predicted to be 49.7 kDa by software, and the isoelectric point pI is 5.93. The amino acid sequence identity between the glycosyltransferase and the functionally identified glycosyltransferase UGTPg29 is 93%.

GT29-7: The glycosyltransferase gene GT29-7 encodes protein GT29-7 containing 446 amino acids with the amino acid sequence as shown in SEQ ID NO: 16 in the sequence listing. The theoretical molecular weight of the protein is predicted to be 49.8 kDa by software, and the isoelectric point pI is 5.8. The amino acid sequence identity between the glycosyltransferase and the functionally identified glycosyltransferase UGTPg29 is 92%.

GT29-9: The glycosyltransferase gene GT29-9 encodes a protein GT29-9 containing 446 amino acids with the amino acid sequence as shown in SEQ ID NO: 18 in the sequence listing. The theoretical molecular weight of this protein is predicted to be 49.8 kDa by software, and the isoelectric point pI is 5.93. The amino acid sequence identity between the glycosyltransferase and the functionally identified glycosyltransferase UGTPg29 is 92%.

GT29-11: The glycosyltransferase gene GT29-11 encodes a protein GT29-11 containing 446 amino acids with the amino acid sequence as shown in SEQ ID NO: 20 in the sequence listing. The theoretical molecular weight of the protein is predicted to be 49.9 kDa by software, and the isoelectric point pI is 5.90. The amino acid sequence identity between the glycosyltransferase and the functionally identified glycosyltransferase UGTPg29 is 91%.

GT29-13: The glycosyltransferase gene GT29-13 encodes a protein GT29-13 containing 446 amino acids with the amino acid sequence as shown in SEQ ID NO: 22 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-17: The glycosyltransferase gene GT29-17 encodes a protein GT29-17 containing 442 amino acids with the amino acid sequence as shown in SEQ ID NO: 24 in the sequence listing. The theoretical molecular weight of the protein is predicted to be 49.3 kDa by software, and the isoelectric point pI is 5.35. The amino acid sequence identity between the glycosyltransferase and the functionally identified glycosyltransferase UGTPg29 is 93%.

GT29-18: The glycosyltransferase gene GT29-18 encodes a protein GT29-18 containing 446 amino acids with the amino acid sequence as shown in SEQ ID NO: 26 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-24: The glycosyltransferase gene GT29-24 encodes a protein GT29-24 containing 446 amino acids with the amino acid sequence as shown in SEQ ID NO: 28 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-25: The glycosyltransferase gene GT29-25 encodes a protein GT29-25 containing 446 amino acids with the amino acid sequence as shown in SEQ ID NO: 30 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-19: The glycosyltransferase gene GT29-19 encodes a protein GT29-19 containing 442 amino acids with the amino acid sequence as shown in SEQ ID NO: 116 in the sequence listing. The theoretical molecular weight of the protein is predicted to be 49.1 kDa by software, and the isoelectric point pI is 5.47.

GT29-20: The glycosyltransferase gene GT29-20 encodes a protein GT29-20 containing 442 amino acids with the amino acid sequence as shown in SEQ ID NO: 118 in the sequence listing. The theoretical molecular weight of the protein is predicted to be 49.1 kDa by software, and the isoelectric point pI is 5.93.

GT29-21: The glycosyltransferase gene GT29-21 encodes a protein GT29-21 containing 442 amino acids with the amino acid sequence as shown in SEQ ID NO: 120 in the sequence listing. The theoretical molecular weight of the protein is predicted to be 49.1 kDa by software, and the isoelectric point pI is 5.80.

GT29-22: The glycosyltransferase gene GT29-22 encodes a protein GT29-22 containing 442 amino acids with the amino acid sequence as shown in SEQ ID NO: 122 in the sequence listing. The theoretical molecular weight of the protein is predicted to be 49.1 kDa by software, and the isoelectric point pI is 5.93.

GT29-23: The glycosyltransferase gene GT29-23 encodes a protein GT29-23 containing 442 amino acids with the amino acid sequence as shown in SEQ ID NO: 124 in the sequence listing. The theoretical molecular weight of the protein is predicted to be 49.0 kDa by software, and the isoelectric point pI is 5.61.

GT29-36: The glycosyltransferase gene GT29-36 encodes a protein GT29-36 containing 442 amino acids with the amino acid sequence as shown in SEQ ID NO:102 in the sequence listing. The theoretical molecular weight of the protein is predicted to be 49.1 kDa by software, and the isoelectric point pI is 5.93.

GT29-37: The glycosyltransferase gene GT29-37 encodes a protein GT29-37 containing 442 amino acids with the amino acid sequence as shown in SEQ ID NO: 104 in the sequence listing. The theoretical molecular weight of the protein is predicted to be 49.1 kDa by software, and the isoelectric point pI is 5.62.

GT29-42: The glycosyltransferase gene GT29-42 encodes a GT29-42 protein containing 444 amino acids with the amino acid sequence as shown in SEQ ID NO: 106 in the sequence listing. The theoretical molecular weight of the protein is predicted to be 49.4 kDa by software, and the isoelectric point pI is 6.16.

GT29-43: The glycosyltransferase gene GT29-43 encodes a protein GT29-43 containing 442 amino acids with the amino acid sequence as shown in SEQ ID NO: 108 in the sequence listing. The theoretical molecular weight of the protein is predicted to be 49.1 kDa by software, and the isoelectric point pI is 5.78.

GT29-45: The glycosyltransferase gene GT29-45 encodes a protein GT29-45 containing 448 amino acids with the amino acid sequence as shown in SEQ ID NO: 110 in the sequence listing. The theoretical molecular weight of the protein is predicted to be 50.0 kDa by software, and the isoelectric point pI is 7.25.

GT29-46: The glycosyltransferase gene GT29-46 encodes a protein GT29-46 containing 442 amino acids with the amino acid sequence as shown in SEQ ID NO: 112 in the sequence listing. The theoretical molecular weight of this protein is predicted to be 49.1 kDa by software, and the isoelectric point pI is 5.48.

Example 2 Expression of Glycosyltransferase Genes GT29-32, GT29-33 and GT29-34 in *E. coli*

Using the plasmids GT29-32-pMD18T, GT29-33-pMD18T and GT29-34-pMD18T constructed in Example 1 containing GT29-32, GT29-33 and GT29-34 genes as templates, the target genes GT29-32, GT29-33 and GT29-34 were amplified with the primers as shown in Table 1.

Figure 1:
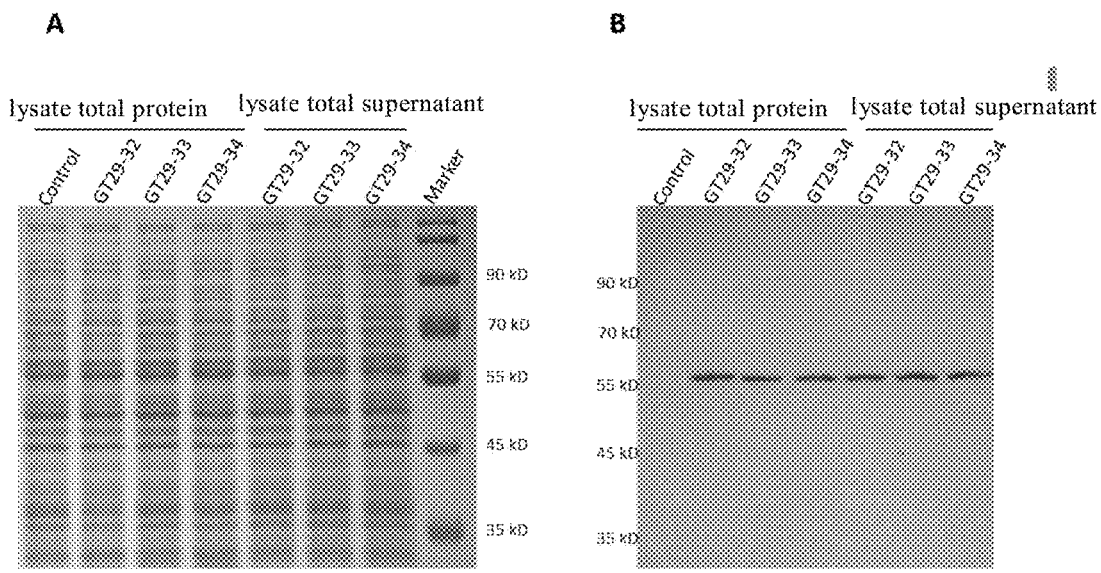
FIG. 1 (A) shows the expression shown by SDS-PAGE of glycosyltransferase genes GT29-32, GT29-33, and GT29-34 in *E. coli*; lane control represents total protein of lysate or lysis supernatant of empty vector recombinant pet28a; lane GT29-32 represents total protein or lysis supernatant of recombinant *E. coli* BL21-GT29-32; lane GT29-33 represents total protein or lysis supernatant of recombinant *E. coli* BL21-GT29-33; lane GT29-34 represents total protein of lysate or lysis supernatant of recombinant *E. coli* BL21-GT29-34; (B) shows the expression shown by Western Blot of glycosyltransferase genes GT29-32, GT29-33 and GT29-34 in *E. coli*; lane control represents total protein of lysate or lysis supernatant of empty vector recombinant pet28a; lane GT29-32 represents total protein of lysate or lysis supernatant of recombinant *E. coli* BL21-GT29-32; lane GT29-33 represents total protein of lysate or lysis supernatant of recombinant *E. coli* BL21-GT29-33; lane GT29-34 represents total protein of lysate or lysis supernatant of recombinant *E. coli* BL21-GT29-34.

After the expression vector pET28a (purchased from Merck) was digested with NcoI/SalI, GT29-32, GT29-33 and GT29-34 were cloned into pET28a (one-step cloning kit, purchased from Novizan) to construct E. coli expression vectors GT29-32-pET28a, GT29-33-pET28a and GT29-34-pET28a. Using the 6×His tag sequence on pET28a, the C-terminus of the recombinant proteins GT29-32, GT29-33 and GT29-34 had a 6×His tag. The plasmids were transformed into commercially available E. coli BL21 to construct recombinant strains BL21-GT29-32, BL21-GT29-33 and BL21-GT29-34. A recombinant was inoculated into LB medium, cultured at 37° C., 200 rpm to an OD600 of about 0.6-0.8, then the bacterial solution was cooled to 4° C., and IPTG with a final concentration of 100 μM was added, and the expression was induced at 18° C., 120 rpm for 16 h. The bacteria was collected by centrifugation at 4° C., and the cells were disrupted by ultrasound. The supernatant of the cell lysate was collected by centrifugation at 12000 g, at 4° C. for 10 min. The samples were taken for SDS-PAGE electrophoresis and western blot. SDS-PAGE result shows that the recombinant transformants of GT29-32-pET28a, GT29-33-pET28a and GT29-34-pET28a are not significantly different from the cell lysate of the empty vector pET28a recombinant transformant, and the soluble expression is not obvious (FIG. 1A). Anti-6×His tag Western Blot (FIG. 1B) shows that there is a clear band between 45 and 55 kD, and the glycosyltransferases GT29-32, GT29-33, and GT29-34 are slightly solubly expressed in E. coli.

TABLE 1 primers used to amplify genes

| gene | primer | SEQ ID NO. |
| --- | --- | --- |
| UGT29-4 | UGT29-4-F | 31 |
| | UGT29-4-R | 34 |
| UGT29-5 | UGT29-5-F | 33 |
| | UGT29-5-R | 32 |
| UGT29-7 | UGT29-7-F | 35 |
| | UGT29-7-R | 32 |
| UGT29-9 | UGT29-9-F | 33 |
| | UGT29-9-R | 32 |
| UGT29-11 | UGT29-11-F | 33 |
| | UGT29-11-R | 32 |
| UGT29-13 | UGT29-13-F | 33 |
| | UGT29-13-R | 32 |
| UGT29-17 | UGT29-17-F | 31 |
| | UGT29-17-R | 32 |
| UGT29-18 | UGT29-18-F | 33 |
| | UGT29-18-R | 34 |
| UGT29-24 | UGT29-24-F | 33 |
| | UGT29-24-R | 34 |
| UGT29-25 | UGT29-25-F | 33 |
| | UGT29-25-R | 32 |
| UGT29-32 | UGT29-32-F | 31 |
| | UGT29-32-R | 32 |
| UGT29-33 | UGT29-33-F | 36 |
| | UGT29-33-R | 37 |
| UGT29-34 | UGT29-34-F | 36 |
| | UGT29-34-R | 34 |
| UGT29-19 | UGT29-19-F | 125 |
| | UGT29-19-R | 126 |
| UGT29-20 | UGT29-20-F | 127 |
| | UGT29-20-R | 128 |
| UGT29-21 | UGT29-21-F | 129 |
| | UGT29-21-R | 130 |
| UGT29-22 | UGT29-22-F | 131 |
| | UGT29-22-R | 132 |
| UGT29-23 | UGT29-23-F | 133 |
| | UGT29-23-R | 134 |

TABLE 1-continued primers used to amplify genes

| gene | primer | SEQ ID NO. |
| --- | --- | --- |
| UGT29-36 | UGT29-36-F | 101 |
| | UGT29-36-R | 102 |
| UGT29-37 | UGT29-37-F | 103 |
| | UGT29-37-R | 104 |
| UGT29-42 | UGT29-42-F | 105 |
| | UGT29-42-R | 106 |
| UGT29-43 | UGT29-43-F | 107 |
| | UGT29-43-R | 108 |
| UGT29-45 | UGT29-36-F | 109 |
| | UGT29-36-R | 110 |
| UGT29-46 | UGT29-36-F | 111 |
| | UGT29-36-R | 112 |

Example 3 In Vitro Transglycosylation Activity and Product Identification of GT29-32, GT29-33 and GT29-34

The cell lysate supernatants of recombinant E. coli BL21-GT29-32, BL21-GT29-33 and BL21-GT29-34 in Example 2 was used as a crude enzyme solution to perform transglycosylation reaction, and the cell lysate of the recombinant E. coli with empty vector pET28a was used as a control.

As shown in FIG. 2: using protopanaxadiol ginsenoside CK as a glycosyl receptor and UDP-glucose as a glycosyl donor, GT29-32 and GT29-34 can catalyze the formation of a new product;

As shown in FIG. 3: using ginsenoside Rd as a glycosyl acceptor and UDP-glucose as a glycosyl donor, GT29-32, GT29-33 and GT29-34 can catalyze the formation of Rb1. The HPLC results are consistent with the TLC results.

Therefore, GT29-32 and GT29-34 can catalyze the C20-O-Glc of CK extension to a molecule of glucose to generate ginsenoside Gypenoside LXXV. When UDP-xylose is used as a glycosyl donor, GT29-32 can catalyze Rd to produce three products. One of the products has the same mobility on TLC as Rb3, that is, GT29-32 can extend a molecule of xylose at C20-O-Glc to produce Rb3 (FIG. 2). The results of HPLC are consistent with those of TLC. GT29-32 catalyzes the production of three products from Rd and UDP-xylose (FIG. 4).

Using Protopanaxatriol Ginsenoside F1 as a glycosyl acceptor and UDP-glucose as a glycosyl donor, GT29-32 can catalyze the formation of a new product. It is speculated that it also extends a molecule of glucose at C20-O-Glc of F1, the product is Notoginsenoside R3 (FIG. 5 and FIG. 6).

Using Protopanaxadiol Ginsenoside CK as a glycosyl acceptor and UDP-arabinose as a glycosyl donor, GT29-32, GT29-33 and GT29-34 can catalyze the first glycosyl of C-20 of CK to extend an arabinosyl to generate Ginsenoside F3, wherein GT29-32 has the strongest activity (FIG. 17).

Example 4 Expression of Glycosyltransferase Genes GT29-4, GT29-5, GT29-7, GT29-9, GT29-11, GT29-13, GT29-17, GT29-18, GT29-24 and GT29-25 in E. coli Plasmids GT29-4-pMD18T, GT29-5-pMD18T, GT29-7-pMD18T, GT29-9-pMD18T, GT29-11-pMD18T, GT29-13-pMD18T, GT29-17-pMD18T, GT29-18-pMD18T, GT29-24-pMD18T and GT29-25-pMD18T containing GT29-4, GT29-5, GT29-7, GT29-9, GT29-11, GT29-13, GT29-17, GT29-18, GT29-24 and GT29-25 genes constructed in Example 1 were used as templates to amplify target genes GT29-4, GT29-5, GT29-7, GT29-9, GT29-11, GT29-13, GT29-17, GT29-18, GT29-24 and GT29-25 with the primers as shown in Table 1. After the expression vector pET28a (purchased from Merck) was digested with NcoI/SalI, GT29-11, GT29-13, GT29-17, GT29-18, GT29-24 and GT29-25 were cloned into pET28a (one-step cloning kit, purchased from Novizan), and *E. coli* expression vectors GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24-pET28a and GT29-25-pET28a were constructed.

Using the 6×His tag sequence on pET28a, recombinant proteins GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24 and GT29-25 had a 6×His tag at the C-terminal. The plasmids were transformed into commercially available *E. coli* BL21 to construct recombinant strains BL21-GT29-4, BL21-GT29-5, BL21-GT29-7, BL21-GT29-9, BL21-GT29-11, BL21-GT29-13. BL21-GT29-17, BL21-GT29-18, BL21-GT29-24 and BL21-GT29-25. A recombinant was inoculated into LB medium, cultured at 37° C., 200 rpm to an OD600 of about 0.6-0.8, then the bacterial solution was cooled to 4° C., and IPTG with a final concentration of 100 µM was added, and induced expression was performed at 18° C., 120 rpm for 16 h. The bacteria was collected by centrifugation at 4° C., and the cells were disrupted by ultrasound. The supernatant of the cell lysate was collected by centrifugation at 12000 g at 4° C. for 10 min. The samples were taken for SDS-PAGE electrophoresis and western blot.

SDS-PAGE shows recombinant transformants of GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24-pET28a and GT29-25-pET28a were not significantly different from the cell lysate of the empty vector pET28a recombinant transformant, and the soluble expression levels were not obvious. Anti-6×His tag Western Blot shows that there was a clear band between 45 and 55 kD, and glycosyltransferases GT29-4, GT29-5, GT29-7, GT29-9, GT29-11, GT29-13, GT29-17, GT29-18, GT29-24 and GT29-25 had a small amount of soluble expression in *E. coli*.

Example 5 In Vitro Transglycosylation Activity and Products Identification of GT29-4, GT29-5, GT29-7, GT29-9, GT29-11, GT29-13, GT29-17, GT29-18, GT29-24 and GT29-25

The cell lysate supernatants of recombinant *E. coli* BL21-GT29-4, BL21-GT29-5, BL21-GT29-7, BL21-GT29-9, BL21-GT29-11, BL21-GT29-13, BL21-GT29-17, BL21-GT29-18, BL21-GT29-24 and BL21-GT29-25 in Example 2 was used as a crude enzyme solution for transglycosylation reaction, and cell lysate of recombinant *E. coli* with empty vector pET28a was used as a control.

As shown in FIG. 7, using the Protopanaxadiol Ginsenoside Rg1 as a glycosyl acceptor, UDP-xylose as a glycosyl donor, GT29-4, GT29-5, GT29-7, GT29-9, GT29-11, GT29-13, GT29-17, GT29-18, GT29-24 and GT29-25 can catalyze the formation of Notoginsenoside R1. The HPLC results are consistent with the TLC results (FIG. 8 and FIG. 9). Therefore, GT29-4, GT29-5, GT29-7, GT29-9, GT29-11, GT29-13, GT29-17, GT29-18, GT29-24, and GT29-25 are capable of catalyzing the extension of C6-O-Glc of Rg1 by a molecule of xylose to produce notoginsenoside R1.

As shown in FIG. 10, GT29-24 and GT29-25 can use Protopanaxadiol Ginsenoside Rh2 as a glycosyl acceptor and UDP-glucose as a glycosyl donor to catalyze the production of ginsenoside Rg3 by extending a glucosyl at the C-3 glycosyl of Rh2. When the substrate is changed to F2, GT29-24 and GT29-25 can further catalyze the extension of a glucosyl at the C-3 glycosyl of F2 to produce ginsenoside Rd.

Example 6 Isolation of *Panax notoginseng* Glycosyltransferase and the Coding Gene Thereof RNA in *Panax notoginseng* was extracted and reverse transcription was performed to obtain cDNA of *Panax notoginseng*. Using this cDNA as a template, primer pair 1 (SEQ ID NO.: 82 and SEQ ID NO.: 83), primer pair 2 (SEQ ID NO.: 84 and SEQ ID NO.: 85), primer pair 3 (SEQ ID NO.: 84 and SEQ ID NO.: 86), primer pair 4 (SEQ ID NO.: 87 and SEQ ID NO.: 88) were used for PCR amplification to obtain a 1.4-1.5 kb amplification product. The high-fidelity KOD DNA polymerase from Bao Bioengineering Co., Ltd. was used as the DNA polymerase. PCR products were detected by agarose gel electrophoresis.

According to Example 1, several clones were selected to extract recombinant plasmids and sequenced to obtain 14 different nucleic acid sequences, named PNUGT29-1 (SEQ ID NO.: 38), PNUGT29-2 (SEQ ID NO.: 40), PNUGT29-3 (SEQ ID NO.: 42), PNUGT29-4 (SEQ ID NO.: 44), PNUGT29-5 (SEQ ID NO.: 46), PNUGT29-6 (SEQ ID NO.: 48), PNUGT29-7 (SEQ ID NO.: 50), PNUGT29-8 (SEQ ID NO.: 52), PNUGT29-9 (SEQ ID NO.: 54), PNUGT29-14 (SEQ ID NO.: 56) and PNUGT29-15 (SEQ ID NO.: 58), respectively. BESTORF software was used to find ORF. Through sequence alignment, the amplification products all have the conserved functional domain of glycosyltransferase family 1, indicating that it is a glycosyltransferase gene.

PNUGT29-1: The glycosyltransferase gene PNUGT29-1 encodes a protein PNUGT29-1 containing 447 amino acids with the amino acid sequence as shown in SEQ ID NO: 39 in the sequence listing. The theoretical molecular weight of the protein is predicted to be 49.688 kDa by software, and the isoelectric point pI is 6.58.

PNUGT29-2: The glycosyltransferase gene PNUGT29-2 encodes a protein PNUGT29-2 containing 442 amino acids with the amino acid sequence as shown in SEQ ID NO: 41 in the sequence listing. The theoretical molecular weight of the protein is predicted to be 49.118 kDa by software, and the isoelectric point pI is 6.20.

PNUGT29-3: The glycosyltransferase gene PNUGT29-3 encodes a protein PNUGT29-3 containing 447 amino acids with the amino acid sequence as shown in SEQ ID NO: 43 in the sequence listing. The theoretical molecular weight of the protein is predicted to be 49.729 kDa by software, and the isoelectric point pI is 6.58.

PNUGT29-4: The glycosyltransferase gene PNUGT29-4 encodes a protein PNUGT29-4 containing 447 amino acids with the amino acid sequence as shown in SEQ ID NO: 45 in the sequence listing. The theoretical molecular weight of the protein is predicted to be 49.715 kDa by software, and the isoelectric point pI is 6.58.

PNUGT29-5: The glycosyltransferase gene PNUGT29-5 encodes a protein PNUGT29-5 containing 447 amino acids with the amino acid sequence as shown in SEQ ID NO: 47 in the sequence listing. The theoretical molecular weight of the protein is predicted to be 49.718 kDa by software, and the isoelectric point pI is 6.45.

PNUGT29-6: The glycosyltransferase gene PNUGT29-6 encodes a protein PNUGT29-6 containing 447 amino acids with the amino acid sequence as shown in SEQ ID NO: 49 in the sequence listing. The theoretical molecular weight of the protein is predicted to be 49.657 kDa by software, and the isoelectric point pI is 6.70.

PNUGT29-7: The glycosyltransferase gene PNUGT29-7 encodes a protein. PNUGT29-7 containing 447 amino acids with the amino acid sequence as shown in SEQ ID NO: 51 in the sequence listing. The theoretical molecular weight of the protein is predicted to be 49.749 kDa by software, and the isoelectric point pI is 6.58.

PNUGT29-8: The glycosyltransferase gene PNUGT29-8 encodes a protein.

PNUGT29-8 containing 447 amino acids with the amino acid sequence as shown in SEQ ID NO: 53 in the sequence listing. The theoretical molecular weight of the protein is predicted to be 49.657 kDa by software, and the isoelectric point pI is 6.70.

PNUGT29-9: The glycosyltransferase gene PNUGT29-9 encodes a protein PNUGT29-9 containing 447 amino acids with the amino acid sequence as shown in SEQ ID NO: 55 in the sequence listing. The theoretical molecular weight of the protein is predicted to be 49.695 kDa by software, and the isoelectric point pI is 6.58.

PNUGT29-14: The glycosyltransferase gene PNUGT29-14 encodes a protein PNUGT29-14 containing 447 amino acids with the amino acid sequence as shown in SEQ ID NO: 57 in the sequence listing. The theoretical molecular weight of the protein is predicted to be 49.778 kDa by software, and the isoelectric point pI is 6.70. PNUGT29-15: The glycosyltransferase gene.

PNUGT29-15 encodes a protein PNUGT29-15 containing 447 amino acids with the amino acid sequence as shown in SEQ ID NO: 59 in the sequence listing. The theoretical molecular weight of the protein is predicted to be 49.755 kDa by software, and the isoelectric point pI is 6.63.

Example 7 Expression of *Panax notoginseng* Glycosyltransferase Genes PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and NUGT29-15 in *E. coli*

Plasmids PNUGT29-1-pMD18T, PNUGT29-2-pMD18T, PNUGT29-3-pMD18T, PNUGT29-4-pMD18T, PNUGT29-5-pMD18T, PNUGT29-6-pMD18T, PNUGT29-7-pMD18T, PNUGT29-8-pMD18T, PNUGT29-9-pMD18T, PNUGT29-14-pMD18T and PNUGT29-15-pMD18T containing PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 genes constructed in Example 6 were used as a template, and the target genes PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 were amplified with the primers as shown in Table 1. Referring to the method in Example 2, the recombinant strains BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7. BL21-PNUGT29-8, BL21-PNUGT29-9, BL21-PNUGT29-14 and BL21-PNUGT29-15 were constructed for SDS-PAGE electrophoresis and western blot. Anti-6×His tag Western Blot (FIG. 10) shows that there is a clear band between 45 and 65 kD, glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 have a small amount of soluble expression in *E. coli*.

TABLE 2 primers used to amplify genes

| gene | primer | SEQ ID NO. |
|---|---|---|
| PNUGT29-1 | PNUGT29-1-F | 60 |
|  | PNUGT29-1-R | 61 |
| PNUGT29-2 | PNUGT29-2-F | 62 |
|  | PNUGT29-2-R | 63 |
| PNUGT29-3 | PNUGT29-3-F | 64 |
|  | PNUGT29-3-R | 65 |
| PNUGT29-4 | PNUGT29-4-F | 66 |
|  | PNUGT29-4-R | 67 |
| PNUGT29-5 | PNUGT29-5-F | 68 |
|  | PNUGT29-5-R | 69 |
| PNUGT29-6 | PNUGT29-6-F | 70 |
|  | PNUGT29-6-R | 71 |
| PNUGT29-7 | PNUGT29-7-F | 72 |
|  | PNUGT29-7-R | 73 |
| PNUGT29-8 | PNUGT29-8-F | 74 |
|  | PNUGT29-8-R | 75 |
| PNUGT29-9 | PNUGT29-9-F | 76 |
|  | PNUGT29-9-R | 77 |
| PNUGT29-14 | PNUGT29-14-F | 78 |
|  | PNUGT29-14-R | 79 |
| PNUGT29-15 | PNUGT29-15-F | 80 |
|  | PNUGT29-15-R | 81 |

Example 8 In Vitro Transglycosylation Activity and Product Identification of *Panax notoginseng* Glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15

The cell lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14 and BL21-PNUGT29-15 in Example 7 were used as a crude enzyme solution for transglycosylation reaction. Cell lysate of recombinant *E. coli* with empty vector pET28a was used as a control.

As shown in FIG. 11: using Protopanaxadiol Ginsenoside Rd as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-20 glycosyl of Rd to generate Rb1.

As shown in FIG. 12: using Protopanaxadiol Ginsenoside CK as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-20 glycosyl to generate Gypenoside LXXV.

As shown in FIG. 13: using Protopanaxadiol Ginsenoside Rh2 as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-3 glycosyl of Rh2 to generate Rg3.

Example 9 Expression of Glycosyltransferase Genes GT29-19, GT29-20, GT29-21, GT29-22, GT29-23, GT29-36, GT29-37, GT29-42, GT29-43, GT29-45 and GT29-46 in *E. coli*

Plasmids GT29-19-pMD18T, GT29-20-pMD18T, GT29-21-pMD18T, GT29-22-pMD18T, GT29-23-pMD18T, GT29-36-pMD18T, GT29-37-pMD18T, GT29-42-pMD18T, GT29-43-pMD18T, GT29-45-pMD18T, and GT29-46-pMD18T containing GT29-19, GT29-20, GT29-21, GT29-22, GT29-23, GT29-36, GT29-37, GT29-42, GT29-43, GT29-45 and GT29-46 genes constructed in Example 1 were used as a template, and the target genes GT29-36, GT29-37, GT29-42, GT29-43, GT29-45 and GT29-46 were amplified with the primers as shown in Table 1.

Referring to Example 2, recombinant strains BL21-GT29-19, BL21-GT29-20, BL21-GT29-21, BL21-GT29-22, BL21-GT29-23, BL21-GT29-36, BL21-GT29-37, BL21-GT29-42, BL21-GT29-43, BL21-GT29-45 and BL21-GT29-46 were constructed, and samples were taken for SDS-PAGE electrophoresis and western blot.

Protopanaxadiol Ginsenoside Rh2 was used as a glycosyl acceptor, and UDP-glucose was used as a glycosyl donor, and the above-mentioned glycosyltransferases GT29-19, GT29-20, GT29-21, GT29-22, GT29-23, GT29-36, GT29-37, GT29-42, GT29-43, GT29-45 and GT29-46 can all catalyze the extension of a glucosyl at the C-3 glycosyl of Rh2 to generate Rg3. FIG. 15 shows GT29-45 and GT29-46 can catalyze Rh2 to generate Rg3.

Protopanaxadiol Ginsenoside Rd was used as a glycosyl acceptor and UDP-xylose was used as a glycosyl donor, and the above glycosyltransferases GT29-19, GT29-20, GT29-21, GT29-22, GT29-23, GT29-36, GT29-37, GT29-42, GT29-43 can all catalyze the replacement of the second glucose at C-3 position of Rd with xylose to produce a new triterpene saponin (3-O-β-(D-xylopyranosyl)-β-(D-glucopyranosyl), 20-O-β-(D-glucopyranosyl)-PPD), of which GT29-36, GT29-37, GT29-42 and GT29-43 are the most active (FIG. 14).

As shown in FIG. 16: Protopanaxadiol Ginsenoside CK is used as a glycosyl acceptor, and UDP-glucose is used as a glycosyl donor. GT29-45 and GT29-46 can catalyze the C-20 glycosyl of CK to extend a glucosyl to produce Gypenoside LXXV, in which GT29-45 has a strong activity.

Example 10 Further Verification of the Glycosyltransferase Activity

The above Examples 3, 5, and 8 were repeated, and the difference was that other glycosyl donors and substrates were replaced, and the experimental results are shown in Table 3 to Table 5:

TABLE 3

| SEQ ID NO.: | name | C-3 UDP-xylose Rd | C-3 UDP-G F2 | C-3 UDP-G Rh2 |
|---|---|---|---|---|
| 116 | GT29-19 | ++ | ++ | +++ |
| 118 | GT29-20 | ++ | ++ | +++ |
| 120 | GT29-21 | + | ++ | +++ |
| 122 | GT29-22 | + | ++ | ++ |
| 124 | GT29-23 | + | ++ | ++ |
| 90 | GT29-36 | +++ | ++ | ++ |
| 92 | GT29-37 | +++ | ++ | ++ |
| 94 | GT29-42 | +++ | ++ | ++ |
| 96 | GT29-43 | +++ | ++ | ++ |
| 98 | GT29-45 | NS | ++ | ++ |
| 100 | GT29-46 | NS | ++ | ++ |
| 39 | PNUGT29-1 | NS | ++ | +++ |
| 41 | PNUGT29-2 | NS | +++ | +++ |
| 43 | PNUGT29-3 | NS | +++ | +++ |
| 45 | PNUGT29-4 | NS | +++ | +++ |
| 47 | PNUGT29-5 | NS | ++ | ++ |
| 49 | PNUGT29-6 | NS | ++ | ++ |
| 51 | PNUGT29-7 | NS | ++ | ++ |
| 53 | PNUGT29-8 | NS | ++ | ++ |
| 55 | PNUGT29-9 | NS | +++ | +++ |
| 57 | PNUGT29-14 | NS | ++ | ++ |
| 59 | PNUGT29-15 | NS | ++ | ++ |

TABLE 4

| SEQ ID NO.: | name | C-6 UDP-xylose Rg1 | C-6 UDP-xylose Rh1 | C-6 UDP-G Rg1 | C-6 UDP-G Rh1 |
|---|---|---|---|---|---|
| 12 | GT29-4 | ++ | ++ | + | + |
| 14 | GT29-5 | ++ | ++ | + | + |
| 16 | GT29-7 | +++ | ++ | ++ | ++ |
| 18 | GT29-9 | ++ | ++ | + | + |
| 20 | GT29-11 | +++ | +++ | ++ | ++ |
| 22 | GT29-13 | ++ | ++ | ++ | ++ |
| 24 | GT29-17 | ++ | ++ | + | + |
| 26 | GT29-18 | +++ | +++ | ++ | ++ |
| 28 | GT29-24 | +++ | +++ | ++ | ++ |
| 30 | GT29-25 | +++ | +++ | + | + |

TABLE 5

| SEQ ID NO.: | name | C-20 UDP-xylose Rd | C-20 UDP-G CK | C-20 UDP-G F1 | C-20 UDP-arabinose Rd | C-20 UDP-arabinose CK |
|---|---|---|---|---|---|---|
| 4 | GT29-32 | +++ | +++ | ++ | + | ++ |
| 6 | GT29-33 | + | ++ | + | ++ | ++ |
| 8 | GT29-34 | + | ++ | + | ++ | ++ |
| 98 | GT29-45 | + | ++ | + | + | NS |
| 100 | GT29-46 | + | + | + | + | NS |
| 39 | PNUGT29-1 | + | +++ | + | + | NS |
| 41 | PNUGT29-2 | + | + | + | + | NS |
| 43 | PNUGT29-3 | + | +++ | ++ | + | NS |
| 45 | PNUGT29-4 | + | +++ | ++ | ++ | NS |
| 47 | PNUGT29-5 | + | +++ | + | ++ | NS |
| 49 | PNUGT29-6 | + | +++ | ++ | ++ | NS |
| 51 | PNUGT29-7 | + | +++ | + | + | NS |
| 53 | PNUGT29-8 | + | +++ | + | + | NS |
| 55 | PNUGT29-9 | + | +++ | + | + | NS |
| 57 | PNUGT29-14 | + | +++ | + | + | NS |
| 59 | PNUGT29-15 | + | +++ | + | + | NS |

* NS stands for not shown

It can be seen from Tables 3 to 5 that the glycosyltransferases of the present invention can utilize common glycosyl donors and substrates, and have glycosyl extension or glycosyl substitution activity on different sites of tetracyclic triterpenes.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. An in vitro glycosylation method, comprising the steps of:
  (a) expressing a glycosyltransferase in a host cell, wherein the glycosyltransferase comprises; SEQ ID NO:4;
  (b) collecting lysates of the host cell wherein the glycosyltransferase has been expressed; and
  (c) in vitro transferring a glycosyl group from a glycosyl donor to the following positions of a tetracyclic triterpenoid in the presence of the lysates of the host cell: the first glycosyl group at position C20, or positions C3 and C20; thereby forming a glycosylated tetracyclic triterpenoid.

2. The method of claim 1, wherein the glycosyltransferase further comprises a tag sequence or a signal sequence, and wherein the glycosyltransferase is operably linked to the tag sequence or signal sequence.

3. The method of claim 2, wherein the tag sequence is selected from the group consisting of FLAG, HA, HA1, c-Myc, Poly-His with 2-10 residues, Poly-Arg with 5-6 residues, and Strep-TagII.

4. The method of claim 2, wherein the signal sequence comprises a pelB signal peptide sequence.

5. The method of claim 1, wherein the glycosyl donor comprises UDP-glucose, UDP-xylose, UDP-arabinose, or any combination thereof.

6. The method of claim 1, wherein the tetracyclic triterpenoid comprises protopanaxadiol ginsenoside CK, ginsenoside Rd, protopanaxatriol ginsenoside F1, or a combination thereof.

* * * * *